US 11,248,021 B2

(12) United States Patent
Crine et al.

(10) Patent No.: US 11,248,021 B2
(45) Date of Patent: Feb. 15, 2022

(54) BONE DELIVERY CONJUGATES AND METHOD OF USING SAME TO TARGET PROTEINS TO BONE

(71) Applicant: Alexion Pharmaceuticals, Inc., Boston, MA (US)

(72) Inventors: Philippe Crine, Outremont (CA); Guy Boileau, Brossard (CA); Isabelle Lemire, Montreal (CA); Thomas P. Loisel, Montreal (CA)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 16/235,646

(22) Filed: Dec. 28, 2018

(65) Prior Publication Data

US 2019/0119323 A1 Apr. 25, 2019

Related U.S. Application Data

(63) Continuation of application No. 14/931,310, filed on Nov. 3, 2015, now abandoned, which is a continuation of application No. 12/638,527, filed on Dec. 15, 2009, now Pat. No. 10,000,532, which is a continuation of application No. 11/111,664, filed on Apr. 21, 2005, now Pat. No. 7,763,712.

(60) Provisional application No. 60/614,984, filed on Oct. 4, 2004, provisional application No. 60/590,347, filed on Jul. 23, 2004, provisional application No. 60/563,828, filed on Apr. 21, 2004.

(51) Int. Cl.
| | |
|---|---|
| *C07K 7/06* | (2006.01) |
| *C07K 14/51* | (2006.01) |
| *C12N 9/16* | (2006.01) |
| *C12N 9/64* | (2006.01) |
| *A61K 47/64* | (2017.01) |
| *A61K 38/00* | (2006.01) |

(52) U.S. Cl.
CPC .............. *C07K 7/06* (2013.01); *A61K 47/645* (2017.08); *C07K 14/51* (2013.01); *C12N 9/16* (2013.01); *C12N 9/6421* (2013.01); *C12N 9/6494* (2013.01); *C12Y 304/24011* (2013.01); *A61K 38/00* (2013.01); *C07K 2319/01* (2013.01); *C07K 2319/23* (2013.01); *C12Y 301/03001* (2013.01)

(58) Field of Classification Search
None
See application file for complete search history.

(56) References Cited

U.S. PATENT DOCUMENTS

| | | |
|---|---|---|
| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

"View of NCT02235493 on Nov. 19, 2015," ClinicalTrials.gov archive, Nov. 19, 2015 (4 pages).
Achord et al., "Human beta-glucuronidase: in vivo clearance and in vitro uptake by a glycoprotein recognition system on reticuloendothelial cells," Cell 15(1):269-278 (1978).
Addison et al., "Pyrophosphate inhibits mineralization of osteoblast cultures by binding to mineral, up-regulating osteopontin, and inhibiting alkaline phosphatase activity," J Biol Chem. 282(21):15872-15883 (2007).
Advisory Action for U.S. Appl. No. 11/484,870, dated Dec. 20, 2007 (4 pages).

(Continued)

*Primary Examiner* — Anand U Desai
(74) *Attorney, Agent, or Firm* — Clark & Elbing LLP

(57) ABSTRACT

A bone delivery conjugate having a structure selected from the group consisting of: A) X-$D_n$-Y-protein-Z; and B) Z-protein-Y-$D_n$-X, wherein X is absent or is an amino acid sequence of at least one amino acid; Y is absent or is an amino acid sequence of at least one amino acid; Z is absent or is an amino acid sequence of at least one amino acid; and $D_n$ is a poly aspartate wherein n=10 to 16. Compositions comprising same and methods of use thereof.

8 Claims, 18 Drawing Sheets

Specification includes a Sequence Listing.

(56) References Cited

U.S. PATENT DOCUMENTS

| | | |
|---|---|---|
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,988,620 B2 | 6/2018 | Crine et al. |
| 10,000,532 B2 | 6/2018 | Crine et al. |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1 | 11/2010 | Crine et al. |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0052968 A1 | 2/2016 | Crine et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |

FOREIGN PATENT DOCUMENTS

| | | |
|---|---|---|
| EP | 0771875 B1 | 5/1997 |
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |
| EP | 1759001 B1 | 3/2007 |
| EP | 1759710 A1 | 3/2007 |
| EP | 2158319 | 3/2010 |
| EP | 2158319 B1 | 12/2011 |
| JP | H0870875 A | 3/1996 |

(56) References Cited

FOREIGN PATENT DOCUMENTS

| | | |
|---|---|---|
| JP | 2000-327583 A | 11/2000 |
| JP | 2002-541776 A | 12/2002 |
| JP | 2007-511209 A | 5/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/110435 A1 | 11/2005 |
| WO | WO-2006/005140 A1 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2015/112015 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |

OTHER PUBLICATIONS

Ahn et al., "Idiopathic calcium pyrophosphate dihydrate (CPPD) crystal deposition disease in a young male patient: a case report," J Korean Med Sci. 18(6):917-20 (2003).

Alexion Pharma International, "Strensiq Product Monograph," <http://alexionpharma.ca/documents/Strensiq-PM-asfotase-alfa-14Aug2015.aspx>, Prepared Aug. 14, 2015 (32 pages).

Alexion Third Quarter 2017 Earnings Call, "http://files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).

Alexion, "Highlights of Prescribing Information" for Strensiq®, 2018 (8 pages).

Ali et al., "Isolation and characterization of calcifying matrix vesicles from epiphyseal cartilage," Proc Natl Acad Sci USA. 67(3):1513-1520 (1970).

Altarescu et al., "The efficacy of enzyme replacement therapy in patients with chronic neuronopathic Gaucher's disease," J Pediatr. 138(4):539-547 (2001).

Anderson et al., "Impaired calcification around matrix vesicles of growth plate and bone in alkaline phosphatase-deficient mice," *Am J Pathol.* 164(3):841-847 (2004).

Anderson et al., "Matrix vesicles in osteomalacic hypophosphatasia bone contain apatite-like mineral crystals," Am J Pathol. 151(6):1555-61 (1997).

Anderson et al., "Pyrophosphate stimulation of calcium uptake into cultured embryonic bones. Fine structure of matrix vesicles and their role in calcification," Dev Biol. 34:211-227 (1973).

(56) References Cited

OTHER PUBLICATIONS

Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).
Anderson et al., "The role of matrix vesicles in growth plate development and biomineralization," Front Biosci. 10:822-837 (2005).
Appeal Brief as Filed in U.S. Appl. No. 12/638,527, dated Oct. 9, 2015 (101 pages).
Attwood, "The Babel of Bioinformatics," Science. 290(5491): 471-3 (2000).
Barranger et al., "Lessons learned from the development of enzyme therapy for Gaucher disease," J Inherit Metab Dis. 24(Suppl. 2):89-96 (2001).
Barton et al., "Replacement therapy for inherited enzyme deficiency—macrophage-targeted glucocerebrosidase for Gaucher's disease," N Engl J Med. 324(21):1464-70 (1991) (abstract only).
Beertsen et al., "Root development in mice lacking functional tissue non-specific alkaline phosphatase gene: Inhibition of acellular cementum formation," J Dent Res. 78(6):1221-1229 (1999) (10 pages).
Belachew et al., "Infantile hypophosphatasia secondary to a novel compound heterozygous mutation presenting with pyridoxine-responsive seizures," JIMD Rep. 11:17-24 (2013).
Belkhouribchia et al., "Osteomalacia with low alkaline phosphatase: a not so rare condition with important consequences," BMJ Case Rep. doi: 10.1136/bcr-2015-212827 (2016) (4 pages).
Bennett et al., "Extracellular domain-IgG fusion proteins for three human natriuretic peptide receptors," J Biol Chem. 266(34):23060-23067 (1991).
Berkseth et al., "Clinical spectrum of hypophosphatasia diagnosed in adults," Bone. 54(1):21-7 (2013).
Bernard, "Ultrastructural localization of alkaline phosphatase in initial intramembranous osteogenesis," Clin Orthop Relat Res. 135:218-225 (1978).
Bernardi, "Chromatography of proteins on hydroxyapatite," Methods Enzymol. 27:471-9 (1973).
Bhattacharyya et al., "Hypophosphatasia and the risk of atypical femur fractures: a case-control study," BMC Muscoloskelet Disord. 17:332 (2016) (4 pages).
Bianchi, "Hypophosphatasia: an overview of the disease and its treatment," Osteoporos Int. 26(12):2743-57; DOI 10.1007/s00198-015-3272-1 (2015) (15 pages).
Bishop et al., "Transformative therapy in hypophosphatasia," Arch Dis Child. 101(6):514-5 (2016).
Bishop, "Asfotase alfa for hypophosphatasia," Horizon Scanning Centre. National Institute for Health Research. http://www.hsric.nihr.ac.uk/topics/asfotase-alfa-for-hypophosphatasia/download, retrieved Oct. 20, 2013 (9 pages).
Bishop, "Clinical management of hypophosphatasia," Clin Cases Miner Bone Metab. 12(2):170-3 (2015).
Bloch-Zupan, "Hypophosphatasia: diagnosis and clinical signs—a dental surgeon perspective," Int J Paediatr Dent. 26(6):426-438 (2016).
Bobryshev et al., "Role of bone-type tissue-nonspecific alkaline phosphatase and PHOSPO1 in vascular calcification," Curr Pharm Des. 20(37):5821-8 (2014).
Bobyr et al., "High-resolution analysis of Zn(2+) coordination in the alkaline phosphatase superfamily by EXAFS and x-ray crystallography," J Mol Biol. 415(1):102-17 (2012).
Bobé et al., "Fas-mediated liver damage in MRL hemopoietic chimeras undergoing lpr-mediated graft-versus-host disease," J Immunol. 159:4197-4204 (1997).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Bonilla, "Pharmacokinetics of immunoglobulin administered via intravenous or subcutaneous routes," Immunol Allergy Clin N Am. 28:803-819 (2008).

Boskey et al., "Matrix vesicles promote mineralization in a gelatin gel," Calcif Tissue Int 60(3):309-15 (1997).
Boskey, "Amorphous calcium phosphate: The contention of bone," J Dent Res. 76:1433-1436 (1997).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Braunstein, "Multiple fractures, pain, and severe disability in a patient with adult-onset hypophosphatasia," Bone Rep. 4:1-4 (2016).
Brenner et al., "Diverse biological actions of atrial natriuretic peptide," Physiol Rev. 70(3):665-699 (1990).
Briot et al., "Adult hypophosphatasia," Curr Opin Rheumatol. 28(4):448-51 (2016).
Buchet et al., "Chapter 3: Multisystemic functions of alkaline phosphatases," *Phosphatase Modulators, Methods in Molecular Biology*, vol. 1053. José Luis Millán (ed.), 27-51 (2013).
Byers et al., "Effect of enzyme replacement therapy on bone formation in a feline model of mucopolysaccharidosis type VI," Bone. 21(5):425-431 (1997).
Cahill et al., "Infantile hypophosphatasia: transplantation therapy trial using bone fragments and cultured osteoblasts," J. Clin Endocrinol Metab. 92(8): 2923-30 (2007).
Cameron et al., "Minireview: Natriuretic peptides during development of the fetal heart and circulation," Endocrinology. 144(6):2191-2194 (2003).
Campbell et al., "Insulin-like growth factor (IGF)-binding protein-5-(201-218) region regulates hydroxyapatite and IGF-I binding," Am J Physiol Endocrinol Metab. 273:E1005-1013 (1997).
Center for Drug Evaluation and Research, "Application No. 125513Orig1s000," <http://www.accessdata.fda.gov/drugsatfda_docs/nda/2015/125513Orig1s000MedR.pdf>, review completed Oct. 20, 2015; retrieved on Jun. 1, 2016 (254 pages).
Chen et al., "Gly369Cys mutation in mouse FGFR3 causes achondroplasia by affecting both chondrogenesis and osteogenesis," J Clin Invest. 104(11):1517-1525 (1999).
Choe et al., "Substrate profiling of cysteine proteases using a combinatorial peptide library identifies functionally unique specificities," J Biol Chem. 281(18):12824-12832 (2006).
Chusho et al., "Dwarfism and early death in mice lacking C-type natriuretic peptide," Proc Natl Acad Sci USA. 98(7):4016-4021 (2001).
Ciancaglini et al., "Contribution of matrix vesicles and alkaline phosphatase to ectopic bone formation," Braz J Med Biol Res. 39(5):603-10 (2006).
Cleland et al., "Emerging protein delivery methods," Curr Opin Biotechnol. 12:212-219 (2001).
Clemens et al., "Pharmacokinetics and biological actions of subcutaneously administered human brain natriuretic peptide," J Pharmacol Exp Ther. 287(1):67-71 (1998).
Communication from Examining Division for European Application No. 05739065.0, dated Jun. 11, 2010 (5 pages).
Communication from Examining Division for European Application No. 05739065.0, dated Jun. 18, 2009 (6 pages).
Communication from Examining Division for European Application No. 08757088.3, dated Apr. 20, 2011 (4 pages).
Crawley et al., "Enzyme replacement therapy in a feline model of Maroteaux-Lamy Syndrome," J Clin Invest. 97(8):1864-73 (1996).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
Data Sheet for pFUSE-SEAP-hFC "Plasmid designed for the expression of a SEAP-Fc Fusion protein," Invivogen, San Diego, CA (4 pages) (1989).
De la Croix Ndong et al., "Asfotase-alpha improves bone growth, mineralization and strength in mouse models of neurofibromatosis type-1," Nat Med. 20(8):904-10 (2014) (10 pages).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(3):847-857 (1998).
De Roo et al., "Infantile hypophosphatasia without bone deformities presenting with severe pyridoxine-resistant seizures," Mol Genet Metab. 111(3):404-7 (2014).

(56) References Cited

OTHER PUBLICATIONS

Declaration of Dr. Philippe Crine for European Patent Application No. 08757088.3, executed Jan. 14, 2011 (6 pages).
Deeb et al., "Could alerting physicians for low alkaline phosphatase levels be helpful in early diagnosis of hypophosphatasia?," J Clin Res Pediatr Endocrinol. 10(1):19-24 (2018).
Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).
Durussel et al., "Bone mineralization-dependent craniosynostosis and craniofacial shape abnormalities in the mouse model of infantile hypophosphatasia," Dev Dyn. 245(2):175-82 (2016).
EBI Blast for Accession No. ATD17216. Entered Oct. 16, 2008 (1 page).
Eng et al., "Safety and efficacy of recombinant human alpha-galactosidase A replacement therapy in Fabry's disease," N Engl J Med. 345(1):9-16 (2001).
Engel et al., "Characterization of the hormone binding site of natriuretic peptide receptor-C," FEBS Lett. 360:169-172 (1995).
Epps, "Application No. 125513Orig1s000 Medical Review(s)," Center for Drug Evaluation and Research, <http://www.accessdata.fda.gov/drugsatfda_docs/nda/2015/125513Orig1s000MedR.pdf>, Oct. 20, 2015 (254 pages).
European Collection of Authenticated Cell Cultures (ECACC), General Cell Collection: NS0, Catalogue No. 85110503. Retrieved May 2, 2018 (3 pages).
Extended European Search Report for European Application No. 08757088.3, dated Jun. 21, 2010 (6 pages).
European Search Report for European Patent Application No. 12842640.0, dated Mar. 13, 2015 (7 pages).
Examiner's Answer to Appeal Brief for U.S. Appl. No. 12/638,527, dated Feb. 23, 2016 (9 pages).
Extended European Search Report for European Application No. 11774253.6, dated Oct. 14, 2013 (8 pages).
Extended European Search Report for European Application No. 11000196.3, dated Jun. 22, 2011 (6 pages).
Extended European Search Report for European Application No. 11004496.3, dated Aug. 26, 2011 (7 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Fodor et al., "Differencial diagnosis of the low alkaline phosphatase activities," Orv Hetil. 158(26): 1003-1007 (2017) (Article in Hungarian) (English Abstract included).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).
Furuya et al., "Structural requirements of C-type natriuretic peptide for elevation of cyclic GMP in cultured vascular smooth muscle cells," Biochem Biophys Res Commun. 183(3):964-969 (1992).

Garg, "Investigation of the role of FcRn in the absorption, distribution, and elimination of monoclonal antibodies," Dissertation: State University of New York at Buffalo, 2007 (Abstract only) (2 pages).
Gasque et al., "Improvement of the skeletal and dental hypophosphatasia phenotype in Alpl-/- mice by administration of soluble (non-targeted) chimeric alkaline phosphatase," Available in PMC Mar. 1, 2016, published in final edited form as: Bone. 72:137-147 (2015) (25 pages).
Gates et al., "Effects of age, sex, and comorbidities on the pediatric outcomes data collection instrument (PODCI) in the general population," J Pediatr Orthop. 35(2):203-9 (2015).
Gilbert et al., "Chimeric peptides of statherin and osteopontin that bind hydroxyapatite and mediate cell adhesion," J Biol Chem. 275(21):16213-8 (2000).
Glass et al., "The infant skull: a vault of information," Radiographics. 24(2):507-22 (2004).
Graham et al., "Characteristics of a human cell line transformed by DNA from human adenovirus type 5," J Gen Virol. 36(1):59-72 (1977).
Greenberg et al., "A homoallelic Gly$^{317}$ to Asp mutation in ALPL causes the perinatal (lethal) form of hypophosphatasia in Canadian mennonites," Genomics. 17:215-217 (1993).
Guo et al., "Protein tolerance to random amino acid change," Proc Natl Acad Sci USA. 101(25):9205-9210 (2004).
Güzel Nur et al., "Pyridoxine-responsive seizures in infantile hypophosphatasia and a novel homozygous mutation in ALPL gene," J Clin Res Pediatr Endocrinol. 8(3):360-4 (2016).
Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol. 270:C1311-C1318 (1996).
Halling Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).
Hardy et al., "Dissection of a carboxy-terminal region of the yeast regulatory protein RAP1 with effects on both transcriptional activation and silencing," Mol Cell Biol. 12(3):1209-1217 (1992).
Harmey et al., "Concerted regulation of inorganic pyrophosphate and osteopontin by Akp2, Enpp1, and Ank," Am J Pathol. 164(4):1199-1209 (2004).
Harmey et al., "Elevated skeletal osteopontin levels contribute to the hypophosphatasia phenotype in Akp2$^{-/-}$ mice," J Bone Miner Res. 21(9):1377-1386 (2006).
Harris, "The human alkaline phosphatases: what we know and what we don't know," Clin Chim Acta. 186:133-50 (1989).
Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Henthorn et al., "Missense mutations of the tissue-nonspecific alkaline phosphatase gene in hypophosphatasia," Clin Chem. 38(12):2501-5 (1992).
Herasse et al., "Molecular study of three cases of odontohypophosphatasia resulting from heterozygosity for mutations in the tissue non-specific alkaline phosphatase gene," J Med Genet. 40(8):605-9 (2003).
Hessle et al., "Tissue-nonspecific alkaline phosphatase and plasma cell membrane glycoprotein-1 are central antagonistic regulators of bone mineralization," Proc Natl Acad Sci USA. 99(14): 9445-9449 (2002).
Highlights of Prescribing Information for Strensiq™, Alexion Pharmaceuticals, Inc., available <http://www.alexion.com/Documents/strensiq_pi-10-2015.aspx>, 2015 (19 pages).

(56) References Cited

OTHER PUBLICATIONS

Hofmann et al., "Asfotase alfa: enzyme replacement for the treatment of bone disease in hypophosphatasia," Drugs Today (Barc). 52(5):271-85 (2016).
Hofmann et al., "Clinical aspects of hypophosphatasia: an update," Clinic Rev Bone Miner Metab. 11(2):60-70 (2013).
Hofmann et al., "Compound heterozygosity of two functional null mutations in the ALPL gene associated with deleterious neurological outcome in an infant with hypophosphatasia," Bone. 55:150-7 (2013).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Salzburg, Austria. Bone Abstracts. 4: OC18 (2015) (3 pages).
Hofmann et al., "Recombinant enzyme replacement therapy in hypophosphatasia," Subcell Biochem. 76:323-41 (2015).
Horton et al., "Achondroplasia," Lancet. 370:162-172, 2007.
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Hult et al., "Engineered enzymes for improved organic synthesis," Curr Opin Biotechnol. 14:395-400 (2003).
Hunter et al., "Modulation of crystal formation by bone phosphoproteins: structural specificity of the osteopontin-mediated inhibition of hydroxyapatite formation," Biochem J. 300:723-728 (1994).
Husain et al., "Fc site-specific labeling of immunoglobulins with calf intestinal alkaline phosphatase," Bioconjug Chem. 5(5):482-90 (1994).
Ikezawa, "Glycosylphosphatidylinositol (GPI)-anchored proteins," *Biol Pharm Bull.* 25(4):409-417 (2002).
Inoue et al., "Four functionally distinct C-type natriuretic peptides found in fish reveal evolutionary history of the natriuretic peptide system," Proc Natl Acad Sci USA. 100(17):10079-10084 (2003).
International Preliminary Report on Patentability for International Patent Application No. PCT/CA2011/050258, dated Nov. 15, 2012 (9 pages).
International Preliminary Report on Patentability for International Patent Application No. PCT/US2012/039004, dated Apr. 22, 2014 (8 pages).
International Preliminary Report on Patentability for International Patent Application No. PCT/US2012/060869, dated Apr. 22, 2014 (7 pages).
International Preliminary Report on Patentability for International Patent Application No. PCT/US2016/015366, dated Aug. 10, 2017 (10 pages).
International Search Report and Written Opinion for International Patent Application No. PCT/CA2005/000615, dated Aug. 18, 2005 (14 pages).
International Search Report and Written Opinion for International Patent Application No. PCT/CA2008/000923, dated Sep. 12, 2008 (11 pages).
International Search Report and Written Opinion for International Patent Application No. PCT/CA2011/050258, dated Jul. 29, 2011 (14 pages).
International Search Report and Written Opinion for International Patent Application No. PCT/CA2011/050807, dated Apr. 13, 2012 (18 pages).
International Search Report and Written Opinion for International Patent Application No. PCT/US2012/039004, dated Nov. 2, 2012 (22 pages).
International Search Report and Written Opinion for International Patent Application No. PCT/US2015/039973, dated Oct. 5, 2015 (12 pages).
International Search Report and Written Opinion for International Patent Application No. PCT/US2015/058498, dated Jan. 22, 2016 (12 pages).
International Search Report and Written Opinion for International Patent Application No. PCT/US2015/064003, dated Mar. 31, 2016 (13 pages).
International Search Report and Written Opinion for International Patent Application No. PCT/US2016/015366, dated Aug. 9, 2016 (14 pages).
International Search Report and Written Opinion for International Patent Application No. PCT/US2016/025721, dated Aug. 17, 2016 (18 pages).
International Search Report and Written Opinion for International Patent Application No. PCT/US2016/039595, dated Feb. 21, 2017 (16 pages).
International Search Report and Written Opinion for International Patent Application No. PCT/US2016/047166, dated Nov. 7, 2016 (15 pages).
International Search Report and Written Opinion for International Patent Application No. PCT/US2016/049983, dated Nov. 29, 2016 (12 pages).
International Search Report and Written Opinion for International Patent Application No. PCT/US2016/054013, dated Dec. 13, 2016 (19 pages).
International Search Report and Written Opinion for International Patent Application No. PCT/US2017/025590, dated Jun. 29, 2017 (18 pages).
International Search Report and Written Opinion for International Patent Application No. PCT/US2017/025618, dated Jul. 11, 2017 (22 pages).
International Search Report and Written Opinion for International Patent Application No. PCT/US2017/036133, dated Aug. 24, 2017 (10 pages).
International Search Report and Written Opinion for International Patent Application No. PCT/US2017/047527, dated Nov. 6, 2017 (10 pages).
International Search Report and Written Opinion for International Patent Application No. PCT/US2018/020859, dated Jun. 19, 2018 (14 pages).
International Search Report and Written Opinion for International Patent Application No. PCT/US2018/025206, dated Jul. 3, 2018 (25 pages).
International Search Report for International Patent Application No. PCT/US2012/060869, dated Mar. 25, 2013 (5 pages).
Invitation to Pay Additional Fees for International Patent Application No. PCT/CA2011/050807, dated Feb. 13, 2012 (2 pages).
Invitation to Pay Additional Fees for International Patent Application No. PCT/US2012/039004, dated Aug. 29, 2012 (2 pages).
Invitation to Pay Additional Fees for International Patent Application No. PCT/US2016/015366, dated Jun. 1, 2016 (7 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ishida et al., "Tissue-nonspecific alkaline phosphatase with an Asp(289)—>Val mutation fails to reach the cell surface and undergoes proteasome-mediated degradation," J Biochem. 134(1):63-70 (2003).
Jansonius, "Structure, evolution and action of vitamin $B_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Johnson et al., "Motor proficiency in children with neurofibromatosis type 1," Pediatr Phys Ther. 22(4):344-8 (2010).
Kakkis et al., "Enzyme-replacement therapy in mucopolysaccharidosis I," N Engl J Med. 344(3):182-8 (2001).
Kalra et al., "The role of C-type natriuretic peptide in cardiovascular medicine," Eur Heart J. 22:997-1007 (2001).
Kasugai et al., "Selective drug delivery system to bone: small peptide $(Asp)_6$ conjugation," J Bone Miner Res. 15(5):936-943 (2000).

(56) References Cited

OTHER PUBLICATIONS

Kaufmann et al., "Influence of low temperature on productivity, proteome and protein phosphorylation of CHO cells," Biotechnol Bioeng. 63(5):573-82 (1999).
Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).
Kishnani et al., "Monitoring guidance for patients with hypophosphatasia treated with asfotase alfa," Mol Genet Metab. 122(1-2):4-17 (2017).
Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Kochendoerfer, "Protein & peptide drug delivery—third international conference: Minimally invasive delivery methods," Sep. 22-23, Philadelphia, PA. IDrugs. 6(11):1043-1045 (2003).
Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Kostenuik et al., "Infrequent delivery of a long-acting PTH-Fc fusion protein has potent anabolic effects on cortical and cancellous bone," J Bone Miner Res. 22(10):1534-1547 (2007).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Lazdunski et al., "Structure-function relationships for some metalloalkaline phosphatases of *E. coli*," Eur J Biochem. 8(4):510-7 (1969).
Le Du et al., "Crystal structure of alkaline phosphatase from human placenta at 1.8 Å resolution. Implication for a substrate specificity," J Biol Chem. 276(12):9158-65 (2001) (9 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Leone et al., "Allosteric modulation of pyrophosphatase activity of rat osseous plate alkaline phosphatase by magnesium ions," Int J Biochem Cell Biol. 30:89-97 (1998).
Li et al., "Standard reference for the six-minute-walk test in healthy children aged 7 to 16 years," Am J Respir Crit Care Med. 176(2):174-80 (2007).
Linglart et al., "Hypophosphatasia," Curr Osteoporos Rep. 14(3):95-105; DOI 10.1007/s11914-016-0309-0 (2016) (11 pages).
Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).
Lo et al., "High level expression and secretion of Fc-X fusion proteins in mammalian cells," Protein Eng. 11(6):495-500 (1998).
Lopez-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).
Madson et al., "Asfotase alfa: sustained efficacy and tolerability in children with hypophosphatasia treated for 5 years," ESPE Abstracts. 84:FC2.4 (2015) (2 pages).
Mahmood et al., "Selection of the first-time dose in humans: comparison of different approaches based on interspecies scaling of clearance," J Clin Pharmacol. 43:692-697 (2003).
Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).
Mather, "Establishment and characterization of two distinct mouse testicular epithelial cell lines," Biol Reprod. 23(1):243-52 (1980).
Matsumoto et al., "Rescue of severe infantile hypophosphatasia mice by AAV-mediated sustained expression of soluble alkaline phosphatase," Hum Gene Ther. 22(11):1355-64 (2011).
Mayer, "Immunoglobulins: Structure and Function," Microbiology and Immunology On-line, University of South Carolina School of Medicine, <http://pathmicro.med.sc.edu/mayer/IgStruct2000.htm> (2009) (12 pages).
McKiernan et al., "Clinical and radiographic findings in adults with persistent hypophosphatasemia," J Bone Miner Res. 29(7):1651-60 (2014).
Mericq et al., "Regulation of fetal rat bone growth by C-type natriuretic peptide and cGMP," Pediatr Res. 47(2):189-193 (2000) (9 pages).
Meyer, "Can biological calcification occur in the presence of pyrophosphate?" Arch Biochem Biophys. 231:1-8 (1984).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Millán, "Mammalian Alkaline Phosphatases: From Biology to Applications in Medicine and Biotechnology," Wiley-VCH Verlag GmbH & Co., Weinheim, Germany (2006) (324 pages).
Millán et al., "Alkaline phosphatase and hypophosphatasia," Calcif Tissue Int. 98(4):398-416 (2016).
Millán et al., "Enzyme replacement therapy for murine hypophosphatasia," J Bone Miner Res. 23(6): 777-87 (2008).
Millán et al., "Hypophosphatasia—pathophysiology and treatment," available in PMC Sep. 22, 2014, published in final edited form as: Actual Osteol. 8(3):164-182 (2012) (21 pages).
Millán, "The Mammalian alkaline phosphatases: From Biology to Applications in Medicine and Biotechnology," Wiley-VCH Verlag, 107-185 (2006).
Miyazawa et al., "Cyclic GMP-dependent protein kinase II plays a critical role in C-type natriuretic peptide-mediated endochondral ossification," Endocrinology. 143(9):3604-3610 (2002).
Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).
Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Mornet et al., "Structural evidence for a functional role of human tissue nonspecific alkaline phosphatase in bone mineralization," J Biol Chem. 276(33):31171-8 (2001).
Mornet, "Hypophosphatasia," Metabolism. 82:142-155; DOI: 10.1016/j.metabol.2017.08.013 (2018) (30 pages).
Mornet, "Hypophosphatasia," Orphanet J Rare Dis. 2:(40) (2007) (8 pages).
Mornet, "Molecular genetics of hypophosphatasia and phenotype-genotype correlations," Subcell Biochem. 76:25-43 (2015).
Morris et al., "Immunolocalization of alkaline phosphatase in osteoblasts and matrix vesicles of human fetal bone," Bone Miner. 19:287-298 (1992).
Morrow, "Expensive new biologic helps children fight hypophosphatasia," Manag Care. 24(12) (2015) (7 pages).
Moss et al., "Association of inorganic-pyrophosphatase activity with human alkaline-phosphatase preparations," Biochem J. 102:53-57 (1967).
Murray, "Lectin-specific targeting of lysosomal enzymes to reticuloendothelial cells," Methods Enzymol. 149:25-42 (1987).
Murshed et al., "Unique coexpression in osteoblasts of broadly expressed genes accounts for the spatial restriction of ECM mineralization to bone," Genes Dev. 19:1093-1104 (2005).
Nahabet et al., "Postnatal Pancraniosynostosis in a Patient With Infantile Hypophosphatasia," Cleft Palate Craniofac J. 53(6):741-4 (2016).

(56) References Cited

OTHER PUBLICATIONS

Nakao et al., "The pharmacokinetics of alpha-human atrial natriuretic polypeptide in healthy subjects," Eur J Clin Pharmacol. 31:101-103 (1986).
Narisawa et al., "Abnormal vitamin B6 metabolism in alkaline phosphatase knock-out mice causes multiple abnormalities, but not the impaired bone mineralization," J Pathol. 193:125-133 (2001).
Narisawa et al., "Inactivation of two mouse alkaline phosphatase genes and establishment of a model of infantile hypophosphatasia," Dev Dyn. 208:432-446 (1997).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
NCBI Protein Database Accession No. AAC33858. Retrieved on Apr. 16, 2013 (1 page).
NCBI Protein Database Accession No. AAF64516. Retrieved on Apr. 16, 2013 (2 pages).
NCBI Protein Database Accession No. AAH21289. Retrieved on Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI18209. Retrieved on Apr. 17, 2013 (2 pages).
NCBI Protein Database Accession No. AAI26166. Retrieved on Apr. 16, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798, Retrieved on Apr. 17, 2013 (2 pages).
NCBI Protein Database Accession No. NP_001622. Retrieved on Apr. 16, 2013 (3 pages).
NCBI Protein Database Accession No. NP_001623. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_112603. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09242. Retrieved on Apr. 16, 2013 (6 pages).
NCBI Protein Database Accession No. P09487. Retrieved on Apr. 16, 2013 (4 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q6PYX1. Retrieved on Oct. 15, 2013 (2 pages).
NCBI Protein Database Accession No. Q9N0V0. Retrieved on Apr. 16, 2013 (1 page).
NCBI Protein Database Accession No. XP_001109717. Retrieved on Apr. 17, 2013 (1 page).
Ngo et al., Chapter 14: Computational Complexity, Protein Structure Prediction, and the Levinthal Paradox. *The Protein Folding Problem and Tertiary Structure Prediction*. Merz et al. (eds.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Nosjean et al., "Human tissue non-specific alkaline phosphatases: sugar-moiety-induced enzymic and antigenic modulations and genetic aspects," Biochem J. 321:297-303 (1997).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Office Action for U.S. Appl. No. 11/111,664, dated Dec. 4, 2008 (7 pages).
Office Action for U.S. Appl. No. 11/111,664, dated May 14, 2008 (8 pages).
Office Action for U.S. Appl. No. 11/111,664, dated Oct. 4, 2007 (11 pages).
Office Action for U.S. Appl. No. 11/484,870, dated Aug. 11, 2009 (15 pages).
Office Action for U.S. Appl. No. 11/484,870, dated Feb. 2, 2009 (16 pages).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Jun. 25, 2008 (16 pages).
Office Action for U.S. Appl. No. 11/484,870, dated Oct. 1, 2007 (12 pages).
Office Action for U.S. Appl. No. 12/405,920, dated Aug. 9, 2010 (7 pages).
Office Action for U.S. Appl. No. 12/405,920, dated Dec. 17, 2009 (14 pages).
Office Action for U.S. Appl. No. 12/793,517, dated Aug. 16, 2010 (9 pages).
Office Action for U.S. Appl. No. 13/071,445, dated Feb. 6, 2012 (12 pages).
Office Action for U.S. Appl. No. 13/071,445, dated May 25, 2012 (14 pages).
Official Action for Japanese Application No. 2013-544989, dated Oct. 27, 2015 (3 pages).
Official Notification and Search Report for Eurasian Patent Application No. 201291138, dated May 17, 2013 (3 pages).
Oikawa et al., "Enzyme replacement therapy on hypophosphatasia mouse model," J Inherit Metab Dis. 37(2):309-17 (2013).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Orimo, "Pathophysiology of hypophosphatasia and the potential role of asfotase alfa," Ther Clin Risk Manag. 12:777-86 (2016).
Orimo, "The mechanism of mineralization and the role of alkaline phosphatase in health and disease," J Nippon Med Sch. 77(1):4-12 (2010).
Padidela et al., "Enzyme-replacement therapy in life-threatening perinatal hypophosphatasia in a premature infant," Endocrine Abstracts. 33:p. 9 (2013) (1 page).
Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Panesar, "Hypophosphatasia: a rare disorder," US Pharm. 42(5) (2017) (8 pages).

(56) References Cited

OTHER PUBLICATIONS

Park et al., "Ex vivo assessment of contractility, fatigability and alternans in isolated skeletal muscles," J Vis Exp. 69:e4198 (2012) (8 pages).
Park et al., "First Korean case of infantile hypophosphatasia with novel mutation in ALPL and literature review," Ann Clin Lab Sci. 46(3):302-7 (2016).
Patti et al., "Critical Residues in the Ligand-binding Site of the *Staphylococcus aureus* Collagen-binding Adhesin (MSCRAMM)," J Biol Chem. 270(20):12005-12011 (1995).
Pedersen et al., "Removal of N-terminal polyhistidine tags from recombinant proteins using engineered aminopeptidases," Protein Expr Purif. 15(3):389-400 (1999).
Pfeifer et al., "Intestinal secretory defects and dwarfism in mice lacking cGMP-dependent protein kinase II," Science. 274:2082-2086 (1996).
Phillips et al., "A modified performance-oriented mobility assessment tool for assessing clinically relevant gait impairments and change in children with hypophosphatasia: development and validation," Bone Abstracts. 4: p. 136 (2015) (2 pages).
Phillips et al., "Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, Mar. 5-8, San Diego, California. Poster Abstract FRI-224 (2015) (1 page).
Phillips et al., "Gait assessment in children with childhood hypophosphatasia: impairments in muscle strength and physical function," The Endocrine Society's 97th Annual Meeting & Expo, Mar. 5-8, San Diego, California (2015) (2 pages).
Phillips et al., "Physical therapy management of infants and children with hypophosphatasia," Mol Genet Metab. 119(1-2):14-9 (2016).
Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).
Potter et al., "Natriuretic peptides, their receptors, and cyclic guanosine monophosphate-dependent signaling functions," Endocr Rev. 27(1):47-72 (2006).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Ratner, "Alexion pays big for Synageva's rare disease drug candidate," Nat Biotechnol. 33(7):679 (2015).
Remde et al., "Successful asfotase alfa treatment in an adult dialysis patient with childhood-onset hypophosphatasia," J Endoc Soc. 1(9):1188-93 (2017).
Reply Brief as Filed in U.S. Appl. No. 12/638,527, dated Apr. 22, 2016 (4 pages).
Reply to Final Office Action for U.S. Appl. No. 13/071,445, dated Oct. 25, 2012 (14 pages).
Reply to Office Action for U.S. Appl. No. 11/111,664, dated Sep. 10, 2008 (32 pages).
Restriction Requirement for U.S. Appl. No. 12/599,679, dated Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Rowe et al., "MEPE, a new gene expressed in bone marrow and tumors causing osteomalacia," Genomics. 67:54-68 (2000).

Russell et al., "Inorganic pyrophosphate in plasma in normal persons and in patients with hypophosphatasia, osteogenesis imperfecta, and other disorders of bone," J Clin Invest. 50:961-969 (1971).
Saglam et al., "Clinical and genetic findings of Turkish hypophosphatasia cases," J Clin Res Pediatr Endocrinol. 9(3):229-236 (2017).
Salih et al., "Identification of the phosphorylated sites of metabolically 32P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Saraff et al., "A diagnostic algorithm for children with low alkaline phosphatase activities: lessons learned from laboratory screening for hypophosphatasia," J Pediatr. 172:181-6 (2016) (7 pages).
Sather, "Case Study: 3 year old female with hypophosphatasia, treated with asfotase alfa replacement," J Pediatr Nurs. 34:104 (Abstract 008) (2017).
Sawai et al., "Severe perinatal hypophosphatasia due to homozygous deletion of T at nucleotide 1559 in the tissue nonspecific alkaline phosphatase gene," Prenat Diagn. 23(9):743-6 (2003).
Schindeler et al., "Modeling bone morphogenetic protein and bisphosphonate combination therapy in wild-type and Nf1 haploinsufficient mice," J Orthop Res. 26(1):65-74 (2008).
Schmidt et al., "Clinical, radiographic and biochemical characteristics of adult hypophosphatasia," Osteoporos Int. 28(9):2653-2662 (2017).
Schmidt et al., "Hypophosphatasia: What is currently available for treatment?" Internist (Berl). 57(12):1145-1154 (2016) (Article in German) (English abstract).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL (1 page).
Sekido et al., "Novel drug delivery system to bone using acidic oligopeptide: pharmacokinetic characteristics and pharmacological potential," J Drug Target. 9(2):111-21 (2001).
Shapiro et al., "Hypophosphatasia in adults: clinical assessment and treatment considerations," J Bone Miner Res. 32(10):1977-1980 (2017).
Sharom et al., "Glycosylphosphatidylinositol-anchored proteins: structure, function, and cleavage by phosphatidylinositol-specific phospholipase C," Biochem Cell Biol. 80:535-549 (2002).
Sheikh et al., "A newborn with no bones: neonatal hypophosphatasia with respiratory distress," J Pediatr. 188:306 (2017).
Shukla et al., "RNA interference and inhibition of MEK-ERK signaling prevent abnormal skeletal phenotypes in a mouse model of craniosynostosis," Nat Genet. 39(9):1145-1150 (2007).
Shull et al., "Enzyme replacement in a canine model of Hurler syndrome," Proc Natl Acad Sci USA. 91:12937-12941 (1994).
Siller et al., "Alkaline phosphatase: discovery and naming of our favorite enzyme," J Bone Miner Res. 33(2):362-4 (2018).
Simm et al., "Successful use of enzyme replacement therapy in infantile hypophosphatasia," J Paediatr Child Health. 53(9):925-926 (2017).
Siris et al., "Paget's disease of bone," Trends Endocrinol Metab. 2(6):207-12 (1991).
Skolnick et al., "From genes to protein structure and function: novel applications of computational approaches in the genomic era," Trends Biotechnol. 18(1):34-9 (2000).
Sotillo et al., "Signs and symptoms of hypophosphatasia," Dimensions of Dental Hygiene. 15(4):44-47 (2017) (6 pages).
Spears et al., "Deoxyuridylate effects on thymidylate synthase-5-fluorodeoxyuridylate-folate ternary complex formation," Biochem Pharmacol. 38(18):2985-2993 (1989).
Spentchian et al., "Severe hypophosphatasia: characterization of fifteen novel mutations in the ALPL gene," Hum Mutat. 22(1) (2003) (5 pages).

(56) References Cited

OTHER PUBLICATIONS

Srinivas et al., "Assessment of dose proportionality, absolute bioavailability, and immunogenicity response of CTLA4Ig (BMS-188667), a novel immunosuppressive agent, following subcutaneous and intravenous administration to rats," Pharmaceutical Res. 14(7):911-916 (1997).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Stec et al., "A revised mechanism for the alkaline phosphatase reaction involving three metal ions," J Mol Biol. 299(5):1303-11 (2000).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Suda et al., "C-type natriuretic peptide as an autocrine/paracrine regulator of osteoblast: evidence for possible presence of bone natriuretic peptide system," Biochem Biophys Res Commun. 223:1-6 (1996).
Sugano et al., "Successful gene therapy in utero for lethal murine hypophosphatasia," Hum Gene Ther. 23(4):399-406 (2012).
Supplementary European Search Report for European Application No. 05739065, dated Dec. 2, 2008 (3 pages).
Extended European Search Report for European Application No. 08757088, dated Jun. 7, 2010 (5 pages).
Supplementary European Search Report for European Patent Application No. 11853820.6, dated Mar. 25, 2014 (3 pages).
Symersky et al., "Structure of the collagen-binding domain from a *Staphylococcus aureus* adhesin," Nat Struct Biol. 4(10):833-838 (1997).
Takahashi et al., "Parental serum alkaline phosphatase activity as an auxiliary tool for prenatal diagnosis of hypophosphatasia," Prenat Diagn. 37(5):491-6 (2017).
Takano et al., "Molecular evolution of shark C-type natriuretic peptides," Zoolog Sci. 11:451-454 (1994).
Taketani et al., "Clinical and genetic aspects of hypophosphatasia in Japanese patients," Arch Dis Child. 99(3):211-5 (2014) (6 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Takinami et al., "The mutant (F310L and V365I) tissue-nonspecific alkaline phosphatase gene from hypophosphatasia," J Med Dent Sci. 51(1):67-74 (2004).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319:171-178 (2008).
Tenorio et al., "Molecular and clinical analysis of ALPL in a cohort of patients with suspicion of hypophosphatasia," Am J Med Genet A. 173(3):601-10 (2017).
Tomatsu, Declaration Under 37 C.F.R. § 1.132 for U.S. Appl. No. 11/484,870, dated Jun. 1, 2009 (3 pages).
Tomatsu, Declaration Under 37 C.F.R. § 1.132 for U.S. Appl. No. 11/484,870, dated Nov. 27, 2007 (2 pages).
Tsiantouli et al., "Hypophosphatasia," Rev Med Suisse. 13(559):855-8 (2017) (Article in French) (English Abstract Included).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Tye et al., "Delineation of the hydroxyapatite-nucleating domains of bone sialoprotein," J Biol Chem. 278(10):7949-7955 (2003).
Uludag et al., "Bone affinity of a bisphosphonate-conjugated protein in vivo," Biotechnol Prog. 16(6):1115-8 (2000).
UniProtKB Accession No. P01857. Retrieved May 2, 2018 (13 pages).
UniProtKB Accession No. P05186. Retrieved May 2, 2018 (19 pages).
Urlaub et al., "Deletion of the diploid dihydrofolate reductase locus from cultured mammalian cells," Cell. 33:405-412 (1983).
Urlaub et al., "Isolation of Chinese hamster cell mutants deficient in dihydrofolate reductase activity," Proc Natl Acad Sci U S A. 77(7):4216-20 (1980).
Wang et al., "A mouse model for achondroplasia produced by targeting fibroblast growth factor receptor 3," Proc Natl Acad Sci USA. 96:4455-4460 (1999).
Wang et al., "Current concepts in odontohypophosphatasia form of hypophosphatasia and report of two cases," BMC Oral Health. 16(1):70 (2016) (8 pages).
Wang et al., "Mice lacking Nf1 in osteochondroprogenitor cells display skeletal dysplasia similar to patients with neurofibromatosis type 1," Hum Mol Genet. 20(20):3910-3924 (2011).
Wang et al., "Structure-based chemical modification strategy for enzyme replacement treatment of phenylketonuria," Mol Genet Metab. 86:134-140 (2005).
Waymire et al., "Mice lacking tissue non-specific alkaline phosphatase die from seizures due to defective metabolism of vitamin B-6," Nat Genet. 11(1):45-51 (1995).
Weber et al., "Burden of disease in adult patients with hypophosphatasia: Results from two patient-reported surveys," Metabolism. 65(10):1522-30 (2016).
Weinberg, "An overview of infliximab, etanercept, efalizumab, and alefacept as biologic therapy for psoriasis," Clin Ther. 25(10):2487-505 (2003).
Weiss et al., "A missense mutation in the human liver/bone/kidney alkaline phosphatase gene causing a lethal form of hypophosphatasia," Proc Natl Acad Sci USA. 85:7666-7669 (1988).
Weiss et al., "Isolation and characterization of a cDNA encoding a human liver/bone/kidney-type alkaline phosphatase," Proc Natl Acad Sci USA. 83(19):7182-6 (1986) (6 pages).
Weiss et al., "Structure of the human liver/bone/kidney alkaline phosphatase gene," J Biol Chem. 263(24):12002-10 (1988).
Weninger et al., "Biochemical and morphological effects of human hepatic alkaline phosphatase in a neonate with hypophosphatasia," Acta Paediatr Scand. Suppl. 360:154-160 (1989).
Whyte, Chapter 207: Hypophosphatasia. *The Online Metabolic and Molecular Bases for Inherited Disease.* McGraw-Hill Book Company, Valle et al. (eds.) (2001) (41 pages).
Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).
Whyte et al., "Asfotase alfa therapy for children with hypophosphatasia," JCI Insight. 1(9):e85971 (2016) (11 pages).
Whyte et al., "Asfotase alfa treatment improves survival for perinatal and infantile hypophosphatasia," J Clin Endocrinol Metab. 101(1):334-42 (2016) (17 pages).
Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).
Whyte et al., "Enzyme-replacement therapy in life-threatening hypophosphatasia," N Engl J Med. 366(10):904-13 (2012).
Whyte, Chapter 18: Heritable Forms of Rickets and Osteomalacia. *Connective Tissue and Its Heritable Disorders.* Wiley-Liss, Inc., eds. R.M. Royce and B. Steinmann, 765-87 (2002).
Whyte, "Hypophosphatasia," in The Metabolic and Molecular Bases of Inherited Disease (8th ed.), pp. 5313-5329, 2001 (McGraw-Hill Book Company) (epub pp. 1-41).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012).
Whyte et al., "Hypophosphatasia: natural history study of 101 affected children investigated at one research center," Bone. 93:125-138 (2016).

(56) References Cited

OTHER PUBLICATIONS

Whyte et al., "Hypophosphatasia: validation and expansion of the clinical nosology for children from 25 years experience with 173 pediatric patients," Bone. 75:229-39 (2015).
Whyte et al., "Infantile hypophosphatasia: enzyme replacement therapy by intravenous infusion of alkaline phosphatase-rich plasma from patients with Paget bone disease," J Pediatr. 101(3):379-86 (1982).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Whyte et al., "Markedly increased circulating pyridoxal-5'-phosphate levels in hypophosphatasia," J Clin Invest. 76:752-756 (1985).
Whyte et al., "Marrow cell transplantation for infantile hypophosphatasia," J Bone Miner Res. 18(4):624-36 (2003).
Whyte, "Hypophosphatasia—aetiology, nosology, pathogenesis, diagnosis and treatment," Nat Rev Endocrinol. 12(4):233-46 (2016).
Whyte, "Hypophosphatasia and the role of alkaline phosphatase in skeletal mineralization," Endocr Rev. 15(4):439-461 (1994).
Whyte, "Hypophosphatasia: an overview for 2017," Bone. 102:15-25 (2017).
Whyte, "Hypophosphatasia: enzyme replacement therapy brings new opportunities and new challenges," J Bone Miner Res. 32(4):667-675 (2017).
Whyte, "Physiological role of alkaline phosphatase explored in hypophosphatasia," Ann N Y Acad Sci. 1192:190-200 (2010).
Whyte, "Chapter 70: Hypophosphatasia: Nature's window on alkaline phosphatase function in man," *Principles of Bone Biology*, 2nd ed., Bilezikian, Raisz, and Rodan. 2:1229-1248 (2002).
Wickramasinghe et al., "A case of hypophosphatasia," Ceylon Med J. 48(3):94-5 (2003).
Williams et al., "Solute transport in growth plate cartilage: In vitro and in vivo," Biophys J. 93(3):1039-1050 (2007).
Wroblewski et al., "Pharmacokinetics, metabolic stability, and subcutaneous bioavailability of a genetically engineered analog of DcR3, FLINT [DcR3(R218Q)], in cynomolgus monkeys and mice," Drug Metab Dispos. 31(4):502-507 (2003).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yamamoto et al., "A successful treatment with pyridoxal phosphate for West syndrome in hypophosphatasia," Pediatr Neurol. 30(3):216-8 (2004).
Yamamoto et al., "Long term phenotypic correction of severe infantile hypophosphatasia in a mouse model by neonatal injection of lentiviral vector," Mol Ther. 17:S67-S68, Abstract 171 (2009) (2 pages).
Yamamoto et al., "Prolonged survival and phenotypic correction of Akp2$^{-/-}$ hypophosphatasia mice by lentiviral gene therapy," J Bone Miner Res. 26(1):135-42 (2011).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Overexpression of CNP in chondrocytes rescues achondroplasia through a MAPK-dependent pathway," Nat Med. 10(1):80-86 (2004).
Yasoda et al., "Systemic administration of C-type natriuretic peptide as a novel therapeutic strategy for skeletal dysplasias," Endocrinology. 150(7):3138-3144 (2009).
Yoder et al., "Reduced ability of C-type natriuretic peptide (CNP) to activate natriuretic peptide receptor B (NPR-B) causes dwarfism in lbab$^{-/-}$ mice," Peptides. 29(9):1575-1581 (2008).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Zierhut et al., "Population PK-PD model for Fc-osteoprotegerin in healthy postmenopausal women," J Pharmacokinet Pharmacodyn. 35:379-399 (2008).
Zurutuza et al., "Correlations of genotype and phenotype in hypophosphatasia," Hum Mol Genet. 8(6):1039-1046 (1999).
Extended European Search Report for European Application No. 18173111.8, dated Aug. 21, 2018 (9 pages).
National Institute for Health and Care Excellence, "Highly Specialised Technology Evaluation: Asfotase alfa for treating paediatric-onset hypophosphatasia [ID 758]," Oct. 21, 2015, <https://www.nice.org.uk/guidance/hst6/documents/committee-papers-8> (99 pages).
Tomazos et al., "Determination of the Minimal Clinically Important Difference in the Six-Minute Walk Test for Patients with Hypophosphatasia," 55th Annual European Society for Paediatric Endocrinology Meeting, Sep. 10-12, Paris, France. 86, Abstract FC2.5, <http://abstracts.eurospe.org/hrp/0086/hrp0086FC2.5.htm> (2016) (4 pages).
International Search Report and Written Opinion for International Application No. PCT/US18/26868, dated Sep. 7, 2018 (30 pages).
International Preliminary Report on Patentability for International Patent Application No. PCT/US2016/049983, dated Sep. 11, 2018 (9 pages).
Sequence 4, U.S. Appl. No. 12/599,679, Retrieved Nov. 17, 2018 (2 pages).
Agochukwu et al., "Hearing loss in syndromic craniosynostoses: introduction and consideration of mechanisms," available in PMC Aug. 13, 2014, published in final edited form as: Am J Audiol. 23(2): 135-41 (2014) (13 pages).
Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).
Barcia et al., "Infantile hypophosphatasia: treatment options to control hypercalcemia, hypercalciuria, and chronic bone demineralization," J Pediatr. 130(5):825-8 (1997).
Barvencik et al., "Skeletal mineralization defects in adult hypophosphatasia—a clinical and histological analysis," Osteoporosis Int. 22(10):2667-75 (2011).
Baumgartner-Sigl et al., "Pyridoxine-responsive seizures as the first symptom of infantile hypophosphatasia caused by two novel missense mutations (c.677T>C, p.M226T; c.1112C>T, p.T3711) of the tissue-nonspecific alkaline phosphatase gene," Bone. 40(6):1655-61 (2007).
Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).
Boulet et al., "A population-based study of craniosynostosis in metropolitan Atlanta, 1989-2003," Am J Med Genet A. 146A(8): 984-91 (2008).
Chan et al., "Endoscope-assisted versus open repair of craniosynostosis: a comparison of perioperative cost and risk," J Craniofac Surg. 24(1): 170-4 (2013).
Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Clarke, "Normal bone anatomy and physiology," Clin J Am Soc Nephrol. 3 Suppl 3: S131-9 (2008).
Colantonio et al., "Closing the gaps in pediatric laboratory reference intervals: a CALIPER database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).

(56) References Cited

OTHER PUBLICATIONS

Czerwinski et al., "Major morbidity and mortality rates in craniofacial surgery: an analysis of 8101 major procedures," Plast Reconstr Surg. 126(1):181-6 (2010).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugia. 19(6):509-29 (2008).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliova et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guanabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-159 (2013).
Hwang et al., "Update of diagnostic evaluation of craniosynostosis with a focus on pediatric systematic evaluation and genetic studies," J Korean Neurosurg Soc. 59(3):214-8 (2016).
Johnson et al., "Craniosynostosis," Eur J Hum Genet. 19(4):369-76 (2011).
Kabbani et al., "Craniosynostosis," Am Fam Physician. 69(12):2863-70 (2004).
Katsianou et al., "Signaling mechanisms implicated in cranial sutures pathophysiology: craniosynostosis," BBA Clin. 6:165-76 (2016).
Khanna et al., "Pictorial essay: The many faces of craniosynostosis," retrieved from <www.ncbi.nlm.nih.gov/pmc/articles/PMC3056371/> on Sep. 10, 2017, Indian J Radiol Imaging. 21(1):49-56 (2011) (8 pages).
Kim et al., "Craniosynostosis: Updates in radiologic diagnosis," J Korean Neurosurg Soc. 59(3):219-26 (2016).
Kozlowski et al., "Hypophosphatasia. Review of 24 Cases," Pediatr Radiol. 5(2):103-17 (1976).
Krakow et al., "Clinical and radiographic delineation of Bent Bone Dysplasia-FGFR2 type or Bent Bone Dysplasia with Distinctive Clavicles and Angel-shaped Phalanges," Am J Med Genet A. 170(10):2652-61 (2016).
Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).
Millán, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Reginato et al., "Musculoskeletal manifestations of osteomalacia and rickets," Best Pract Res Clin Rheumatol. 17(6):1063-80 (2003).
Rodgers et al., "Spring assisted cranioplasty for the correction of non-syndromic scaphocephaly: a quantitative analysis of 100 consecutive cases," Plast Reconstr Surg. 140(1):125-34 (2017).
Rottgers et al., "Outcomes of endoscopic suturectomy with post-operative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-93 (1988) (12 pages).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Watanabe et al., "Prevalence of c. 1559delT in ALPL, a common mutation resulting in the perinatal (lethal) form of hypophosphatasia in Japanese and effects of the mutation on heterozygous carriers," J Hum Genet. 56(2):166-8 (2011).
Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Adult hypophosphatasia treated with teriparatide," J Clin Endocrinol Metab. 92(4):1203-8 (2007).
Whyte et al., "Rickets and osteomalacia," Medicine. 37(9):483-8 (2009).
Zaleckas et al., "Diagnosis and treatment of craniosynostosis: Vilnius team experience," Acta Med Litu. 22(2):111-21 (2015).
Anderson, "Mechanism of Mineral Formation in Bone," *Pathology Reviews*. Emanuel Rubin and Ivan Damjanov (eds.), 13-23 (1990).
Whyte, Chapter 73: Hypophosphatasia: Nature's Window on Alkaline Phosphatase Function in Humans, *Principles of Bone Biology*, vol. 1, Third Edition. John P. Bilezikian, Lawrence G. Raisz and T. John Martin (eds.), 1573-98 (2008).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Rockman-Greenberg et al., "Hypophosphatasia: Enzyme Replacement with ENB-0040, a Bone-Targeted Human Recombinant Tissue

(56) References Cited

OTHER PUBLICATIONS

Nonspecific Alkaline Phosphatase (TNSALP) Fusion Protein," American College of Medical Genetics, 16th Annual Clinical Genetics Meeting, Mar. 25-29, Tampa, Florida (2009) (1 page).

Simmons, "Best Practices In: Recognizing and Diagnosing Hypophosphatasia," Clinical Endocrinology News. <https://www.mdedge.com/sites/default/files/issues/articles/Alexion_10_11_Final_Web.pdf>, published Sep. 30, 2013, retrieved on Mar. 27, 2019 (8 pages).

Weber et al., "Burden of disease in children with hypophosphatasia: results from patient-reported surveys," 7th International Conference on Children's Bone Health, Jun. 27-30, Salzburg, Austria. *Bone Abstracts*. 4: p. 119 (2015) (3 pages).

Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).

Whyte et al., "Hypophosphatasia: A Retrospective Natural History Study of the Severe Perinatal and Infantile Forms," 2014 European Calcified Tissue Society Congress, May 17-20, Prague, Czech Republic. Poster p. 364 (2014) (1 page).

Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).

Stoll et al., "Severe hypophosphatasia due to mutations in the tissue-nonspecific alkaline phosphatase (TNSALP) gene," Genet Couns. 13(3):289-95 (2002).

Mornet, "Hypophosphatasia," Best Pract Res Clin Rheumatol. 22(1):113-27 (2008).

Kajdic et al., "Craniosynostosis—Recognition, clinical characteristics, and treatment," Bosn J Basic Med Sci. 18(2):110-6 (2018).

Dortschy et al., "Bevölkerungsbezogene verteilungswerte ausgewählter laborparameter aus der studie zur gesundheit von kindern und jugendlichen in Deutschland (KiGGS)," Robert Koch Institute (2009) (136 pages).

Communication pursuant to Rule 164(2)(b) and Article 94(3) EPC for European Patent Application 16707571.2, dated Feb. 26, 2019 (12 pages).

Fong et al., "Hypocalcemia: Updates in diagnosis and management for primary care," Can Fam Physician. 58(2):158-62 (2012).

Makras et al., "Medical treatment of Hypercalcaemia," Hormones. 8(2):83-95 (2009).

Di Rocco et al., "Craniosynostosis and hypophosphatasia," Arch Pediatr. 24(5S2):5S89-5S92 (2017).

Whyte et al., "Natural history of perinatal and infantile hypophosphatasia: a retrospective study," J Pediatr. 209:116-124.e4 (2019) (13 pages).

Leung et al., "Outcome of perinatal hypophosphatasia in manitoba mennonites: a retrospective cohort analysis," JIMP Rep. 11:73-78 (2013).

Taketani et al., Chapter 9: Hypophosphatasia. *Human Pathobiochemistry*. T. Oohashi et al. (eds.), 91-100 (2019).

Morrison et al., "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).

Whyte et al., "Asfotase alfa for infants and young children with hypophosphatasia: 7 year outcomes of a single-arm, open-label, phase 2 extension trial," Lancet Diabetes Endocrinol. 7(2):93-105 (2019) (52 pages).

Mornet, "The tissue nonspecific alkaline phosphatase gene mutations database," <http://www.sesep.uvsq.fr/03_hypo_mutations.php>, last updated Nov. 28, 2019 (14 pages).

Hancarova et al., "Hypophosphatasia due to uniparental disomy," Bone. 81:765-766 (2015).

Carden et al., "Tracheomalacia and tracheobronchomalacia in children and adults: an in-depth review," Chest. 127(3):984-1005 (2005).

Murgu et al., "Tracheobronchomalacia and excessive dynamic airway collapse," Respirology. 11(4):388-406 (2006).

Whyte et al., "Hypophosphatasia (HPP) in Children: Enzyme Replacement Therapy (EzRT) Using Bone-Targeted, Tissue-Nonspecific Alkaline Phosphatase (TNSALP)," 39th Annual Meeting of the Child-Neurology-Society. 68(Suppl 14):S70 Abstract WIP-28 (2010).

Abrams et al., "Calcium and Vitamin D Requirements of Enterally Fed Preterm Infants," Pediatrics. 131(5): e1676-e1683 (2013) (9 pages).

Kishnani et al., "Hypophosphatasia: enzyme replacement therapy (ENB-0040) decreases TNSALP substrate accumulation and improves functional outcome in affected adolescents and adults," Endocrine Society's 15th International & 14th European Congress of Endocrinology, May 5-9, Florence, Italy. Abstract OC8.1 (2012) (4 pages).

Wang et al., "The effects of tissue-non-specific alkaline phosphatase gene therapy on craniosynostosis and craniofacial morphology in the FGFR2C342Y/+ mouse model of Crouzon craniosynostosis," Orthod Craniofac Res. 18 Suppl 1:196-206 (2015).

```
atggaagcagaaacagggagcagcgtggagactggaaagaaggccaacagaggcactcgaattgccctgg
tcgtgtttgtcctgacagtgatcgctcaacaaacaaccagtcaaggtctcttatccggagatgacgatga
cgatgacgatgacgatgactccggaagtctccaagctaaacaggagtactgcctgaagccagaatgcatc
gaagcggctgctgccatcttaagtaaagtaaatctgtctgtggatccttgtgataatttcttccggttcg
cttgtgatggctggataagcaataatccaattcccgaagatatgccaagctatggggtttatccttggct
gagacataatgttgacctcaagttgaaggaacttttggagaaatcaatcagtagaaggcgggacaccgaa
gccatacagaaagccaaaatcctttattcatcctgcatgaatgagaaagcgattgaaaagcagatgcca
agccactgctacacatcctacggcattcacctttccgctggcccgtgcttgaatctaatattggccctga
aggggtttggtcagagagaaagttcagccttctgcagacacttgcaacgtttcgtggtcaatacagcaat
tctgtgttcatccgtttgtatgtgtccctgatgacaaagcatccaatgaacatatcttgaagctggacc
aagcaacactctccctggccgtgagggaagactaccttgataacagtacagaagccaagtcttatcggga
tgcccctttacaagttcatggtggatactgccgtgcttttaggagctaacagttccagagcagagcatgac
atgaagtcagtgctcagattggaaattaagatagctgagataatgattccacatgaaaaccgaaccagcg
aggccatgtacaacaaaatgaacatttctgaactgagtgctatgattccccagttcgactggctgggcta
catcaagaaggtcattgacaccagactctaccccatctgaaagacatcagcccctccgagaatgtggtg
gtccgcgtcccgcagtactttaaagatttgtttaggatattagggtctgagagaaagaagaccattgcca
actatttggtgtggagaatggtttattccagaattccaaaccttagcaggcgctttcagtatagatggct
ggaattctcaagggtaatccaggggaccacaactttgctgcctcaatgggacaaatgtgtaaactttatt
gaaagtgccctcccttatgttgttggaaagatgtttgtagatgtgtacttccaggaagataagaaggaaa
tgatggaggaattggttgagggcgttcgctgggcctttattgacatgctagagaaagaaaatgagtggat
ggatgcaggaacgaaaaggaaagccaaagaaaggcgagagctgttttggcaaaagttggctatccagag
tttataatgaatgatactcatgttaatgaagacctcaaagctatcaagttttcagaagccgactactttg
gcaacgtcctacaaactcgcaagtatttagcacagtctgatttcttctggctaagaaaagccgttccaaa
aacagagtggtttacaaatccgacgactgtcaatgccttctacagtgcatccaccaaccagatccgattt
ccagcaggagagctccagaagcctttcttttggggaacagaatatcctcgatctctgagttatggtgcta
taggagtaattgtcggacatgaatttacacatggatttgataataatggtagaaaatatgataaaaatgg
aaacctggatccttggtggtctactgaatcagaagaaaagtttaaggaaaaaacaaatgcatgattaac
cagtatagcaactattattggaagaaagctggcttaaatgtcaaggggaagaggaccctgggagaaaata
ttgctgataatggaggcctgcgggaagcttttagggcttacaggaaatggataaatgacagaaggcaggg
acttgaggagcctcttctaccaggcatcacattcaccaacaaccagctcttcttcctgagttatgctcat
gtgaggtgcaattcctacagaccagaagctgcccgagaacaagtccaaattggtgctcacagtcccctc
agtttagggtcaatggtgcaattagtaactttgaagaattccagaaagcttttaactgtccacccaattc
cacgatgaacagaggcatggactcctgccgactctggtag
```

Figure 7

MEAETGSSVETGKKANRGTRIALVVFVLTVIAQQTTSQGLLSGDDDDDDDDDSGSLQAKQEYCLKPECI
EAAAAILSKVNLSVDPCDNFFRFACDGWISNNPIPEDMPSYGVYPWLRHNVDLKLKELLEKSISRRRDTE
AIQKAKILYSSCMNEKAIEKADAKPLLHILRHSPFRWPVLESNIGPEGVWSERKFSLLQTLATFRGQYSN
SVFIRLYVSPDDKASNEHILKLDQATLSLAVREDYLDNSTEAKSYRDALYKFMVDTAVLLGANSSRAEHD
MKSVLRLEIKIAEIMIPHENRTSEAMYNKMNISELSAMIPQFDWLGYIKKVIDTRLYPHLKDISPSENVV
VRVPQYFKDLFRILGSERKKTIANYLVWRMVYSRIPNLSRRFQYRWLEFSRVIQGTTTLLPQWDKCVNFI
ESALPYVVGKMFVDVYFQEDKKEMMEELVEGVRWAFIDMLEKENEWMDAGTKRKAKEKARAVLAKVGYPE
FIMNDTHVNEDLKAIKFSEADYFGNVLQTRKYLAQSDFFWLRKAVPKTEWFTNPTTVNAFYSASTNQIRF
PAGELQKPFFWGTEYPRSLSYGAIGVIVGHEFTHGFDNNGRKYDKNGNLDPWWSTESEEKFKEKTKCMIN
QYSNYYWKKAGLNVKGKRTLGENIADNGGLREAFRAYRKWINDRRQGLEEPLLPGITFTNNQLFFLSYAH
VRCNSYRPEAAREQVQIGAHSPPQFRVNGAISNFEEFQKAFNCPPNSTMNRGMDSCRLW

Figure 8

```
  1 MEAETGSSVE TGKKANRGTR IALVVFVGGT LVLGTILFLV SQGLLSLQAK QEYCLKPECI
 61 EAAAAILSKV NLSVDPCDNF FRFACDGWIS NNPIPEDMPS YGVYPWLRHN VDLKLKELLE
121 KSISRRRDTE AIQKAKILYS SCMNEKAIEK ADAKPLLHIL RHSPFRWPVL ESNIGPEGVW
181 SERKFSLLQT LATFRGQYSN SVFIRLYVSP DDKASNEHIL KLDQATLSLA VREDYLDNST
241 EAKSYRDALY KFMVDTAVLL GANSSRAEHD MKSVLRLEIK IAEIMIPHEN RTSEAMYNKM
301 NISELSAMIP QFDWLGYIKK VIDTRLYPHL KDISPSENVV VRVPQYFKDL FRILGSERKK
361 TIANYLVWRM VYSRIPNLSR RFQYRWLEFS RVIQGTTTLL PQWDKCVNFI ESALPYVVGK
421 MFVDVYFQED KKEMMEELVE GVRWAFIDML EKENEWMDAG TKRKAKEKAR AVLAKVGYPE
481 FIMNDTHVNE DLKAIKFSEA DYFGNVLQTR KYLAQSDFFW LRKAVPKTEW FTNPTTVNAF
541 YSASTNQIRF PAGELQKPFF WGTEYPRSLS YGAIGVIVGH EFTHGFDNNG RKYDKNGNLD
601 PWWSTESEEK FKEKTKCMIN QYSNYYWKKA GLNVKGKRTL GENIADNGGL REAFRAYRKW
661 INDRRQGLEE PLLPGITFTN NQLFFLSYAH VRCNSYRPEA AREQVQIGAH SPPQFRVNGA
721 ISNSEEFQKA FNCPPNSTMN RGMDSCRLW
```

Figure 10

```
SGDDDDDDDDDDSGSLQAKQEYCLKPECIEAAAAILSKVNLSVDPCDNFFRFACDGWISNNPIPEDMPSY
GVYPWLRHNVDLKLKELLEKSISRRRDTEAIQKAKILYSSCMNEKAIEKADAKPLLHILRHSPFRWPVLE
SNIGPEGVWSERKFSLLQTLATFRGQYSNSVFIRLYVSPDDKASNEHILKLDQATLSLAVREDYLDNSTE
AKSYRDALYKFMVDTAVLLGANSSRAEHDMKSVLRLEIKIAEIMIPHENRTSEAMYNKMNISELSAMIPQ
FDWLGYIKKVIDTRLYPHLKDISPSENVVVRVPQYFKDLFRILGSERKKTIANYLVWRMVYSRIPNLSRR
FQYRWLEFSRVIQGTTTLLPQWDKCVNFIESALPYVVGKMFVDVYFQEDKKEMMEELVEGVRWAFIDMLE
KENEWMDAGTKRKAKEKARAVLAKVGYPEFIMNDTHVNEDLKAIKFSEADYFGNVLQTRKYLAQSDFFWL
RKAVPKTEWFTNPTTVNAFYSASTNQIRFPAGELQKPFFWGTEYPRSLSYGAIGVIVGHEFTHGFDNNGR
KYDKNGNLDPWWSTESEEKFKEKTKCMINQYSNYYWKKAGLNVKGKRTLGENIADNGGLREAFRAYRKWI
NDRRQGLEEPLLPGITFTNNQLFFLSYAHVRCNSYRPEAAREQVQIGAHSPPQFRVNGAISNFEEFQKAF
NCPPNSTMNRGMDSCRLW
```

Figure 11

| | Protein construct | Specific activity (UAF/sec/µg) | Schematic representation |
|---|---|---|---|
| 1 | sPHEX | 12.3 | SLQAK... |
| 2 | Fc-sPHEX | 5.75 | TSDKTH... SLQAK... |
| 3 | pCDNA3-RSV-NL1furin-sPHEX | N/A | SVSLQAK... |
| 4 | D₁₀sPHEX | 12.0 | GDDDDDDDDDDSGSLQAK... |
| 5 | D₆sPHEX | 8.55 | SDDDDDDYVSLQAK... |

▨ : Represents the mutated transmembrane domain of PHEX.

■ : Represents the human IgG1 signal peptide.

▩ : Represents the human IgG1 heavy chain domains hinge, CH2 and CH3.

▧ : 1 N-terminal sequence with the furin cleavage site (RTVVKR|SV).

| : Furin cleavage site.

| : peptidase signal cleavage site

```
      BamHI
      ~~~~~
   1  GGATCCACCA TGATTTCACC ATTCTTAGTA CTGGCCATTG GCACCTGCCT TACTAACTCC TTAGTGCCAG
  71  AGAAAGAGAA AGACCCCAAG TACTGGCGAG ACCAAGCGCA AGAGACACTG AAATATGCCC TGGAGCTTCA
 141  GAAGCTCAAC ACCAACGTGG CTAAGAATGT CATCATGTTC CTGGGAGATG GGATGGGTGT CTCCACAGTG
 211  ACGGCTGCCC GCATCCTCAA GGGTCAGCTC CACCACAACC TGGGGAGGA GACCAGGCTG GAGATGGACA
 281  AGTTCCCCTT CGTGGCCCTC TCCAAGACGT ACAACACCAA TGCCCAGGTC CCTGACAGCG CCGGCACCGC
 351  CACCGCCTAC CTGTGTGGGG TGAAGGCCAA TGAGGGCACC GTGGGGGTAA GCGCAGCCAC TGAGCGTTCC
 421  CGGTGCAACA CCACCCAGGG GAACGAGGTC ACCTCCATCC TGCGCTGGGC CAAGGACGCT GGGAAATCTG
 491  TGGGCATTGT GACCACCACG AGAGTGAACC ATGCCACCCC CAGCGCCGCC TACGCCCACT CGGCTGACCG
 561  GGACTGGTAC TCAGACAACG AGATGCCCCC TGAGGCCTTG AGCCAGGGCT GTAAGGACAT CGCCTACCAG
 631  CTCATGCATA ACATCAGGGA CATTGACGTG ATCATGGGGG GTGGCCGGAA ATACATGTAC CCCAAGAATA
 701  AAACTGATGT GGAGTATGAG AGTGACGAGA AAGCCAGGGG CACGAGGCTG GACGCCTGG ACCTCGTTGA
 771  CACCTGGAAG AGCTTCAAAC CGGATACAA GCACTCCCAC TTCATCTGGA ACCGCACGGA ACTCCTGACC
 841  CTTGACCCCC ACAATGTGGA CTACCTATTG GGTCTCTTCG AGCCAGGGGA CATGCAGTAC GAGCTGAACA
 911  GGAACAACGT GACGGACCCG TCACTCTCCG AGATGGTGGT GGTGGCCATC CAGATCCTGC GGAAGAACCC
 981  CAAAGGCTTC TTCTTGCTGG TGGAAGGAGG CAGAATTGAC CACGGGCACC ATGAAGGAAA AGCCAAGCAG
1051  GCCCTGCATG AGGCGGTGGA GATGGACCGG GCCATCGGGC AGGCAGGCAG CTTGACCTCC TCGGAAGACA
1121  CTCTGACCGT GGTCACTGCG GACCATTCCC ACGTCTTCAC ATTTGGTGGA TACACCCCCC GTGGCAACTC
1191  TATCTTTGGT CTGGCCCCCA TGCTGAGTGA CACAGACAAG AAGCCCTTCA CTGCCATCCT GTATGGCAAT
1261  GGGCCTGGCT ACAAGGTGGT GGGCGGTGAA CGAGAGAATG TCTCCATGGT GGACTATGCT CACAACAACT
1331  ACCAGGCGCA GTCTGCTGTG CCCCTGCGCC ACGAGACCCA CGGCGGGGAG GACGTGGCCG TCTTCTCCAA
1401  GGGCCCCATG GCGCACCTGC TGCACGGCGT CCACGAGCAG AACTACGTCC CCCACGTGAT GGCGTATGCA
                                                                       XbaI
                                                                       ~~~~~~~
1471  GCCTGCATCG GGGCCAACCT CGGCCACTGT GCTCCTGCCA GCTCGTAGTC TAGA
```

B

```
   1  MISPFLVLAI GTCLTNSLVP EKEKDPKYWR DQAQETLKYA LELQKLNTNV
  51  AKNVIMFLGD GMGVSTVTAA RILKGQLHHN PGEETRLEMD KFPFVALSKT
 101  YNTNAQVPDS AGTATAYLCG VKANEGTVGV SAATERSRCN TTQGNEVTSI
 151  LRWAKDAGKS VGIVTTTRVN HATPSAAYAH SADRDWYSDN EMPPEALSQG
 201  CKDIAYQLMH NIRDIDVIMG GGRKYMYPKN KTDVEYESDE KARGTRLDGL
 251  DLVDTWKSFK PRYKHSHFIW NRTELLTLDP HNVDYLLGLF EPGDMQYELN
 301  RNNVTDPSLS EMVVVAIQIL RKNPKGFFLL VEGGRIDHGH HEGKAKQALH
 351  EAVEMDRAIG QAGSLTSSED TLTVVTADHS HVFTFGGYTP RGNSIFGLAP
 401  MLSDTDKKPF TAILYGNGPG YKVVGGEREN VSMVDYAHNN YQAQSAVPLR
 451  HETHGGEDVA VFSKGPMAHL LHGVHEQNYV PHVMAYAACI GANLGHCAPA
 501  SS
```

```
           BamHI
           ~~~~~~
     1  GGATCCACCA TGATTTCACC ATTCTTAGTA CTGGCCATTG GCACCTGCCT TACTAACTCC TTAGTGCCAG
    71  AGAAAGAGAA AGACCCCAAG TACTGGCGAG ACCAAGCGCA AGAGACACTG AAATATGCCC TGGAGCTTCA
   141  GAAGCTCAAC ACCAACGTGG CTAAGAATGT CATCATGTTC CTGGGAGATG GGATGGGTGT CTCCACAGTG
   211  ACGGCTGCCC GCATCCTCAA GGGTCAGCTC CACCACAACC TGGGGAGGA GACCAGGCTG GAGATGGACA
   281  AGTTCCCCTT CGTGGCCCTC TCCAAGACGT ACAACACCAA TGCCCAGGTC CCTGACAGCG CCGGCACCGC
   351  CACCGCCTAC CTGTGTGGGG TGAAGGCCAA TGAGGGCACC GTGGGGGTAA GCGCAGCCAC TGAGCGTTCC
   421  CGGTGCAACA CCACCCAGGG GAACGAGGTC ACCTCCATCC TGCGCTGGGC CAAGGACGCT GGGAAATCTG
   491  TGGGCATTGT GACCACCACG AGAGTGAACC ATGCCACCCC CAGCGCCGCC TACGCCCACT CGGCTGACCG
   561  GGACTGGTAC TCAGACAACG AGATGCCCCC TGAGGCCTTG AGCCAGGGCT GTAAGGACAT CGCCTACCAG
   631  CTCATGCATA ACATCAGGGA CATTGACGTG ATCATGGGGG GTGGCCGGAA ATACATGTAC CCCAAGAATA
   701  AAACTGATGT GGAGTATGAG AGTGACGAGA AGCCAGGGG CACGAGGCTG GACGCCTGG ACCTCGTTGA
   771  CACCTGGAAG AGCTTCAAAC CGAGATACAA GCACTCCCAC TTCATCTGGA ACCGCACGGA ACTCCTGACC
   841  CTTGACCCCC ACAATGTGGA CTACCTATTG GGTCTCTTCG AGCCAGGGGA CATGCAGTAC GAGCTGAACA
   911  GGAACAACGT GACGGACCCG TCACTCTCCG AGATGGTGGT GGTGGCCATC CAGATCCTGC GGAAGAACCC
   981  CAAAGGCTTC TTCTTGCTGG TGGAAGGAGG CAGAATTGAC CACGGGCACC ATGAAGGAAA AGCCAAGCAG
  1051  GCCCTGCATG AGGCGGTGGA GATGGACCGG GCCATCGGGC AGGCAGGCAG CTTGACCTCC TCGGAAGACA
  1121  CTCTGACCGT GGTCACTGCG GACCATTCCC ACGTCTTCAC ATTTGGTGGA TACACCCCCC GTGGCAACTC
  1191  TATCTTTGGT CTGGCCCCCA TGCTGAGTGA CACAGACAAG AAGCCCTTCA CTGCCATCCT GTATGGCAAT
  1261  GGGCCTGGCT ACAAGGTGGT GGGCGGTGAA CGAGAGAATG TCTCCATGGT GGACTATGCT CACAACAACT
  1331  ACCAGGCGCA GTCTGCTGTG CCCCTGCGCC ACGAGACCCA CGGCGGGGAG GACGTGGCCG TCTTCTCCAA
  1401  GGGCCCCATG GCGCACCTGC TGCACGGCGT CCACGAGCAG AACTACGTCC CCACGTGAT GGCGTATGCA
  1471  GCCTGCATCG GGGCCAACCT CGGCCACTGT GCTCCTGCCA GCTCGGATGA CGACGATGAT GACGATGATG
                  XbaI
                  ~~~~~~~
  1541  ACGACTAGTC TAGA
```

B

```
     1  MISPFLVLAI GTCLTNSLVP EKEKDPKYWR DQAQETLKYA LELQKLNTNV
    51  AKNVIMFLGD GMGVSTVTAA RILKGQLHHN PGEETRLEMD KFPFVALSKT
   101  YNTNAQVPDS AGTATAYLCG VKANEGTVGV SAATERSRCN TTQGNEVTSI
   151  LRWAKDAGKS VGIVTTTRVN HATPSAAYAH SADRDWYSDN EMPPEALSQG
   201  CKDIAYQLMH NIRDIDVIMG GGRKYMYPKN KTDVEYESDE KARGTRLDGL
   251  DLVDTWKSFK PRYKHSHFIW NRTELLTLDP HNVDYLLGLF EPGDMQYELN
   301  RNNVTDPSLS EMVVVAIQIL RKNPKGFFLL VEGGRIDHGH HEGKAKQALH
   351  EAVEMDRAIG QAGSLTSSED TLTVVTADHS HVFTFGGYTP RGNSIFGLAP
   401  MLSDTDKKPF TAILYGNGPG YKVVGGEREN VSMVDYAHNN YQAQSAVPLR
   451  HETHGGEDVA VFSKGPMAHL LHGVHEQNYV PHVMAYAACI GANLGHCAPA
   501  SSDDDDDDDD DD
```

Figure 17

SEQUENCE LISTING

```
<160> NUMBER OF SEQ ID NOS: 50

<210> SEQ ID NO 1
<211> LENGTH: 2280
<212> TYPE: DNA
<213> ORGANISM: Artificial
<220> FEATURE:
<223> OTHER INFORMATION: Encoding cleavable conjugate

<400> SEQUENCE: 1
atggaagcag aaacagggag cagcgtggag actggaaaga aggccaacag aggcactcga      60
attgccctgg tcgtgtttgt cctgacagtg atcgctcaac aaacaaccag tcaaggtctc     120
ttatccggag atgacgatga cgatgacgat gacgatgact ccggaagtct ccaagctaaa     180
caggagtact gcctgaagcc agaatgcatc gaagcggctg ctgccatctt aagtaaagta     240
aatctgtctg tggatccttg tgataatttc ttccggttcg cttgtgatgg ctggataagc     300
aataatccaa ttcccgaaga tatgccaagc tatgggtttt atccttggct gagacataat     360
gttgacctca gttgaagga acttttggag aaatcaatca gtagaaggcg ggacaccgaa     420
gccatacaga aagccaaaat cctttattca tcctgcatga atgagaaagc gattgaaaaa     480
gcagatgcca agccactgct acacatccta cggcattcac ctttccgctg gcccgtgctt     540
gaatctaata ttggccctga aggggtttgg tcagagagaa agttcagcct tctgcagaca     600
cttgcaacgt ttcgtggtca atacagcaat tctgtgttca tccgtttgta tgtgtccect     660 gatgacaaag catccaatga acatatcttg aagctggacc aagcaacact ctccctggcc     720
```

-continued

```
gtgagggaag actaccttga taacagtaca gaagccaagt cttatcggga tgcccttttac    780 aagttcatgg tggatactgc cgtgctttta ggagctaaca gttccagagc agagcatgac    840
atgaagtcag tgctcagatt ggaaattaag atagctgaga taatgattcc acatgaaaac    900
cgaaccagcg aggccatgta caacaaaatg aacatttctg aactgagtgc tatgattccc    960
cagttcgact ggctgggcta catcaagaag gtcattgaca ccagactcta cccccatctg   1020
aaagacatca gcccctccga gaatgtggtg gtccgcgtcc cgcagtactt taaagatttg   1080
tttaggatat tagggtctga gagaaagaag accattgcca actatttggt gtggagaatg   1140
gtttattcca gaattccaaa ccttagcagg cgctttcagt atagatggct ggaattctca   1200
agggtaatcc aggggaccac aactttgctg cctcaatggg acaaatgtgt aaactttatt   1260
gaaagtgccc tcccttatgt tgttggaaag atgtttgtag atgtgtactt ccaggaagat   1320
aagaaggaaa tgatggagga attggttgag ggcgttcgct gggcctttat tgacatgcta   1380
gagaaagaaa tgagtggat ggatgcagga acgaaaagga aagccaaaga aaaggcgaga   1440
gctgttttgg caaagttgg ctatccagag tttataatga atgatactca tgttaatgaa   1500
gacctcaaag ctatcaagtt ttcagaagcc gactactttg gcaacgtcct acaaactcgc   1560
aagtatttag cacagtctga tttcttctgg ctaagaaaag ccgttccaaa acagagtgg   1620 tttacaaatc cgacgactgt caatgccttc tacagtgcat ccaccaacca gatccgatt   1680 ccagcaggag agctccagaa gccttcttt tgggaacaa atatcctcg atctctgagt   1740 tatggtgcta taggagtaat tgtcggacat gaatttacac atggatttga taataatggt   1800
agaaaatatg ataaaaatgg aaacctggat ccttggtggt ctactgaatc agaagaaaag   1860
tttaaggaaa aaacaaaatg catgattaac cagtatagca actattattg gaagaaagct   1920
ggcttaaatg tcaagggaa gaggaccctg ggagaaaata ttgctgataa tggaggcctg   1980
cgggaagctt ttagggctta caggaaatgg ataaatgaca gaaggcaggg acttgaggag   2040
cctcttctac caggcatcac attcaccaac aaccagctct tcttcctgag ttatgctcat   2100
gtgaggtgca attcctacag accagaagct gcccgagaac aagtccaaat tggtgctcac   2160 agtcccctc agtttagggt caatggtgca attagtaact ttgaagaatt ccagaaagct   2220
tttaactgtc cacccaattc cacgatgaac agaggcatgg actcctgccg actctggtag   2280
```

<210> SEQ ID NO 2
<211> LENGTH: 759
<212> TYPE: PRT
<213> ORGANISM: Artificial
<220> FEATURE:
<223> OTHER INFORMATION: Cleavable PHEX conjugate

<400> SEQUENCE: 2

```
Met Glu Ala Glu Thr Gly Ser Ser Val Glu Thr Gly Lys Lys Ala Asn
1               5                   10                  15

Arg Gly Thr Arg Ile Ala Leu Val Val Phe Val Leu Thr Val Ile Ala
                20                  25                  30

Gln Gln Thr Thr Ser Gln Gly Leu Leu Ser Gly Asp Asp Asp Asp Asp
            35                  40                  45

Asp Asp Asp Asp Ser Gly Ser Leu Gln Ala Lys Gln Glu Tyr Cys
        50                  55                  60

Leu Lys Pro Glu Cys Ile Glu Ala Ala Ala Ile Leu Ser Lys Val
65                  70                  75                  80

Asn Leu Ser Val Asp Pro Cys Asp Asn Phe Phe Arg Phe Ala Cys Asp
                85                  90                  95
```

-continued

Gly Trp Ile Ser Asn Asn Pro Ile Pro Glu Asp Met Pro Ser Tyr Gly
            100                 105                 110

Val Tyr Pro Trp Leu Arg His Asn Val Asp Leu Lys Leu Lys Glu Leu
            115                 120                 125

Leu Glu Lys Ser Ile Ser Arg Arg Asp Thr Glu Ala Ile Gln Lys
            130                 135                 140

Ala Lys Ile Leu Tyr Ser Ser Cys Met Asn Glu Lys Ala Ile Glu Lys
145                 150                 155                 160

Ala Asp Ala Lys Pro Leu Leu His Ile Leu Arg His Ser Pro Phe Arg
                165                 170                 175

Trp Pro Val Leu Glu Ser Asn Ile Gly Pro Gly Val Trp Ser Glu
            180                 185                 190

Arg Lys Phe Ser Leu Leu Gln Thr Leu Ala Thr Phe Arg Gly Gln Tyr
            195                 200                 205

Ser Asn Ser Val Phe Ile Arg Leu Tyr Val Ser Pro Asp Asp Lys Ala
            210                 215                 220

Ser Asn Glu His Ile Leu Lys Leu Asp Gln Ala Thr Leu Ser Leu Ala
225                 230                 235                 240

Val Arg Glu Asp Tyr Leu Asp Asn Ser Thr Glu Ala Lys Ser Tyr Arg
                245                 250                 255

Asp Ala Leu Tyr Lys Phe Met Val Asp Thr Ala Val Leu Leu Gly Ala
            260                 265                 270

Asn Ser Ser Arg Ala Glu His Asp Met Lys Ser Val Leu Arg Leu Glu
            275                 280                 285

Ile Lys Ile Ala Glu Ile Met Ile Pro His Glu Asn Arg Thr Ser Glu
            290                 295                 300

Ala Met Tyr Asn Lys Met Asn Ile Ser Glu Leu Ser Ala Met Ile Pro
305                 310                 315                 320

Gln Phe Asp Trp Leu Gly Tyr Ile Lys Lys Val Ile Asp Thr Arg Leu
            325                 330                 335

Tyr Pro His Leu Lys Asp Ile Ser Pro Ser Glu Asn Val Val Arg
            340                 345                 350

Val Pro Gln Tyr Phe Lys Asp Leu Phe Arg Ile Leu Gly Ser Glu Arg
            355                 360                 365

Lys Lys Thr Ile Ala Asn Tyr Leu Val Trp Arg Met Val Tyr Ser Arg
370                 375                 380

Ile Pro Asn Leu Ser Arg Arg Phe Gln Tyr Arg Trp Leu Glu Phe Ser
385                 390                 395                 400

Arg Val Ile Gln Gly Thr Thr Thr Leu Leu Pro Gln Trp Asp Lys Cys
            405                 410                 415

Val Asn Phe Ile Glu Ser Ala Leu Pro Tyr Val Val Gly Lys Met Phe
            420                 425                 430

Val Asp Val Tyr Phe Gln Glu Asp Lys Lys Glu Met Met Glu Glu Leu
            435                 440                 445

Val Glu Gly Val Arg Trp Ala Phe Ile Asp Met Leu Glu Lys Glu Asn
            450                 455                 460

Glu Trp Met Asp Ala Gly Thr Lys Arg Lys Ala Lys Glu Lys Ala Arg
465                 470                 475                 480

Ala Val Leu Ala Lys Val Gly Tyr Pro Glu Phe Ile Met Asn Asp Thr
                485                 490                 495

His Val Asn Glu Asp Leu Lys Ala Ile Lys Phe Ser Glu Ala Asp Tyr
            500                 505                 510

Phe Gly Asn Val Leu Gln Thr Arg Lys Tyr Leu Ala Gln Ser Asp Phe
            515                 520                 525

Phe Trp Leu Arg Lys Ala Val Pro Lys Thr Glu Trp Phe Thr Asn Pro
    530                 535                 540

Thr Thr Val Asn Ala Phe Tyr Ser Ala Ser Thr Asn Gln Ile Arg Phe
545                 550                 555                 560

Pro Ala Gly Glu Leu Gln Lys Pro Phe Phe Trp Gly Thr Glu Tyr Pro
                565                 570                 575

Arg Ser Leu Ser Tyr Gly Ala Ile Val Ile Val Gly His Glu Phe
            580                 585                 590

Thr His Gly Phe Asp Asn Asn Gly Arg Lys Tyr Asp Lys Asn Gly Asn
        595                 600                 605

Leu Asp Pro Trp Trp Ser Thr Glu Ser Glu Glu Lys Phe Lys Glu Lys
    610                 615                 620

Thr Lys Cys Met Ile Asn Gln Tyr Ser Asn Tyr Tyr Trp Lys Lys Ala
625                 630                 635                 640

Gly Leu Asn Val Lys Gly Lys Arg Thr Leu Gly Glu Asn Ile Ala Asp
                645                 650                 655

Asn Gly Gly Leu Arg Glu Ala Phe Arg Ala Tyr Arg Lys Trp Ile Asn
            660                 665                 670

Asp Arg Arg Gln Gly Leu Glu Glu Pro Leu Leu Pro Gly Ile Thr Phe
        675                 680                 685

Thr Asn Asn Gln Leu Phe Phe Leu Ser Tyr Ala His Val Arg Cys Asn
    690                 695                 700

Ser Tyr Arg Pro Glu Ala Ala Arg Glu Gln Val Gln Ile Gly Ala His
705                 710                 715                 720

Ser Pro Pro Gln Phe Arg Val Asn Gly Ala Ile Ser Asn Phe Glu Glu
                725                 730                 735

Phe Gln Lys Ala Phe Asn Cys Pro Pro Asn Ser Thr Met Asn Arg Gly
            740                 745                 750

Met Asp Ser Cys Arg Leu Trp
        755

<210> SEQ ID NO 3
<211> LENGTH: 749
<212> TYPE: PRT
<213> ORGANISM: Homo sapiens

<400> SEQUENCE: 3

Met Glu Ala Glu Thr Gly Ser Ser Val Glu Thr Gly Lys Lys Ala Asn
1               5                   10                  15

Arg Gly Thr Arg Ile Ala Leu Val Val Phe Val Gly Gly Thr Leu Val
            20                  25                  30

Leu Gly Thr Ile Leu Phe Leu Val Ser Gln Gly Leu Leu Ser Leu Gln
        35                  40                  45

Ala Lys Gln Glu Tyr Cys Leu Lys Pro Glu Cys Ile Glu Ala Ala Ala
    50                  55                  60

Ala Ile Leu Ser Lys Val Asn Leu Ser Val Asp Pro Cys Asp Asn Phe
65                  70                  75                  80

Phe Arg Phe Ala Cys Asp Gly Trp Ile Ser Asn Asn Pro Ile Pro Glu
                85                  90                  95

Asp Met Pro Ser Tyr Gly Val Tyr Pro Trp Leu Arg His Asn Val Asp
            100                 105                 110

Leu Lys Leu Lys Glu Leu Leu Glu Lys Ser Ile Ser Arg Arg Arg Asp
        115                 120                 125

```
Thr Glu Ala Ile Gln Lys Ala Lys Ile Leu Tyr Ser Ser Cys Met Asn
    130                 135                 140
Glu Lys Ala Ile Glu Lys Ala Asp Ala Lys Pro Leu Leu His Ile Leu
145                 150                 155                 160
Arg His Ser Pro Phe Arg Trp Pro Val Leu Glu Ser Asn Ile Gly Pro
                165                 170                 175
Glu Gly Val Trp Ser Glu Arg Lys Phe Ser Leu Leu Gln Thr Leu Ala
                180                 185                 190
Thr Phe Arg Gly Gln Tyr Ser Asn Ser Val Phe Ile Arg Leu Tyr Val
            195                 200                 205
Ser Pro Asp Asp Lys Ala Ser Asn Glu His Ile Leu Lys Leu Asp Gln
210                 215                 220
Ala Thr Leu Ser Leu Ala Val Arg Glu Asp Tyr Leu Asp Asn Ser Thr
225                 230                 235                 240
Glu Ala Lys Ser Tyr Arg Asp Ala Leu Tyr Lys Phe Met Val Asp Thr
                245                 250                 255
Ala Val Leu Leu Gly Ala Asn Ser Ser Arg Ala Glu His Asp Met Lys
                260                 265                 270
Ser Val Leu Arg Leu Glu Ile Lys Ile Ala Glu Ile Met Ile Pro His
                275                 280                 285
Glu Asn Arg Thr Ser Glu Ala Met Tyr Asn Lys Met Asn Ile Ser Glu
290                 295                 300
Leu Ser Ala Met Ile Pro Gln Phe Asp Trp Leu Gly Tyr Ile Lys Lys
305                 310                 315                 320
Val Ile Asp Thr Arg Leu Tyr Pro His Leu Lys Asp Ile Ser Pro Ser
                325                 330                 335
Glu Asn Val Val Val Arg Val Pro Gln Tyr Phe Lys Asp Leu Phe Arg
                340                 345                 350
Ile Leu Gly Ser Glu Arg Lys Lys Thr Ile Ala Asn Tyr Leu Val Trp
                355                 360                 365
Arg Met Val Tyr Ser Arg Ile Pro Asn Leu Ser Arg Arg Phe Gln Tyr
    370                 375                 380
Arg Trp Leu Glu Phe Ser Arg Val Ile Gln Gly Thr Thr Thr Leu Leu
385                 390                 395                 400
Pro Gln Trp Asp Lys Cys Val Asn Phe Ile Glu Ser Ala Leu Pro Tyr
                405                 410                 415
Val Val Gly Lys Met Phe Val Asp Val Tyr Phe Gln Glu Asp Lys Lys
                420                 425                 430
Glu Met Met Glu Glu Leu Val Glu Gly Val Arg Trp Ala Phe Ile Asp
            435                 440                 445
Met Leu Glu Lys Glu Asn Glu Trp Met Asp Ala Gly Thr Lys Arg Lys
    450                 455                 460
Ala Lys Glu Lys Ala Arg Ala Val Leu Ala Lys Val Gly Tyr Pro Glu
465                 470                 475                 480
Phe Ile Met Asn Asp Thr His Val Asn Glu Asp Leu Lys Ala Ile Lys
                485                 490                 495
Phe Ser Glu Ala Asp Tyr Phe Gly Asn Val Leu Gln Thr Arg Lys Tyr
                500                 505                 510
Leu Ala Gln Ser Asp Phe Phe Trp Leu Arg Lys Ala Val Pro Lys Thr
            515                 520                 525
Glu Trp Phe Thr Asn Pro Thr Thr Val Asn Ala Phe Tyr Ser Ala Ser
    530                 535                 540
```

```
Thr Asn Gln Ile Arg Phe Pro Ala Gly Glu Leu Gln Lys Pro Phe
545                 550                 555                 560

Trp Gly Thr Glu Tyr Pro Arg Ser Leu Ser Tyr Gly Ala Ile Gly Val
                565                 570                 575

Ile Val Gly His Glu Phe Thr His Gly Phe Asp Asn Asn Gly Arg Lys
            580                 585                 590

Tyr Asp Lys Asn Gly Asn Leu Asp Pro Trp Trp Ser Thr Glu Ser Glu
        595                 600                 605

Glu Lys Phe Lys Glu Lys Thr Lys Cys Met Ile Asn Gln Tyr Ser Asn
    610                 615                 620

Tyr Tyr Trp Lys Lys Ala Gly Leu Asn Val Lys Gly Lys Arg Thr Leu
625                 630                 635                 640

Gly Glu Asn Ile Ala Asp Asn Gly Gly Leu Arg Glu Ala Phe Arg Ala
                645                 650                 655

Tyr Arg Lys Trp Ile Asn Asp Arg Arg Gln Gly Leu Glu Glu Pro Leu
            660                 665                 670

Leu Pro Gly Ile Thr Phe Thr Asn Asn Gln Leu Phe Phe Leu Ser Tyr
        675                 680                 685

Ala His Val Arg Cys Asn Ser Tyr Arg Pro Glu Ala Ala Arg Glu Gln
    690                 695                 700

Val Gln Ile Gly Ala His Ser Pro Pro Gln Phe Arg Val Asn Gly Ala
705                 710                 715                 720

Ile Ser Asn Ser Glu Glu Phe Gln Lys Ala Phe Asn Cys Pro Pro Asn
                725                 730                 735

Ser Thr Met Asn Arg Gly Met Asp Ser Cys Arg Leu Trp
            740                 745

<210> SEQ ID NO 4
<211> LENGTH: 718
<212> TYPE: PRT
<213> ORGANISM: artificial
<220> FEATURE:
<223> OTHER INFORMATION: Soluble PHEX conjugate

<400> SEQUENCE: 4

Ser Gly Asp Asp Asp Asp Asp Asp Asp Asp Ser Gly Ser Leu
1               5                   10                  15

Gln Ala Lys Gln Glu Tyr Cys Leu Lys Pro Glu Cys Ile Glu Ala Ala
                20                  25                  30

Ala Ala Ile Leu Ser Lys Val Asn Leu Ser Val Asp Pro Cys Asp Asn
            35                  40                  45

Phe Phe Arg Phe Ala Cys Asp Gly Trp Ile Ser Asn Asn Pro Ile Pro
50                  55                  60

Glu Asp Met Pro Ser Tyr Gly Val Tyr Pro Trp Leu Arg His Asn Val
65                  70                  75                  80

Asp Leu Lys Leu Lys Glu Leu Leu Glu Lys Ser Ile Ser Arg Arg Arg
                85                  90                  95

Asp Thr Glu Ala Ile Gln Lys Ala Lys Ile Leu Tyr Ser Ser Cys Met
            100                 105                 110

Asn Glu Lys Ala Ile Glu Lys Ala Asp Ala Lys Pro Leu Leu His Ile
        115                 120                 125

Leu Arg His Ser Pro Phe Arg Trp Pro Val Leu Glu Ser Asn Ile Gly
    130                 135                 140

Pro Glu Gly Val Trp Ser Glu Arg Lys Phe Ser Leu Leu Gln Thr Leu
145                 150                 155                 160
```

```
Ala Thr Phe Arg Gly Gln Tyr Ser Asn Ser Val Phe Ile Arg Leu Tyr
            165                 170                 175

Val Ser Pro Asp Asp Lys Ala Ser Asn Glu His Ile Leu Lys Leu Asp
        180                 185                 190

Gln Ala Thr Leu Ser Leu Ala Val Arg Glu Asp Tyr Leu Asp Asn Ser
            195                 200                 205

Thr Glu Ala Lys Ser Tyr Arg Asp Ala Leu Tyr Lys Phe Met Val Asp
    210                 215                 220

Thr Ala Val Leu Leu Gly Ala Asn Ser Ser Arg Ala Glu His Asp Met
225                 230                 235                 240

Lys Ser Val Leu Arg Leu Glu Ile Lys Ile Ala Glu Ile Met Ile Pro
                245                 250                 255

His Glu Asn Arg Thr Ser Glu Ala Met Tyr Asn Lys Met Asn Ile Ser
            260                 265                 270

Glu Leu Ser Ala Met Ile Pro Gln Phe Asp Trp Leu Gly Tyr Ile Lys
        275                 280                 285

Lys Val Ile Asp Thr Arg Leu Tyr Pro His Leu Lys Asp Ile Ser Pro
    290                 295                 300

Ser Glu Asn Val Val Arg Val Pro Gln Tyr Phe Lys Asp Leu Phe
305                 310                 315                 320

Arg Ile Leu Gly Ser Glu Arg Lys Thr Ile Ala Asn Tyr Leu Val
            325                 330                 335

Trp Arg Met Val Tyr Ser Arg Ile Pro Asn Leu Ser Arg Arg Phe Gln
                340                 345                 350

Tyr Arg Trp Leu Glu Phe Ser Arg Val Ile Gln Gly Thr Thr Thr Leu
            355                 360                 365

Leu Pro Gln Trp Asp Lys Cys Val Asn Phe Ile Glu Ser Ala Leu Pro
    370                 375                 380

Tyr Val Val Gly Lys Met Phe Val Asp Val Tyr Phe Gln Glu Asp Lys
385                 390                 395                 400

Lys Glu Met Met Glu Glu Leu Val Glu Gly Val Arg Trp Ala Phe Ile
                405                 410                 415

Asp Met Leu Glu Lys Glu Asn Glu Trp Met Asp Ala Gly Thr Lys Arg
            420                 425                 430

Lys Ala Lys Glu Lys Ala Arg Ala Val Leu Ala Lys Val Gly Tyr Pro
    435                 440                 445

Glu Phe Ile Met Asn Asp Thr His Val Asn Glu Asp Leu Lys Ala Ile
            450                 455                 460

Lys Phe Ser Glu Ala Asp Tyr Phe Gly Asn Val Leu Gln Thr Arg Lys
465                 470                 475                 480

Tyr Leu Ala Gln Ser Asp Phe Phe Trp Leu Arg Lys Ala Val Pro Lys
                485                 490                 495

Thr Glu Trp Phe Thr Asn Pro Thr Thr Val Asn Ala Phe Tyr Ser Ala
            500                 505                 510

Ser Thr Asn Gln Ile Arg Phe Pro Ala Gly Glu Leu Gln Lys Pro Phe
        515                 520                 525

Phe Trp Gly Thr Glu Tyr Pro Arg Ser Leu Ser Tyr Gly Ala Ile Gly
    530                 535                 540

Val Ile Val Gly His Glu Phe Thr His Gly Phe Asp Asn Asn Gly Arg
545                 550                 555                 560

Lys Tyr Asp Lys Asn Gly Asn Leu Asp Pro Trp Trp Ser Thr Glu Ser
                565                 570                 575

Glu Glu Lys Phe Lys Glu Lys Thr Lys Cys Met Ile Asn Gln Tyr Ser
```

```
              580                 585                 590
Asn Tyr Tyr Trp Lys Lys Ala Gly Leu Asn Val Lys Gly Lys Arg Thr
                595                 600                 605

Leu Gly Glu Asn Ile Ala Asp Asn Gly Gly Leu Arg Glu Ala Phe Arg
    610                 615                 620

Ala Tyr Arg Lys Trp Ile Asn Asp Arg Arg Gln Gly Leu Glu Glu Pro
625                 630                 635                 640

Leu Leu Pro Gly Ile Thr Phe Thr Asn Asn Gln Leu Phe Phe Leu Ser
                645                 650                 655

Tyr Ala His Val Arg Cys Asn Ser Tyr Arg Pro Glu Ala Ala Arg Glu
            660                 665                 670

Gln Val Gln Ile Gly Ala His Ser Pro Pro Gln Phe Arg Val Asn Gly
        675                 680                 685

Ala Ile Ser Asn Phe Glu Glu Phe Gln Lys Ala Phe Asn Cys Pro Pro
    690                 695                 700

Asn Ser Thr Met Asn Arg Gly Met Asp Ser Cys Arg Leu Trp
705                 710                 715
```

<210> SEQ ID NO 5
<211> LENGTH: 1524
<212> TYPE: DNA
<213> ORGANISM: Artificial
<220> FEATURE:
<223> OTHER INFORMATION: Encoding soluble alkaline phosphatase

<400> SEQUENCE: 5

```
ggatccacca tgatttcacc attcttagta ctggccattg cacctgcct  tactaactcc      60
ttagtgccag agaaagagaa agaccccaag tactggcgag accaagcgca agagacactg     120
aaatatgccc tggagcttca gaagctcaac accaacgtgg ctaagaatgt catcatgttc     180
ctgggagatg ggatgggtgt ctccacagtg acggctgccc gcatcctcaa gggtcagctc     240
caccacaacc ctgggggagga gaccaggctg agatgaca   agttccccctt cgtgcccctc     300
tccaagacgt acaacaccaa tgcccaggtc cctgacagcg ccggcaccgc caccgcctac     360
ctgtgtgggg tgaaggccaa tgagggcacc gtgggggtaa gcgcagccac tgagcgttcc     420
cggtgcaaca ccacccaggg gaacgaggtc acctccatcc tgcgctgggc caaggacgct     480
gggaaatctg tgggcattgt gaccaccacg agagtgaacc atgccacccc cagcgccgcc     540
tacgcccact cggctgaccg ggactggtac tcagacaacg agatgccccc tgaggccttg     600
agccagggct gtaaggacat cgcctaccag ctcatgcata acatcaggga cattgacgtg     660
atcatggggg gtggccggaa atacatgtac cccaagaata aaactgatgt ggagtatgag     720
agtgacgaga agccagggg  cacgaggctg gacggcctgg acctcgttga cacctggaag     780
agcttcaaac cgagatacaa gcactcccac ttcatctgga accgcacgga actcctgacc     840
cttgaccccc acaatgtgga ctacctattg ggtctcttcg agccagggga catgcagtac     900
gagctgaaca ggaacaacgt gacggacccg tcactctccg agatggtggt ggtggccatc     960
cagatcctgc ggaagaaccc caaaggcttc ttcttgctgg tggaaggagg cagaattgac    1020
cacgggcacc atgaaggaaa agccaagcag gccctgcatg aggcggtgga gatgaccgg    1080
gccatcgggc aggcaggcag cttgacctcc tcggaagaca ctctgaccgt ggtcactgcg    1140
gaccattccc acgtcttcac atttggtgga tacccccccc gtggcaactc tatctttggt    1200
ctggcccccca tgctgagtga cacagacaag aagcccttca ctgccatcct gtatggcaat    1260
gggcctggct acaaggtggt gggcggtgaa cgagagaatg tctccatggt ggactatgct    1320
```

-continued

```
cacaacaact accaggcgca gtctgctgtg cccctgcgcc acgagaccca cggcggggag    1380
gacgtggccg tcttctccaa gggccccatg gcgcacctgc tgcacggcgt ccacgagcag    1440
aactacgtcc ccacgtgat ggcgtatgca gcctgcatcg gggccaacct cggccactgt    1500
gctcctgcca gctcgtagtc taga                                           1524
```

<210> SEQ ID NO 6
<211> LENGTH: 502
<212> TYPE: PRT
<213> ORGANISM: Artificial
<220> FEATURE:
<223> OTHER INFORMATION: Soluble alkaline phosphatase

<400> SEQUENCE: 6

```
Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Val Ala Ile Gln Ile Leu
305                 310                 315                 320
```

```
Arg Lys Asn Pro Lys Gly Phe Phe Leu Leu Val Glu Gly Gly Arg Ile
                325                 330                 335
Asp His Gly His His Glu Gly Lys Ala Lys Gln Ala Leu His Glu Ala
            340                 345                 350
Val Glu Met Asp Arg Ala Ile Gly Gln Ala Gly Ser Leu Thr Ser Ser
        355                 360                 365
Glu Asp Thr Leu Thr Val Val Thr Ala Asp His Ser His Val Phe Thr
    370                 375                 380
Phe Gly Gly Tyr Thr Pro Arg Gly Asn Ser Ile Phe Gly Leu Ala Pro
385                 390                 395                 400
Met Leu Ser Asp Thr Asp Lys Lys Pro Phe Thr Ala Ile Leu Tyr Gly
                405                 410                 415
Asn Gly Pro Gly Tyr Lys Val Val Gly Gly Glu Arg Glu Asn Val Ser
            420                 425                 430
Met Val Asp Tyr Ala His Asn Asn Tyr Gln Ala Gln Ser Ala Val Pro
        435                 440                 445
Leu Arg His Glu Thr His Gly Gly Glu Asp Val Ala Val Phe Ser Lys
    450                 455                 460
Gly Pro Met Ala His Leu Leu His Gly Val His Glu Gln Asn Tyr Val
465                 470                 475                 480
Pro His Val Met Ala Tyr Ala Ala Cys Ile Gly Ala Asn Leu Gly His
                485                 490                 495
Cys Ala Pro Ala Ser Ser
            500
```

<210> SEQ ID NO 7
<211> LENGTH: 1554
<212> TYPE: DNA
<213> ORGANISM: Artificial
<220> FEATURE:
<223> OTHER INFORMATION: Encoding soluble alkaline phosphatase conjugate

<400> SEQUENCE: 7

```
ggatccacca tgatttcacc attcttagta ctggccattg caccctgcct tactaactcc      60
ttagtgccag agaaagagaa agaccccaag tactggcgag accaagcgca agagacactg     120
aaatatgccc tggagcttca gaagctcaac accaacgtgg ctaagaatgt catcatgttc     180
ctgggagatg gatgggtgt ctccacagtg acggctgccc gcatcctcaa gggtcagctc     240
caccacaacc ctggggagga gaccaggctg agatggaca agttcccctt cgtggccctc     300
tccaagacgt acaacaccaa tgcccaggtc cctgacagcg ccggcaccgc caccgcctac     360
ctgtgtgggg tgaaggccaa tgagggcacc gtggggtaa gcgcagccac tgagcgttcc     420
cggtgcaaca ccacccaggg gaacgaggtc acctccatcc tgcgctgggc caaggacgct     480
gggaaatctg tgggcattgt gaccaccacg agagtgaacc atgccacccc cagcgccgcc     540
tacgcccact cggctgaccg ggactggtac tcagacaacg atgccccc tgaggccttg     600
agccagggct gtaaggacat cgcctaccag ctcatgcata acatcaggga cattgacgtg     660
atcatggggg gtggccggaa atacatgtac cccaagaata aaactgatgt ggagtatgag     720
agtgacgaga agccaggggg cacgaggctg gacggcctgg acctcgttga cacctggaag     780
agcttcaaac cgagatacaa gcactcccac ttcatctgga accgcacgga actcctgacc     840
cttgaccccc acaatgtgga ctacctattg ggtctcttcg agccagggga catgcagtac     900
gagctgaaca ggaacaacgt gacggacccg tcactctccg agatggtggt ggtggccatc     960
cagatcctgc ggaagaaccc caaaggcttc ttcttgctgg tggaaggagg cagaattgac    1020
```

```
cacgggcacc atgaaggaaa agccaagcag gccctgcatg aggcggtgga gatggaccgg    1080
gccatcgggc aggcaggcag cttgacctcc tcggaagaca ctctgaccgt ggtcactgcg    1140
gaccattccc acgtcttcac atttggtgga tacaccccccc gtggcaactc tatctttggt   1200
ctggccccca tgctgagtga cacagacaag aagcccttca ctgccatcct gtatggcaat    1260
gggcctggct acaaggtggt gggcggtgaa cgagagaatg tctccatggt ggactatgct    1320
cacaacaact accaggcgca gtctgctgtg cccctgcgcc acgagaccca cggcggggag    1380
gacgtggccg tcttctccaa gggccccatg gcgcacctgc tgcacggcgt ccacgagcag    1440
aactacgtcc ccacgtgat ggcgtatgca gcctgcatcg gggccaacct cggccactgt     1500
gctcctgcca gctcggatga cgacgatgat gacgatgatg acgactagtc taga          1554
```

<210> SEQ ID NO 8
<211> LENGTH: 512
<212> TYPE: PRT
<213> ORGANISM: Artificial
<220> FEATURE:
<223> OTHER INFORMATION: Soluble alkaline phosphatase conjugate

<400> SEQUENCE: 8

```
Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270
```

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Arg Ile
                325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
435                 440                 445

Leu Arg His Glu Thr His Gly Gly Glu Asp Val Ala Val Phe Ser Lys
            450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Asp Asp Asp Asp Asp Asp Asp Asp
            500                 505                 510

<210> SEQ ID NO 9
<211> LENGTH: 25
<212> TYPE: DNA
<213> ORGANISM: Artificial
<220> FEATURE:
<223> OTHER INFORMATION: Oligonucleotide

<400> SEQUENCE: 9
gatccgatga cgatgacgat gacgc                                    25

<210> SEQ ID NO 10
<211> LENGTH: 25
<212> TYPE: DNA
<213> ORGANISM: Artificial
<220> FEATURE:
<223> OTHER INFORMATION: Oligonucleotide

<400> SEQUENCE: 10
ggccgcgtca tcgtcatcgt catcg                                    25

<210> SEQ ID NO 11
<211> LENGTH: 37
<212> TYPE: DNA
<213> ORGANISM: Artificial
<220> FEATURE:
<223> OTHER INFORMATION: Oligonucleotide

<400> SEQUENCE: 11

```
gatccgatga cgatgacgat gacgatgacg atgacgc                                37
```

<210> SEQ ID NO 12
<211> LENGTH: 37
<212> TYPE: DNA
<213> ORGANISM: Artificial
<220> FEATURE:
<223> OTHER INFORMATION: Oligonucleotide

<400> SEQUENCE: 12

```
ggccgcgtca tcgtcatcgt catcgtcatc gtcatcg                                37
```

<210> SEQ ID NO 13
<211> LENGTH: 55
<212> TYPE: DNA
<213> ORGANISM: Artificial
<220> FEATURE:
<223> OTHER INFORMATION: Oligonucleotide

<400> SEQUENCE: 13

```
gatccgatga cgatgacgat gacgatgacg atgacgatga cgatgacgat gacgc           55
```

<210> SEQ ID NO 14
<211> LENGTH: 55
<212> TYPE: DNA
<213> ORGANISM: Artificial
<220> FEATURE:
<223> OTHER INFORMATION: Oligonucleotide

<400> SEQUENCE: 14

```
ggccgcgtca tcgtcatcgt catcgtcatc gtcatcgtca tcgtcatcgt catcg           55
```

<210> SEQ ID NO 15
<211> LENGTH: 61
<212> TYPE: DNA
<213> ORGANISM: Artificial
<220> FEATURE:
<223> OTHER INFORMATION: Oligonucleotide

<400> SEQUENCE: 15

```
gatccgatga cagtagtgag tcatctgaca gtggcagttc aagtgagagc gatggtgacg      60
c                                                                      61
```

<210> SEQ ID NO 16
<211> LENGTH: 61
<212> TYPE: DNA
<213> ORGANISM: Artificial
<220> FEATURE:
<223> OTHER INFORMATION: Oligonucleotide

<400> SEQUENCE: 16

```
ggccgcgtca ccatcgctct cacttgaact gccactgtca gatgactcac tactgtcatc      60
g                                                                      61
```

<210> SEQ ID NO 17
<211> LENGTH: 52
<212> TYPE: DNA
<213> ORGANISM: Artificial
<220> FEATURE:
<223> OTHER INFORMATION: Oligonucleotide

<400> SEQUENCE: 17

```
gatccgattc atctgaagag aaattttgc gtagaattgg aagattcggt gc               52
```

<210> SEQ ID NO 18
<211> LENGTH: 52
<212> TYPE: DNA
<213> ORGANISM: Artificial
<220> FEATURE:
<223> OTHER INFORMATION: Oligonucleotide

<400> SEQUENCE: 18
ggccgcaccg aatcttccaa ttctacgcaa aaatttctct tcagatgaat cg          52

<210> SEQ ID NO 19
<211> LENGTH: 58
<212> TYPE: DNA
<213> ORGANISM: Artificial
<220> FEATURE:
<223> OTHER INFORMATION: Oligonucleotide

<400> SEQUENCE: 19
gatcctgtta tgaatcacat gaaagcatgg aatcttatga acttaatccc ttcattgc    58

<210> SEQ ID NO 20
<211> LENGTH: 58
<212> TYPE: DNA
<213> ORGANISM: Artificial
<220> FEATURE:
<223> OTHER INFORMATION: Oligonucleotide

<400> SEQUENCE: 20
ggccgcaatg aagggattaa gttcataaga ttccatgctt tcatgtgatt cataacag    58

<210> SEQ ID NO 21
<211> LENGTH: 46
<212> TYPE: DNA
<213> ORGANISM: Artificial
<220> FEATURE:
<223> OTHER INFORMATION: Oligonucleotide

<400> SEQUENCE: 21
gatcccagaa tgctgtgtcc tctgaagaaa ccaatgactt taaagc                 46

<210> SEQ ID NO 22
<211> LENGTH: 46
<212> TYPE: DNA
<213> ORGANISM: Artificial
<220> FEATURE:
<223> OTHER INFORMATION: Oligonucleotide

<400> SEQUENCE: 22
ggccgcttta aagtcattgg tttcttcaga ggacacagca ttctgg                 46

<210> SEQ ID NO 23
<211> LENGTH: 64
<212> TYPE: DNA
<213> ORGANISM: Artificial
<220> FEATURE:
<223> OTHER INFORMATION: Oligonucleotide

<400> SEQUENCE: 23
gatccggcag tagtgactca tccgaagaaa atggagatga cagttcagaa gaggaggagg  60
aagc                                                              64

<210> SEQ ID NO 24
<211> LENGTH: 64
<212> TYPE: DNA
<213> ORGANISM: Artificial

<220> FEATURE:
<223> OTHER INFORMATION: Oligonucleotide

<400> SEQUENCE: 24
ggccgcttcc tcctcctctt ctgaactgtc atctccattt tcttcggatg agtcactact    60
gccg                                                                64

<210> SEQ ID NO 25
<211> LENGTH: 61
<212> TYPE: DNA
<213> ORGANISM: Artificial
<220> FEATURE:
<223> OTHER INFORMATION: Oligonucleotide

<400> SEQUENCE: 25
gatcccgcaa aggattctac aagagaaagc agtgcaaacc ttcccgtggc cgcaagcgtg    60
c                                                                   61

<210> SEQ ID NO 26
<211> LENGTH: 61
<212> TYPE: DNA
<213> ORGANISM: Artificial
<220> FEATURE:
<223> OTHER INFORMATION: Oligonucleotide

<400> SEQUENCE: 26
ggccgcacgc ttgcggccac gggaaggttt gcactgcttt ctcttgtaga atcctttgcg    60
g                                                                   61

<210> SEQ ID NO 27
<211> LENGTH: 32
<212> TYPE: DNA
<213> ORGANISM: Artificial
<220> FEATURE:
<223> OTHER INFORMATION: Oligonucleotide

<400> SEQUENCE: 27
agtcgggatc cggaacaagc agcgtgttct ac                                  32

<210> SEQ ID NO 28
<211> LENGTH: 39
<212> TYPE: DNA
<213> ORGANISM: Artificial
<220> FEATURE:
<223> OTHER INFORMATION: Oligonucleotide

<400> SEQUENCE: 28
agatcgcggc cgctcaattg tgcacggtgt gattaaagg                           39

<210> SEQ ID NO 29
<211> LENGTH: 36
<212> TYPE: DNA
<213> ORGANISM: Artificial
<220> FEATURE:
<223> OTHER INFORMATION: Oligonucleotide

<400> SEQUENCE: 29
ccggagatga cgatgacgat gacgatgacg atgact                              36

<210> SEQ ID NO 30
<211> LENGTH: 36
<212> TYPE: DNA
<213> ORGANISM: Artificial
<220> FEATURE:

<223> OTHER INFORMATION: Oligonucleotide

<400> SEQUENCE: 30
tctactgcta ctgctactgc tactgctact gaggcc				36

<210> SEQ ID NO 31
<211> LENGTH: 18
<212> TYPE: PRT
<213> ORGANISM: Artificial
<220> FEATURE:
<223> OTHER INFORMATION: Human fragment of MEPE

<400> SEQUENCE: 31

Asp Asp Ser Ser Glu Ser Ser Asp Ser Gly Ser Ser Ser Glu Ser Asp
1               5                   10                  15

Gly Asp

<210> SEQ ID NO 32
<211> LENGTH: 15
<212> TYPE: PRT
<213> ORGANISM: Artificial
<220> FEATURE:
<223> OTHER INFORMATION: Human fragment of Statherin

<400> SEQUENCE: 32

Asp Ser Ser Glu Glu Lys Phe Leu Arg Arg Ile Gly Arg Phe Gly
1               5                   10                  15

<210> SEQ ID NO 33
<211> LENGTH: 17
<212> TYPE: PRT
<213> ORGANISM: Artificial
<220> FEATURE:
<223> OTHER INFORMATION: Human fragment of MGP

<400> SEQUENCE: 33

Cys Tyr Glu Ser His Glu Ser Met Glu Ser Tyr Glu Leu Asn Pro Phe
1               5                   10                  15

Ile

<210> SEQ ID NO 34
<211> LENGTH: 13
<212> TYPE: PRT
<213> ORGANISM: Artificial
<220> FEATURE:
<223> OTHER INFORMATION: Human fragment of OPN

<400> SEQUENCE: 34

Gln Asn Ala Val Ser Ser Glu Glu Thr Asn Asp Phe Lys
1               5                   10

<210> SEQ ID NO 35
<211> LENGTH: 18
<212> TYPE: PRT
<213> ORGANISM: Artificial
<220> FEATURE:
<223> OTHER INFORMATION: Human fragment of BSP2

<400> SEQUENCE: 35

Gly Ser Ser Asp Ser Ser Glu Glu Asn Gly Asp Asp Ser Ser Glu Glu
1               5                   10                  15

Glu Glu

<210> SEQ ID NO 36

```
<211> LENGTH: 18
<212> TYPE: PRT
<213> ORGANISM: Artificial
<220> FEATURE:
<223> OTHER INFORMATION: Human fragment of IGFBP5

<400> SEQUENCE: 36

Arg Lys Gly Phe Tyr Lys Arg Lys Gln Cys Lys Pro Ser Arg Gly Arg
1               5                   10                  15

Lys Arg

<210> SEQ ID NO 37
<211> LENGTH: 151
<212> TYPE: PRT
<213> ORGANISM: Artificial
<220> FEATURE:
<223> OTHER INFORMATION: Collagen binding domain of staphilococcus
      aureus collagen adhesin M81736

<400> SEQUENCE: 37

Gly Thr Ser Ser Val Phe Tyr Tyr Lys Thr Gly Asp Met Leu Pro Glu
1               5                   10                  15

Asp Thr Thr His Val Arg Trp Phe Leu Asn Ile Asn Asn Glu Lys Ser
            20                  25                  30

Tyr Val Ser Lys Asp Ile Thr Ile Lys Asp Gln Ile Gln Gly Gly Gln
        35                  40                  45

Gln Leu Asp Leu Ser Thr Leu Asn Ile Asn Val Thr Gly Thr His Ser
    50                  55                  60

Asn Tyr Tyr Ser Gly Gln Ser Ala Ile Thr Asp Phe Glu Lys Ala Phe
65                  70                  75                  80

Pro Gly Ser Lys Ile Thr Val Asp Asn Thr Lys Asn Thr Ile Asp Val
                85                  90                  95

Thr Ile Pro Gln Gly Tyr Gly Ser Tyr Asn Ser Phe Ser Ile Asn Tyr
            100                 105                 110

Lys Thr Lys Ile Thr Asn Glu Gln Gln Lys Glu Phe Val Asn Asn Ser
        115                 120                 125

Gln Ala Trp Tyr Gln Glu His Gly Lys Glu Val Asn Gly Lys Ser
    130                 135                 140

Phe Asn His Thr Val His Asn
145                 150

<210> SEQ ID NO 38
<211> LENGTH: 41
<212> TYPE: DNA
<213> ORGANISM: Artificial
<220> FEATURE:
<223> OTHER INFORMATION: Oligonucleotide primer

<400> SEQUENCE: 38
cagtcaaggt ctcttatccg gaagtctcca agctaaacag g                    41

<210> SEQ ID NO 39
<211> LENGTH: 41
<212> TYPE: DNA
<213> ORGANISM: Artificial
<220> FEATURE:
<223> OTHER INFORMATION: Oligonucleotide primer

<400> SEQUENCE: 39
ctgtttagct tggagacttc cggataagag accttgactg g                    41
```

```
<210> SEQ ID NO 40
<211> LENGTH: 25
<212> TYPE: DNA
<213> ORGANISM: Artificial
<220> FEATURE:
<223> OTHER INFORMATION: Oligonucleotide primer

<400> SEQUENCE: 40
gataaagcag gtcttggggt gcacc                                          25

<210> SEQ ID NO 41
<211> LENGTH: 25
<212> TYPE: DNA
<213> ORGANISM: Artificial
<220> FEATURE:
<223> OTHER INFORMATION: Oligonucleotide primer

<400> SEQUENCE: 41
gttggcatct gtcacgggct tgtgg                                          25

<210> SEQ ID NO 42
<211> LENGTH: 32
<212> TYPE: DNA
<213> ORGANISM: Artificial
<220> FEATURE:
<223> OTHER INFORMATION: Oligonucleotide primer

<400> SEQUENCE: 42
tggatccacc atgatttcac cattcttagt ac                                  32

<210> SEQ ID NO 43
<211> LENGTH: 35
<212> TYPE: DNA
<213> ORGANISM: Artificial
<220> FEATURE:
<223> OTHER INFORMATION: Oligonucleotide primer

<400> SEQUENCE: 43
ttctagacta cgagctggca ggagcacagt ggccg                               35

<210> SEQ ID NO 44
<211> LENGTH: 65
<212> TYPE: DNA
<213> ORGANISM: Artificial
<220> FEATURE:
<223> OTHER INFORMATION: Oligonucleotide primer

<400> SEQUENCE: 44
ttctagacta gtcgtcatca tcgtcatcat cgtcgtcatc cgagctggca ggagcacagt    60
ggccg                                                                65

<210> SEQ ID NO 45
<211> LENGTH: 5
<212> TYPE: PRT
<213> ORGANISM: Artificial sequence
<220> FEATURE:
<223> OTHER INFORMATION: Fragment surrounding cleavage site

<400> SEQUENCE: 45

Ser Leu Gln Ala Lys
1               5

<210> SEQ ID NO 46
<211> LENGTH: 11
<212> TYPE: PRT
<213> ORGANISM: Artificial sequence
```

```
<220> FEATURE:
<223> OTHER INFORMATION: Fragment surrounding cleavage site

<400> SEQUENCE: 46

Thr Ser Asp Lys Thr His Ser Leu Gln Ala Lys
1               5                   10

<210> SEQ ID NO 47
<211> LENGTH: 7
<212> TYPE: PRT
<213> ORGANISM: Artificial sequence
<220> FEATURE:
<223> OTHER INFORMATION: Fragment surrounding cleavage site

<400> SEQUENCE: 47

Ser Val Ser Leu Gln Ala Lys
1               5

<210> SEQ ID NO 48
<211> LENGTH: 19
<212> TYPE: PRT
<213> ORGANISM: Artificial sequence
<220> FEATURE:
<223> OTHER INFORMATION: Fragment surrounding cleavage site

<400> SEQUENCE: 48

Ser Gly Asp Asp Asp Asp Asp Asp Asp Asp Asp Ser Gly Ser Leu
1               5                   10                  15

Gln Ala Lys

<210> SEQ ID NO 49
<211> LENGTH: 14
<212> TYPE: PRT
<213> ORGANISM: Artificial sequence
<220> FEATURE:
<223> OTHER INFORMATION: Fragment surrounding cleavage site

<400> SEQUENCE: 49

Ser Asp Asp Asp Asp Asp Asp Tyr Val Ser Leu Gln Ala Lys
1               5                   10

<210> SEQ ID NO 50
<211> LENGTH: 8
<212> TYPE: PRT
<213> ORGANISM: Artificial sequence
<220> FEATURE:
<223> OTHER INFORMATION: Fragment surrounding cleavage site

<400> SEQUENCE: 50

Arg Thr Val Val Lys Arg Ser Val
1               5
```

BONE DELIVERY CONJUGATES AND METHOD OF USING SAME TO TARGET PROTEINS TO BONE

CROSS REFERENCE TO RELATED APPLICATIONS

This application is a continuation of U.S. application Ser. No. 11/111,664, filed Apr. 21, 2005, which claims the benefit of the filing dates of U.S. Provisional Application Nos. 60/563,828 filed Apr. 21, 2004, 60/590,347 filed Jul. 23, 2004, and 60/614,984 filed Oct. 4, 2004, each of which is incorporated herein by reference.

FIELD OF THE INVENTION

The present invention relates to bone delivery conjugates and method of using same to target proteins to bone. More specifically, the present invention relates to bone delivery compositions comprising peptide motifs, engineered within the structure of a protein through recombinant DNA technology to promote binding to bone matrix.

BACKGROUND OF THE INVENTION

Technological advances in molecular biology, recombinant protein production and large scale protein purification have allowed the production of large amounts of proteins now used as biopharmaceuticals. For example, monoclonal antibodies and soluble forms of the TNF-a receptor have been used in the treatment of autoimmune diseases such as Crohn's disease or severe forms of psoriasis (1). Another example of use of recombinant protein is enzyme replacement therapy (ERT). ERT has been used to treat lysosomal storage diseases. This group of genetic disorders is characterized by the loss of function of lysosome enzymes resulting in severe somatic, and sometimes neuronal, pathologies. In ERT for these diseases, the patients are infused with large doses of normal enzymes. These infused enzymes are then internalized from circulation via cell surface receptors (mannose-6 phosphate receptor) and enter the endocytic pathway on their way to their site of action, the lysosome. Not all attempts to treat genetic disorders through ERT have been successful.

Hypophosphatasia is a rare, heritable type of rickets or osteomalacia that occurs with an incidence of 1 per 100,000 births for the more severe form of the disease. Milder forms are more prevalent. In this inborn metabolism defect, mutations inactivate the gene that encodes the tissue-nonspecific isoenzyme of alkaline phosphatase. It is characterized biochemically by subnormal alkaline phosphatase activity in serum. Alkaline phosphatase deficiency in osteoblasts and chondrocytes impairs skeletal mineralization, leading to rickets or osteomalacia.

There is a very broad range of expressivity of hypophosphatasia, spanning from a perinatal form often causing stillbirth from an unmineralized skeleton, to a milder form featuring only premature loss of teeth. Severely affected infants and children inherit hypophosphatasia as an autosomal recessive trait. There are four main forms of the disease: perinatal, infantile, childhood and adult. Perinatal hypophosphatasia manifests during gestation and most affected newborns survive only briefly. Infantile hypophosphatasia becomes clinically apparent before 6 months of age. About 50% of patients die within a year. Childhood hypophosphatasia varies greatly in severity but most of these patients will suffer from skeletal symptoms throughout their life. Adult hypophosphatasia appears during middle age, with symptoms such as painful recurrent stress fractures having poor healing.

Osteoblasts and chondrocytes are normally rich in tissue-nonspecific alkaline phosphatase where it is attached to the cell surface. In hypophosphatasia, the lack of alkaline phosphatase activity results in the extracellular accumulation of three phosphorus-compounds believed to be substrates of the enzyme: phosphoethanolamine (PEA), inorganic pyrophosphate (PPi) and pyridoxal 5'-phosphate (PLP). PPi is an inhibitor of hydroxyapatite crystal growth, and PPi build-up in the disease accounts for the impaired skeletal mineralization. Consequently, providing active enzyme to patients suffering from hypophosphatasia will decrease extracellular PPi levels and improve skeletal mineralization.

Currently, there is no established medical therapy for hypophosphatasia. Trials of enzyme replacement using intravenous infusions of alkaline phosphatase have failed. It appears that alkaline phosphatase activity must be increased not in circulation but in the skeleton itself. This hypothesis was confirmed recently by bone marrow transplantation. Unfortunately, the benefits of the transplantation lasted only for a short period of time due to poor engraftment.

There is a therefore a need to provide enzyme replacement therapy approach to provide active enzyme to the skeleton of patients suffering from hypophosphatasia.

Bone-targeted proteins could be useful not only for the treatment or prevention of hypophosphatasia (loss of function of alkaline phosphatase) but also for the treatment or prevention of other genetic diseases characterized by defective enzymatic activity involved in bone metabolism, such as X-linked hypophosphatemic rickets (XLH) (loss of function of phosphate regulating gene with homology to endopeptidases on the X chromosome (PHEX)).

XLH is the most prevalent of the familial hypophosphatemias (OMIM 307800, 307810). It is characterized by reduced phosphate reuptake in the kidney, hypophosphatemia, normocalcemia, normal to low plasma 1,25-dihydroxyvitamin D3 (1,25(OH)2D, calcitriol) levels, normal parathyroid gland function and elevated plasma alkaline phosphatase activity. These changes are associated with growth retardation, lower extremity deformity, radiologic and histomorphometric evidence of rickets and osteomalacia. This disease appears to result from combined renal defects in tubular phosphate reabsorption and vitamin D metabolism, as well as a functional disorder in bone and teeth. XLH results from inactivating mutations in the PHEX gene, a member of the zinc metallopeptidase family of type II integral membrane glycoproteins. These mutations prevent the expression of a functional PHEX enzyme at the cell surface of osteoblasts. As of now, treatment of XLH patients is restricted to supplementation with oral inorganic phosphate (Pi) supplements in four or five divided doses per day, and co-administration of 1,25(OH)2D to compensate for the inappropriate synthesis of 1,25(OH)2D. Such high doses of phosphate frequently cause gastrointestinal intolerances, particularly diarrhea, leading to patient non-compliance. On the one hand, the phosphate load carries the risk of provoking secondary hyperparathyroidism (which may be severe enough to necessitate parathyroidectomy) while on the other hand, administration of excess 1,25(OH)2D may lead to hypercalciuria, hypercalcemia and nephrocalcinosis.

Useful ERT for XLH would therefore seek to replace the defective PHEX enzyme in XLH patients with a functional enzyme obtained through recombinant DNA technology. As the normal PHEX enzyme is anchored in osteoblast plasma membrane by a hydrophobic peptide, the natural form of PHEX cannot be produced and purified in sufficient quantities to be used in a pharmaceutical preparation. To circumvent the problem, a soluble form of recombinant PHEX (or sPHEX) was engineered and produced in cell cultures, purified and formulated for intravenous (IV) administration (WO 00/50580). sPHEX was then injected in Hyp mice, a mouse model for XLH, as described in co-pending U.S. application Ser. No. 10/362,259. Improvement of several bone related serum parameter were observed including a reduction of the abnormally high levels of serum alkaline phosphatase. Although these experiments were successful, it was believed that the efficacy of therapeutic sPHEX might be enhanced if the recombinant protein was modified so as to promote its binding to bone minerals.

There is therefore a need for means to successfully target proteins to bone matrix.

Biphosphonates are known to present high affinity binding to hydroxyapatite (HA), and has been used to target small molecules (4) and proteins (5) to bones. However this strategy requires chemical modifications of the purified proteins, and presents several disadvantages including possible interference with protein activity and additional purification steps.

Another strategy to target small molecules to bone has been to conjugate these entities to acidic peptides such as poly-Asp (6). This strategy was developed after the observation that several proteins synthesized by osteoblasts, the bone forming cells, bind to bone matrix through sequences particularly rich in acidic amino acid residues (Asp and Glu). This is the case of osteopontin (7) and bone sialoprotein, two noncollagenous proteins. Hence acidic peptides ($E_{2-10}$ and $D_{2-10}$) were used to target small molecules (i.e. methotrexate, FITC, Fmoc, biotin, estradiol) to hydroxyapatite in vitro. Acidic peptides ($E_6$ and $D_{6-10}$) were used to target small molecules (i.e. FITC, Fmoc, estradiol) to hydroxyapatite in vivo. Finally, $E_6$ was shown to confer to BSA, hemoglobin and IgG the ability to bind hydroxyapatite in vitro. In all the above cases, linking of the acidic sequence was performed chemically.

The present invention seeks to meet these needs and other needs.

The present description refers to a number of documents, the content of which is herein incorporated by reference in their entirety.

SUMMARY OF THE INVENTION

The present invention shows that large and complex molecules such as proteins can be fused with acidic peptides to successfully target bone in vivo.

According to a specific embodiment of the present invention there is provided a bone delivery conjugate having a structure selected from the group consisting of: A) X-Dn-Y-protein-Z; and B) Z-protein-Y-Dn-X, wherein X is absent or is an amino acid sequence of at least one amino acid; Y is absent or is an amino acid sequence of at least one amino acid; Z is absent or is an amino acid sequence of at least one amino acid; and Dn is a poly aspartate wherein n=10 to 16. In an other specific embodiment of the present invention, the protein in the bone delivery conjugate is a soluble phosphate regulating gene with homology to endopeptidases on the X chromosome (sPHEX). In an other specific embodiment of the present invention, the structure of the conjugate is: X-Dn-Y-sPHEX-Z. In other specific embodiment of the present invention, the sPHEX has a sequence selected from the group consisting of amino acids 46 to 749 of FIG. 10; 47 to 749 of FIG. 10; 48 to 749 of FIG. 10; 49 to 749 of FIG. 10; 50 to 749 of FIG. 10; 51 to 749 of FIG. 10; 52 to 749 of FIG. 10; 53 to 749 of FIG. 10; and 54 to 749 of FIG. 10. In a specific embodiment of these bone delivery conjugates, n is 10. In an other specific embodiment of this bone delivery conjugate, n is 11. In an other specific embodiment of this bone delivery conjugate, n is 12. In an other specific embodiment of this bone delivery conjugate, n is 13. In an other specific embodiment of this bone delivery conjugate, n is 14. In an other specific embodiment of this bone delivery conjugate, n is 15. In an other specific embodiment of this bone delivery conjugate, n is 16. In a more specific embodiment of the present invention, the sPHEX consists of the sequence of amino acids 46 to 749 of FIG. 10 and n=10.

In another specific embodiment of the present invention, the protein in the conjugate is a soluble alkaline phosphatase (sALP). In an other specific embodiment, the structure of the conjugate is: Z-sALP-X-Dn-Y. In an other specific embodiment, sALP is encoded by the sequence as set forth in FIG. 16A. In an other specific embodiment, sALP has the sequence as set forth in FIG. 16B. In a specific embodiment of these bone delivery conjugates, n is 10. In an other specific embodiment of this bone delivery conjugate, n is 11. In an other specific embodiment of this bone delivery conjugate, n is 12. In an other specific embodiment of this bone delivery conjugate, n is 13. In an other specific embodiment of this bone delivery conjugate, n is 14. In an other specific embodiment of this bone delivery conjugate, n is 15. In an other specific embodiment of this bone delivery conjugate, n is 16. In a more specific embodiment, n=10.

There is also provided an isolated nucleic acid molecule comprising a polynucleotide sequence selected from the group consisting of: a polynucleotide encoding a polypeptide comprising an amino acid sequence as set forth in FIG. 8; a polynucleotide encoding a polypeptide comprising an amino acid sequence as set forth in FIG. 11; a polynucleotide comprising the nucleotide sequence as set forth in FIG. 7; a nucleotide sequence completely complementary to any of the nucleotide sequences in (a), (b) or (c); and a nucleotide sequence which hybridizes under high stringency conditions to any of the nucleotide sequences in (a), (b), (c) or (d), wherein the high stringency conditions comprise: pre-hybridization and hybridization in 6×SSC, 5× Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

There is also provided a recombinant vector comprising said sequence. There is also provided a recombinant host cell comprising said vector.

There is also provided an isolated nucleic acid molecule comprising a polynucleotide sequence selected from the group consisting of: a polynucleotide comprising the nucleotide sequence as set forth in FIG. 17A; a polynucleotide encoding a polypeptide comprising an amino acid sequence as set forth in FIG. 17B; a nucleotide sequence completely complementary to any of the nucleotide sequences in (a) or (b); and a nucleotide sequence which hybridizes under high stringency conditions to any of the nucleotide sequences in (a), (b) or (c), wherein the high stringency conditions comprise: pre-hybridization and hybridization in 6×SSC, 5× Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

There is also provided an isolated nucleic acid molecule encoding a functional soluble PHEX comprising a polynucleotide sequence selected from the group consisting of: a polynucleotide encoding a sPHEX comprising amino acids 54 to 749 as set forth in FIG. 10; a polynucleotide encoding a sPHEX comprising amino acids 53 to 749 as set forth in FIG. 10; a polynucleotide encoding a sPHEX comprising amino acids 52 to 749 as set forth in FIG. 10; a polynucleotide encoding a sPHEX comprising amino acids 51 to 749 as set forth in FIG. 10; a polynucleotide encoding a sPHEX comprising amino acids 50 to 749 as set forth in FIG. 10; a polynucleotide encoding a sPHEX comprising amino acids 49 to 749 as set forth in FIG. 10; a polynucleotide encoding a sPHEX comprising amino acids 48 to 749 as set forth in FIG. 10; a polynucleotide encoding a sPHEX comprising amino acids 47 to 749 as set forth in FIG. 10; a polynucleotide encoding a sPHEX comprising amino acids 46 to 749 as set forth in FIG. 10; a nucleotide sequence completely complementary to any of the nucleotide sequences in (a) to (i); and a nucleotide sequence which hybridizes under high stringency conditions to any of the nucleotide sequences in (a) to (j), wherein the high stringency conditions comprise: pre-hybridization and hybridization in 6×SSC, 5× Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes. In an other embodiment, the isolated nucleic acid molecule further comprises at its 5' end, a polynucleotide encoding a poly-aspartate selected from the group consisting of $D_{10}$ to $D_{16}$.

There is also provided an isolated sPHEX polypeptide comprising a sequence selected from the group consisting of: amino acids 54 to 749 as set for in FIG. 10; amino acids 53 to 749 as set for in FIG. 10; amino acids 52 to 749 as set for in FIG. 10; amino acids 51 to 749 as set for in FIG. 10; amino acids 50 to 749 as set for in FIG. 10; amino acids 49 to 749 as set for in FIG. 10; amino acids 48 to 749 as set for in FIG. 10; amino acids 47 to 749 as set for in FIG. 10; and amino acids 46 to 749 as set for in FIG. 10.

There is also provided a bone delivery composition comprising a bone delivery conjugate of the present invention, and a pharmaceutically acceptable carrier.

There is also provided a method of delivering a protein to bone tissue of a mammal comprising administering to said mammal an effective amount of a bone delivery conjugate as recited of the present invention.

There is also provided a method of delivering sPHEX to bone tissue of a mammal comprising administering to said mammal an effective amount of a bone delivery conjugate of the present invention.

There is also provided a method of delivering ALP to bone tissue of a mammal in need thereof comprising administering to said mammal an effective amount of a bone delivery conjugate of the present invention.

There is also provided a method of treating a condition or disease related to a bone defect characterized by a lack of or an insufficient amount of functional phosphate regulating gene with homology to endopeptidases on the X chromosome (PHEX) comprising administering to a mammal in need thereof a conjugate of the present invention, said conjugate being in a pharmaceutically acceptable carrier. In specific embodiments, the condition or disease is X-linked hypophosphatemic rickets (XLH).

There is also provided a method of treating a condition or disease related to a bone defect characterized by a lack of or an insufficient amount of functional alkaline phosphatase comprising administering to a mammal in need thereof a conjugate of the present invention, said conjugate being in a pharmaceutically acceptable carrier. In specific embodiments, the condition or disease is hypophosphatasia.

There is also provided a method of screening peptides for use in a bone delivery protein-peptide conjugate comprising the steps of: fusing a candidate peptide to a reporter protein to form a protein-peptide conjugate; contacting the conjugate with bone tissue or mineral phase of bone; and wherein the candidate peptide is selected when the presence of the reporter protein on bone tissue or mineral phase of bone is higher when it is conjugated with the candidate peptide than when it is not.

According to a specific embodiment of the present invention there is provided a bone delivery conjugate of a protein fused to a peptide selected from the group consisting of deca-aspartate ($D_{10}$) to hexadeca-aspartate ($D_{16}$).

In specific embodiments of conjugates of the present invention, the sPHEX is fused at its N-terminal to $D_{10}$. In an other specific embodiment, the sPHEX is fused at its N-terminal to $D_{11}$. In an other specific embodiment, the sPHEX is fused at its N-terminal to $D_{12}$. In an other specific embodiment, the sPHEX is fused at its N-terminal to $D_{13}$. In an other specific embodiment, the sPHEX is fused at its N-terminal to $D_{14}$. In an other specific embodiment, the sPHEX is fused at its N-terminal to $D_{15}$. In an other specific embodiment, the sPHEX is fused at its N-terminal to $D_{16}$.

According specific embodiments of conjugates of the present invention, the sALP is fused at its C-terminal to $D_{10}$. In an other specific embodiment, the sALP is fused at its C-terminal b $D_{11}$. In an other specific embodiment, the sALP is fused at its C-terminal to $D_{12}$. In an other specific embodiment, the sALP is fused at its C-terminal to $D_{13}$. In an other specific embodiment, the sALP is fused at its C-terminal to $D_{14}$. In an other specific embodiment, the sALP is fused at its C-terminal to $D_{15}$. In an other specific embodiment, the sALP is fused at its C-terminal to $D_{16}$.

It is understood that any functional soluble protein may be used in the conjugate of the present invention. Although results for conjugates comprising one specific sPHEX or sALP of the present invention are presented herein, it is understood that any other functional sPHEX or sALP may be so used.

sPHEX

As used herein sPHEX means any soluble biologically active fragment of PHEX or mutein thereof. Those of skill in the art may prepare expression constructs other than those expressly described herein for optimal production of sPHEX in suitable cell lines transfected therewith. Moreover, skilled artisans may design fragments of cDNA encoding soluble biologically active fragments and muteins of the naturally occurring PHEX which possess the same or similar biological activity to the naturally occurring full-length enzyme.

To create a recombinant source for sPHEX, a large series of expression vectors may be constructed and tested for expression of a PHEX cDNA. Based on transient transfection experiments, as well as stable transfections, an expression construct may be identified that provides a particularly high level of expression.

Without being so limited, any sPHEX comprising at least a native PHEX ectodomain portion starting with the cysteine at position 54 of the sequence presented at FIG. 10 is encompassed by the present invention.

The conjugates according to specific embodiments of the present invention thus are any sPHEX comprising this 54-749 fragment of the native PHEX, preferably the 53-749 native fragment, more preferably the native 52-749 fragment, more preferably the native 51-749 fragment, more preferably the 50-749 native fragment, more preferably the 49-749 native fragment, more preferably the 48-749 native fragment, more preferably the 47-749 native fragment, and more preferably the 46-749 native fragment, along with a poly-aspartate selected from the group consisting of $D_{10}$ to $D_{16}$ fused immediately upstream of this fragment.

The conjugate may further optionally comprise one or more additional amino acids 1) upstream from the poly-aspartate; and/or 2) between the poly-aspartate and the native fragment or functional equivalent. These amino acids may be any amino acid. According to specific embodiments, they may be selected independently from the group consisting of any amino acid except for cysteine, proline and tryptophan namely those amino acids known to induce disulfide bond formation or changes in conformation.

These amino acids may be present in the conjugate when for instance the cloning strategy used to produce it introduces them in these locations.

According to specific cloning strategies, amino acids located upstream of the poly-aspartate in the recombinant cleavable PHEX can be selected according to known parameters so as to provide an adequate substrate for specific enzymes of the secretory pathway (e.g. furin or signal peptidase) of the host cell that will be used to cleave the produced recombinant cleavable PHEXs into a secreted bone targeting sPHEX. The likelihood of a designed sequence being cleaved by the signal peptidase of the host cell can be predicted by an appropriate computer algorithm such as that described in Bendtsen et al. (J Mol Biol. 2004 Jul. 16; 340(4):783-95) and available on the Web at www.cbs.dtu.dk/services/SignalP/ which takes into account parameters including the following: the amino acids at position −3 and −1 from the cleavage site by the signal peptidase desirably have small and non charged side chains. Preferably, at position −1: Ala, Ser, Gly, Cys, Thr and occasionally Gln, Pro, and Leu. Similarly those at position −3 should preferably be: Ala, Ser, Gly, Cys, Thr, Ile, Leu, Val. Moreover, amino acids in position −6 and −4 from the cleavage site are desirably those capable of inducing the formation of a beta-turn (such as Pro) residues.

The present invention hence encompasses conjugates comprising additional amino acids that may be selected on the basis of the cloning strategy used to produce a cleavable recombinant PHEX. Hence the cleavable recombinant PHEX disclosed in Examples 3 and 4 below contains such additional amino acids upstream of the poly-aspartate and between the poly-aspartate and the native ectodomain sequence. Also, the present invention encompasses a conjugate comprising the secPHEX disclosed in co-pending application no. WO 02/15918 prepared by fusing NL-1 N-terminal fragment comprising a furin site to the PHEX native ectodomain with the vector pCDNA3/RSV/NL-1-PHEX, and a secPHEX comprising an immunoglobulin fragment at its N-terminal. More particularly, FIG. 12 schematically presents the structure of secPHEXs that comprise additional amino acids upstream of the native 46-749 PHEX ectodomain fragment. Constructs no. 1 to 3 and 5 could be fused to a poly-aspartate and be used as conjugates of the present invention. Construct no. 4 constitutes a conjugate of the present invention: it comprises a $D_{10}$ poly-aspartate and a native ectodomain fragment.

The conjugates of the present invention further also encompass sPHEXs comprising deletions at their C-terminal non detrimental to their enzymatic activity.

Furthermore, the present invention comprises conjugates wherein the poly-aspartate would be attached at the C-terminal of the native PHEX ectodomain fragment.

sALP

ALP is a membrane-bound protein anchored through a glycolipid to its C-terminal. This glycolipid anchor (GPI) is added post translationally after removal of a hydrophobic C-terminal end which serves both as transitional membrane anchor and as a signal for the addition of the GPI. Hence the sALP used in Example 6 herein is constituted of an ALP wherein the first amino acid of the hydrophobic C-terminal sequence, namely alanine, is replaced by a stop codon. The soluble ALP so formed contains all amino acids of the native and thus active anchored form of ALP.

The sALP conjugates according to specific embodiments of the present invention thus are any sALP along with a poly-aspartate selected from the group consisting of $D_{10}$ to $D_{16}$ fused immediately downstream of this fragment.

The conjugate may further optionally comprise one or more additional amino acids 1) upstream from the poly-aspartate; and/or 2) between the poly-aspartate and the native sALP fragment or functional equivalent. This is the case for instance when the cloning strategy used to produce the bone targeting conjugate introduces exogenous amino acids in these locations. However the exogenous amino acids should be selected so as not to provide an additional transamination site. The likelihood of a designed sequence being cleaved by the transaminase of the host cell can be predicted as described by Ikezawa (Biol Pharm. Bull. 2002, 25(4) 409-417).

The conjugates of the present invention further also encompass sALPs comprising deletions at their N-terminal non detrimental to their enzymatic activity.

Furthermore, the present invention comprises conjugates wherein the poly-aspartate would be attached at the N-terminal of the native ALP anchored fragment or its biologically active fragment.

The term "recombinant protein" is used herein to refer to a protein encoded by a genetically manipulated nucleic acid inserted into a prokaryotic or eukaryotic host cell. The nucleic acid is generally placed within a vector, such as a plasmid or virus, as appropriate for the host cell. Although E. coli has been used as a host for expressing the conjugates of the present invention in the Examples presented herein, a person of ordinary skill in the art will understand that a number of other hosts may be used to produce recombinant proteins according to methods that are routine in the art. Representative methods are disclosed in Maniatis, et al. Cold Springs Harbor Laboratory (1989). "Recombinant cleavable protein" as used herein is meant to refer to a recombinant protein that may be cleaved by a host's enzyme so as to produce a secreted/soluble protein.

The term "ectodomain fragment" is meant herein when used in relation to PHEX is meant to refer to PHEX's fragment that is located outside of the cellular membrane when found in its native form.

The term "bone tissue" is used herein to refer to tissue synthesized by osteoblasts composed of an organic matrix containing mostly collagen and mineralized by the deposition of hydroxyapatite crystals.

The fusion proteins comprised in the bone delivery conjugates of the present invention are useful for therapeutic treatment of bone defective conditions by providing an effective amount of the fusion protein to the bone. The fusion protein is provided in the form of a pharmaceutical composition in any standard pharmaceutically acceptable carrier, and is administered by any standard procedure, for example by intravenous injection.

The term "pharmaceutically acceptable carrier" is used herein to refer, when parenteral administration is elected as the route of administration, to pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous solvents include water; water-alcohol solutions; physiological saline; buffered medical parenteral vehicles including sodium chloride solution, Ringer's dextrose solution, dextrose plus sodium chloride solution, fluid and nutrient replenishers; electrolyte replenishers; Ringer's solution containing lactose, or fixed oils.

The term "effective amount" is used herein to refer to the minimal amount of a pharmaceutical composition that should be administered to a mammal in order to achieve a significant therapeutic effect. The dosages will depend on many factors including the mode of administration. Typically, the amount of protein contained within a single dose will be an amount that effectively prevents, delays or treats bone related undesired condition without inducing significant toxicity. In particular, an effective amount of the conjugate and compositions of the present invention will comprise an amount of fusion protein which will cause a significant alleviation of clinical symptoms of the condition.

The effective amount may be given daily, weekly, monthly or fractions thereof. Typically, a pharmaceutical composition of the invention can be administered in an amount from about 0.001 mg up to about 500 mg per kg of body weight per day (e.g., 10 mg, 50 mg, 100 mg, or 250 mg). Dosages may be provided in either a single or multiple dosage regimen. For example, in some embodiments the effective amount is a dose that ranges from about 1 mg to about 25 grams of the conjugate to be targeted to bone per day, from about 50 mg to about 10 grams of the conjugate to be targeted to bone per day, from about 100 mg to about 5 grams of the conjugate to be targeted to bone per day, about 1 gram of the conjugate to be targeted to bone per day, about 1 mg to about 25 grams of the conjugate to be targeted to bone per week, about 50 mg to about 10 grams of the conjugate to be targeted to bone per week, about 100 mg to about 5 grams of the conjugate to be targeted to bone every other day, and about 1 gram of the conjugate to be targeted to bone once a week.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In addition, patients may be taking medications for other diseases or conditions. The other medications may be continued during the time that the protein for delivery to bone is given to the patient, but it is particularly advisable in such cases to begin with low doses to determine if adverse side effects are experienced.

The term "high stringency conditions" are meant to refer to conditions enabling sequences with a high homology to bind. Without being so limited, examples of such conditions are listed In the handbook *"Molecular cloning, a laboratory manual"*, second edition of 1989 from Sambrook et al.: 6×SSC or 6×SSPE, Denhardt's reagent or not, 0.5% SDS and the temperature used for obtaining high stringency conditions is most often in around 68° C. (see pages 9.47 to 9.55 of Sambrook) for nucleic acid of 300 to 1500 nucleotides. Although the optimal temperature to be used for a specific nucleic acid probe may be empirically calculated, and although there is room for alternatives in the buffer conditions selected, within these very well known condition ranges, the nucleic acid captured will not vary significantly. Indeed, Sambrook clearly indicates that the "choice depends to a large extent on personal preference" (see page 9.47). Sambrook specifies that the formula to calculate the optimal temperature which varies according to the fraction of guanine and cytosine in the nucleic acid probe and the length of the probe (10 to 20° C. lower than $T_m$ wherein $T_m$=81.5° C.+16.6($\log_{10}$[Na$^+$])+0.41(fraction G+C)−0.63(% formamide−(600/l)) (see pages 9.50 and 9.51 of Sambrook).

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIG. 7 shows the nucleotide sequence of a recombinant DNA sequence encoding a protein cleavable so as to produce $D_{10}$-sPHEX (SEQ ID NO: 1);

FIG. 8 shows the amino acid sequence encoded by the $D_{10}$-sPHEX of FIG. 7 (SEQ ID NO: 2);

FIG. 10 shows the nucleotide sequence of a native (or membrane-bound) PHEX (SEQ ID NO: 3);

FIG. 11 shows the amino acid sequence (SEQ ID NO: 4) of a $D_{10}$-sPHEX conjugate produced by cleavage of the recombinant cleavable protein of FIG. 8;

FIG. 12 schematically illustrates the structure and activities of various secPHEX constructs;

Figure 15:
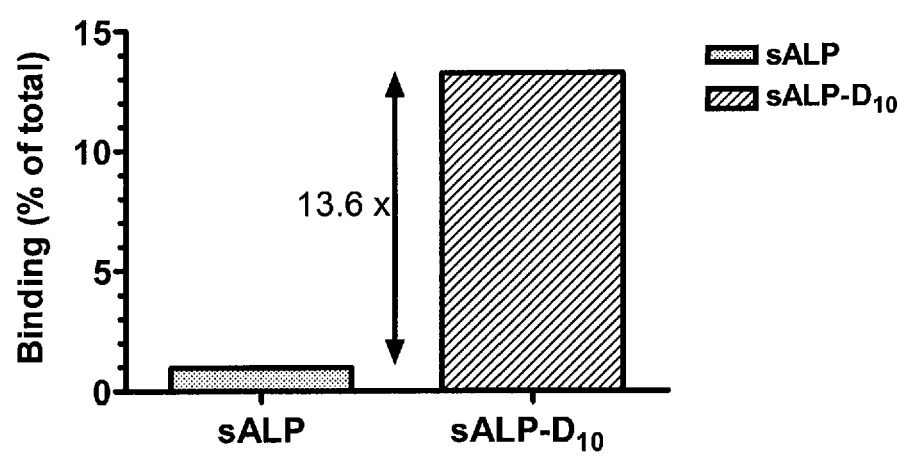
Figure 18:
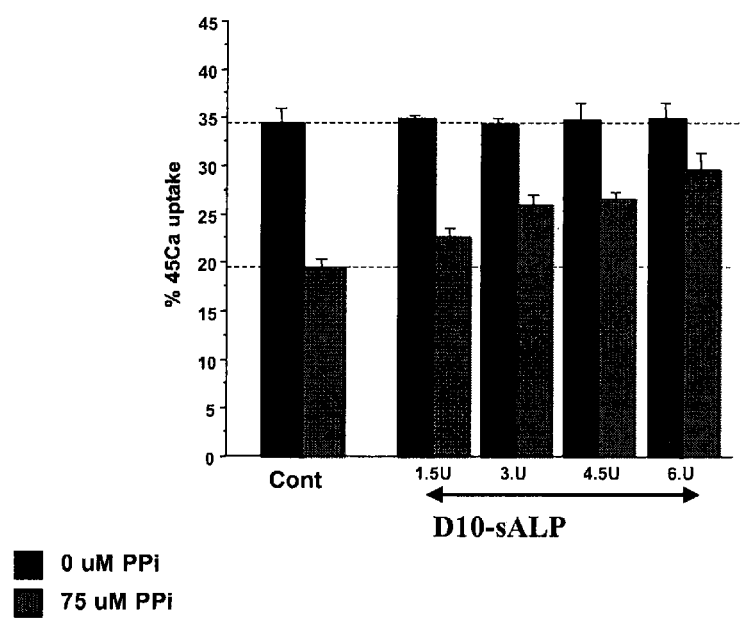

FIG. 15 graphically shows the binding to bone mineral phase of a deca-aspartate fused to secreted alkaline phosphatase;

FIG. 16 shows A. the nucleotidic sequence (SEQ ID NO: 5) of a soluble alkaline phosphatase; and B. the amino acid sequence (SEQ ID NO: 6) of that soluble alkaline phosphatase;

FIG. 17 shows A. the nucleotidic sequence (SEQ ID NO: 7) encoding a conjugate of the present invention, namely sALP-$D_{10}$; and B. the amino acid sequence (SEQ ID NO: 8) of that conjugate; and FIG. 18 graphically shows the effect of D10-sALP on PPi-mediated mineralization inhibition.

DESCRIPTION OF ILLUSTRATIVE EMBODIMENTS

The present invention showed that specific poly-aspartic peptides fused in frame to a protein, as exemplified herein by the gluthatione-S-transferase protein (GST), used as a reporter protein, by sPHEX and by sALP, can significantly increase the bone binding capacity of these proteins.

The present invention is illustrated in further details by the following non-limiting examples.

Table 1 presents the sequence of oligonucleotides used in Examples 1 to 7.

TABLE 1

SEQUENCE OF SYNTHETIC OLIGONUCLEOTIDES USED IN EXAMPLES 1 TO 7

| | | |
|---|---|---|
| $D_6$ | SEQ ID NO: 9. | 5'-GATCCGATGACGATGACGATGACGC-3' |
| | SEQ ID NO: 10. | 5'-GGCCGCGTCATCGTCATCGTCATCG-3' |
| $D_{10}$ | SEQ ID NO: 11. | 5'-GATCCGATGACGATGACGATGACGATGACGATGACGC-3' |
| | SEQ ID NO: 12. | 5'-GGCCGCGTCATCGTCATCGTCATCGTCATCGTCATCG-3' |
| $D_{16}$ | SEQ ID NO: 13. | 5'-GATCCGATGACGATGACGATGACGATGACGATGACGATGACGATGACGC-3' |
| | SEQ ID NO: 14. | 5'-GGCCGCGTCATCGTCATCGTCATCGTCATCGTCATCGTCATCGTCATCG-3' |
| hMEPE | SEQ ID NO: 15. | 5'-GATCCGATGACAGTAGTGAGTCATCTGACAGTGGCAGTTCAAGTGAGAGCGATGGTGACGC-3' |
| | SEQ ID NO: 16. | 5'-GGCCGCGTCACCATCGCTCTCACTTGAACTGCCACTGTCAGATGACTCACTACTGTCATCG-3' |
| hStatherin | SEQ ID NO: 17. | 5'-GATCCGATTCATCTGAAGAGAAATTTTTGCGTAGAATTGGAAGATTCGGTGC-3' |
| | SEQ ID NO: 18. | 5'-GGCCGCACCGAATCTTCCAATTCTACGCAAAAATTTCTCTTCAGATGAATCG-3' |
| hMGP | SEQ ID NO: 19. | 5'-GATCCTGTTATGAATCACATGAAAGCATGGAATCTTATGAACTTAATCCCTTCATTGC-3' |
| | SEC ID NO: 20. | 5'-GGCCGCAATGAAGGGATTAAGTTCATAAGATTCCATGCTTTCATGTGATTCATAACAG-3' |
| hOsteopontin | SEQ ID NO: 21. | 5'-GATCCCAGAATGCTGTGTCCTCTGAAGAAACCAATGACTTTAAAGC-3' |
| | SEQ ID NO: 22. | 5'-GGCCGCTTTAAAGTCATTGGTTTCTTCAGAGGACACAGCATTCTGG-3' |
| hBSP2 | SEQ ID NO: 23. | 5'-GATCCGGCAGTAGTGACTCATCCGAAGAAAATGGAGATGACAGTTCAGAAGAGGAGGAGGAAGC 3' |
| | SEQ ID NO: 24. | 5'-GGCCGCTTCCTCCTCCTCTTCTGAACTGTCATCTCCATTTTCTTCGGATGAGTCACTACTGCCG-3' |
| hIGFBP5 | SEQ ID NQ: 25. | 5'-GATCCCGCAAAGGATTCTACAAGAGAAAGCAGTGCAAACCTTCCCGTGGCCGCAAGCGTGC-3' |
| | SEQ ID NO: 26. | 5'-GGCCGCACGCTTGCGGCCACGGGAAGGTTTGCACTGCTTTCTCTTGTAGAATCCTTTGCGG-3' |
| M81736 CBS | SEQ ID NO: 27. | 5'-AGTCGGGATCCGGAACAAGCAGCGTGTTCTAC-3' |
| | SEQ ID NO: 28. | 5'-AGATCGCGGCCGCTCAATTGTGCACGGTGTGATTAAAGG-3' |
| $D_{10}$ | SEQ ID NO: 29. | 5'-CCGGAGATGACGATGACGATGACGATGACGATGACT-3' |
| | SEQ ID NO: 30. | 3'-TCTACTGCTACTGCTACTGCTACTGCTACTGAGGCC-5' |

Example 1

Bone Binding of GST-$D_6$, GST-$D_{10}$ and GST-$D_{16}$

Recombinant DNA technology was used to generate a plasmid containing a nucleic acid encoding GST followed in frame by a nucleic acid encoding a $D_6$, $D_{10}$ or $D_{16}$ acidic peptide. To obtain the GST-$D_6$, GST-$D_{10}$ and GST-$D_{16}$ conjugates, the oligonucleotide of SEQ ID NO:9 (see Table 1) was first mixed with the oligonucleotide of SEQ ID NO:10, oligonucleotide of SEQ ID NO:11 mixed with oligonucleotide of SEQ ID NO:12, and oligonucleotide of SEQ ID NO:13 mixed with oligonucleotide of SEQ ID NO:14. This procedure generated duplex oligonucleotides coding for $D_6$, $D_{10}$ and $D_{16}$, respectively, and having extremities compatible with cloning in the pGEX3T-4 plasmid (Pharmacia biotechnology) pre-digested with restriction endonucleases BamHI and NotI. pGEX3T-4 vectors were transformed into AP401 protease minus *E. coli* bacteria strain (Ion::mini tetR ara-Δlac-pro naIA argEam rifR thiI [F' pro AB lacIq Z M15]).

Positive bacterial colonies were used to seed a 10 ml pre-culture of double YT media and 100 mg/litre ampicilin. Bacteria were grown overnight at 37° C. in an orbital shaker set at 250 rpm. The pre-culture was added to 500 ml of fresh double YT ampicilin media in a 2 litres Erlenmeyer flask. Bacteria were let to grow at 37° C. under orbital shaking until a 595 nm optical density of 0.7 was reached. Protein expression was then induced by adding 500 µl of 0.1 M IPTG solution and the bacteria put back to incubation for 2 hours. Bacteria were spun down at 8000×g for 10 minutes at 4° C. The pellet was suspended in 25 ml of ice-cold PBS containing Complete-EDTA caplet protease inhibitor (Boehringer Mannheim) and frozen at −20° C.

Figure 1:
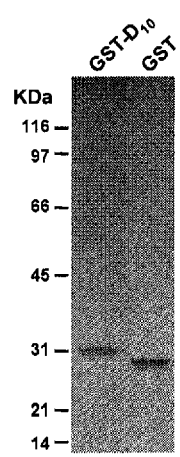
FIG. 1 presents the purity status of GST and GST-$D_{10}$ proteins on an SDS polyacrylamide gel after CL-4B chromatography.

Bacteria cells were thawed and disrupted on ice with 6 pulses of sonication every 50 seconds prior to centrifugation at 12000×g for 10 minutes at 4° C. Supernatant was mixed with 500 µl of GS-4B wet resin (Amersham Pharmacia Biotech) equilibrated with PBS. The resin was kept as a suspension during the overnight incubation at 4° C. The resin was rinsed with PBS until 280 nm optical density was below 0.01. Resin was then laid on an empty column and proteins eluted with 10 mM glutathione dissolved in PBS. The pooled elution fractions were dialyzed against 1 mM sodium $PO_4$ pH 7.4 and 150 mM NaCl. Dialyzed proteins were filtered in a sterile environment on 0.22 µm PES membrane and kept at 4° C. Typically 40 and 60 mg of pure proteins were recovered per litre of culture respectively. FIG. 1 shows an example of an SDS-PAGE analysis of the purified GST and GST-$D_{10}$. Purified proteins were iodinated using Iodo-Beads Iodination Reagent (Pierce).

GST and peptide-fused GST were dialyzed against PBS and concentration set to 2 mg/ml. Iodination reaction was initiated by adding 2 PBS-rinsed Iodo-Beads to 2 mCi of Na125I (100 µCi/µl, ICN) dissolved in 500 µl of PBS. Beads were incubated at room temperature for five minutes before adding 1 mg of dialyzed protein. The iodination reaction proceeded for 15 minutes before the bead was removed and rinsed in 500 ml of PBS. To the final 1.5 ml of iodinated protein solution, 15 µl of 6 mM NaI was added to dilute non-specific radioactivity. The mixture was then desalted using PD-10 gel filtration columns (Amersham Pharmacia Biotech) equilibrated with PBS. Proteins eluted in the void volume. They were concentrated and dialysed against the in vivo buffer (1 mM sodium PO4 pH 7.4 and 150 mM NaCl) using Centriprep-YM10™ cartridges (Amicon). Radioactivity was measured using a gamma radiation counter, protein concentration was assessed by the Bradford assay and $^{125}I$ chemical linkage to proteins was revealed by autoradiography of dried SDS-PAGE. Iodinated samples were kept at 4° C.

Bone Binding Ability of GST-Poly-Aspartic Peptides Fusion Proteins Compared to that of GST Alone The iodinated GST-fusion proteins were injected to mice under isoflurane anesthesia as an intravenous bolus through the subclavian vein. A dose of 1 mg of iodinated protein/per kg body weight was injected. The maximum dose volume was set at 10 ml/kg. Duration of treatment was sixty minutes. Ten and sixty minutes after injection, blood samples (0.1 to 0.2 ml) were collected via the subclavian vein under anesthesia into serum/gel clotting activator Microvette™ tubes (Sarstedt, #20.1291). At necropsy, blood samples were collected and animals were sacrificed by exsanguination from the heart under isoflurane anesthesia. Organs (kidneys, liver, femurs, tibias and thyroid) were collected, rinsed in saline 0.9% USP, blotted on gauze and transferred into gamma counter tubes. Serum samples and organs were weighted and radioactivity was measured. Results were expressed as percentage of injected dose. Neither $D_{10}$-GST nor $D_{16}$-GST promoted binding to other organs than bone. This showed the specificity of these conjugates to bone (Data not shown).

Figure 2:
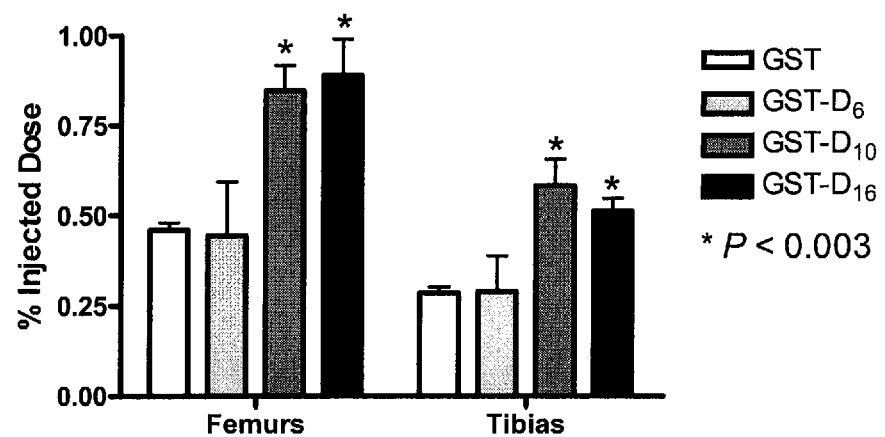
FIG. 2 shows the promotion of GST binding to bone by $D_6$, $D_{10}$ and $D_{16}$ peptide motifs through the percentage of the injected dose of recombinant GST found associated with specific tissues.

FIG. 2 shows that GST-$D_6$ fusion protein did not bind more to tibia or femur than GST alone. In contrast, $D_{10}$ and $D_{16}$ peptide motifs promoted GST binding to bones.

The fact that $D_6$, a peptide shown to successfully deliver small molecules to bone could not successfully deliver a protein, namely GST, to bone shows that it is not predictable whether a specific acidic peptide known to effectively deliver a small molecule to bone will also be effective in delivering a protein to bone.

Example 2

Binding Ability of GST Fused with Various Peptides

Human matrix extracellular phosphoglycoprotein (hMEPE) is a protein synthesized by osteoblasts that shows major similarities to a group of bone and teeth mineral matrix phosphor-glycoproteins, proteins known to naturally bind to bone matrix (8). Of particular importance, hMEPE presents at its carboxy-terminus a sequence of 18 amino acid residues (DDSSESSDSGSSSESDGD) (SEQ ID NO: 31) similar to acidic peptides found in dentin phosphorin and dentin sialophosphoprotein, both known to bind to bone matrix (8).

Human Statherin (hStatherin) is a protein synthesized by salivary glands, which similarly to histatin directly modulates hydroxyapatite nucleation and/or growth. Of particular importance, hStatherin presents a sequence of 15 amino acid residues at positions 20 to 34 (DSSEEKFLRRIGRFG) (SEQ ID NO: 32) that was shown to bind tightly to hydroxyapatite (9).

Human Matrix Gla Protein (hMGP) is a protein synthesized by vascular smooth muscle cells and chondrocytes that functions as an inhibitor of hydroxyapatite polymerization by binding to crystal nuclei. Of particular importance, hMGP presents at its amino-terminus a sequence of 17 amino acid residue at positions 19 to 35 of the open reading frame (CYESHESMESYELNPFI) (SEQ ID NO: 33) similar to phosphorylated gamma carboxyglutamic acidic peptides found in osteocalcin known to bind to bone matrix, and thought to promote binding to bone matrix (10).

Human osteopontin (hOPN) is a protein synthesized by osteoblasts that regulates hydroxyapatite crystal growth. This protein belongs to the bone sialophosphoprotein family. Of particular importance, hOPN presents a sequence of 13 amino acid residue (QNAVSSEETNDFK) (SEQ ID NO: 34) at positions 58 to 70 of the open reading frame. This sequence shows a high level of homology among mammal species. Secondary structure prediction makes this sequence appropriate to solvent exposure and this sequence was shown to be phosphorylated at its serine residues. This latter characteristic is thought to affect binding to bone matrix (11).

Human Bone SialoProtein II (hBSP2) is a protein synthesized by osteoblasts that shows major similarities to a group of bone and teeth mineral matrix phosphor-glycoproteins, proteins known to naturally bind to bone matrix. Of particular importance, hBSPII presents at its amino-terminus a sequence of 18 amino acid residues at positions 62 to 79 of the open reading frame (GSSDSSEENGDDSSEEEE) (SEQ ID NO: 35) similar to acidic peptides found in dentin phosphorin and MEPE, and thought to promote binding to bone matrix (8).

Human Insulin-like Growth Factor binding protein-5 (hIGFBP5) is synthesized by osteoblasts. This protein, similarly to proteins of the IGFBP family, is thought to regulate osteoblast function in the bone remodeling process. Of particular importance, hIGFBP5 presents a sequence of 18 amino acid residues at positions 221 to 238 of the open reading frame (RKGFYKRKQCKPSRGRKR) (SEQ ID NO: 36) that was shown to bind tightly to hydroxyapatite (12).

*Staphylococcus aureus* collagen adhesin (M81736) is a protein expressed at the surface of *S. aureus* that promotes bacteria binding to collagen matrix of mammalian bone and cartilageneous tissues. Such a binding was reported to be instrumental in the development of pathogenesis such as osteomyelitis and infectious arthritis. Of particular importance, the collagen binding domain (CBS) of this adhesin was reported to encompass 151 amino acid residues (G168 to N318) of the open reading frame of the protein (13, 14). The amino acid primary sequence being the following:

(SEQ ID NO: 37)
GTSSVFYYKTGDMLPEDTTHVRWFLNINNEKSYVSKDITIKDQI

QGGQQLDLSTLNINVTGTHSNYYSGQSAITDFEKAFPGSKITVDNTKNTI

DVTIPQGYGSYNSFSINYKTKITNEQQKEFVNNSQAWYQEHGKEEVNGKS

FNHTVHN.

Plasmids containing the acidic peptide sequences derived from hMEPE, hStatherin, hMGP, hOPN, hBSP2, hIGFBP5 and CBS following GST in frame were constructed to determine whether they could promote bone targeting of a recombinant protein. Recombinant DNA technology as described in Example 1 was used to generate plasmids for hMEPE, hStatherin, hMGP, hOPN, hBSP2 and hIGFBP5 derived peptides. The oligonucleotide pairs identified in Table 1 for each of these peptides were mixed to obtain the corresponding GST-acidic peptide fusion protein. This procedure generated duplex oligonucleotides coding for these acidic peptides and having extremities compatible with cloning in the pGEX3T-4 (Pharmacia biotechnology) plasmid pre digested with restriction endonucleases BamHI and NotI.

A CBS-containing plasmid was constructed as follows. A synthetic gene corresponding to the CBS sequence was obtained from Bio S&T (Montreal) and inserted in plasmid pLIV Select. Oligonucleotides of SEQ ID NO: 27 and 28 were used as primers in PCR reactions with plasmid pLIV Select containing the CBS gene to amplify the CBS specific sequences. pGEX-4T-3 vectors were transformed into AP401 protease minus *E. coli* bacteria strain (Ion::mini tetR ara-Δlac-pro naIA argEam rifR thiI [F' pro AB lacIq Z M15]).

Protein production and purification, and pharmacodistribution of the iodinated fusion protein were performed as described in Example 1.

None of these GST-acidic peptides was shown to bind to bones (result not shown).

The fact that the peptide derived from statherin, a peptide shown to successfully deliver a small portion of osteopontin to bone, could not successfully deliver the GST protein to bone shows that it is not predictable whether a specific acidic peptide known to effectively deliver a small peptide to bone will also be effective in delivering a protein to bone.

Example 3

$D_{10}$ Increases sPHEX's Ability to Correct Alkaline Phosphatase Levels in Mice PHEX is a metallopeptidase that is widely believed to control the level of bone peptide factors involved in the regulation of mineralization and kidney phosphate homeostasis. PHEX is expressed at the surface of osteoblasts and osteocytes in contact with or imbedded in the bone matrix. This example provides data on the design, production and purification of an extended form of sPHEX containing at its N-terminus a sequence of 10 aspartic acid residues designed to anchor itself to the bone matrix.

$D_{10}$sPHEX Expression Vector

A BspEI endonuclease restriction site was inserted by site directed mutagenesis (QuickChange, Stratagene) into the pCDNA3-RSV-sPHEX-NEO vector (Boileau G. et al., Biochem. J. (2001) 355, 707-13) using the following oligonucleotide primers:

(SEQ ID NO: 38)
5'-CAGTCAAGGTCTCTTA<u>TCCGGA</u>AGTCTCCAAGCTAAACAGG-3'
and (SEQ ID NO: 39)
5'-CTGTTTAGCTTGGAGACT<u>TCCGGA</u>TAAGAGACCTTGACTGG-3'.

The hexamer BspEI sequence (underlined) was inserted in frame with and upstream of the sPHEX DNA sequence. This construct encodes a recombinant protein which is cleavable between the leucine and serine at positions 41 and 42, respectively in FIG. 8. It is constituted therefore of two exogenous amino acids, followed downstream by a deca-aspartate, which is in turn followed by two additional exogenous amino acids. These 4 exogenous amino acids derive from the cloning strategy used to produce the conjugate. These exogenous amino acids were shown not to defeat the enzymatic activity of the conjugate (See FIG. 12 showing the specific activity of this construct) but may be dispensed with. Downstream of these exogenous amino acids is an ectodomain fragment of the native PHEX starting therefore with the serine at position 46 of the sequence presented in FIG. 10. The modified pCDNA3-RSV-NEO vector was cleaved with BspEI and then digested with alkaline phosphatase to remove the 5' phosphate moieties.

Figure 3:
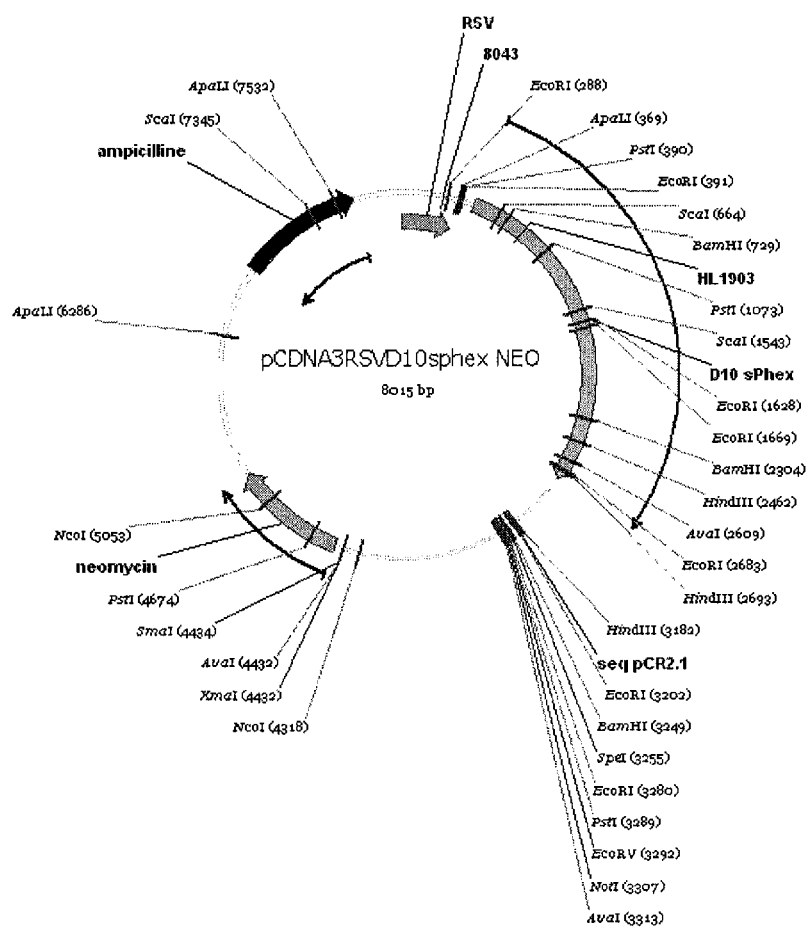
FIG. 3 provides a schematic representation of the plasmid pCDNA3-RSV-$D_{10}$sPHEX-NEO vector.

An oligonucleotide duplex coding for deca-aspartate: [5'-CCGGAGATGACGATGACGATGACGATGAC-GATGACT-3' (SEQ ID NO: 29) and 3'-TCTACTGC-TACTGCTACTGCTACTGCTACTGAGGCC-5' (SEQ ID NO: 30)] was first phosphorylated on its 5' ends with T4 polynucleotide kinase and ligated to the BspEI digested vector. This yielded the pCDNA3-RSV-$D_{10}$sPHEX-NEO vector (FIG. 3). This vector comprised the sequence presented in FIG. 7 which encodes the recombinant cleavable PHEX having the amino acid sequence presented in FIG. 8.

Expression of Recombinant $D_{10}$sPHEX

To induce the stable expression of the $D_{10}$sPHEX protein, the pCDNA3-RSV-$D_{10}$sPHEX-NEO vector was transfected in LLC-PK1 cells (Porcine Kidney cells; ATCC No. CRL-1392) using the Lipofectamine-Plus™ liposome transfection kit (Invitrogen). Transfected cells were selected by adding 400 µg/ml G-418 (Life Technologies) to the medium. Clones of G-418 resistant cells were screened for $D_{10}$sPHEX expression using the PHEX fluorescent enzymatic assay [Campos M. et al. Biochem. J. (2003) 373, 271-9]. The apparent molecular weight of the protein recovered in the spent medium was estimated by immunoblotting using a monoclonal antibody raised against a recombinant human PHEX fragment (K121-E294) as described previously (Ruchon A F et al. J. Bone Miner. Res. (2000) 15, 1440-1450). A G-418 resistant clone expressing 1 to 2 mg of D10sPHEX per litre was used for protein production. Cells were seeded in Cellstack-10™ (Corning) at a density of $7 \times 10^7$ in 1.75 litres of media (199 media, 6% FBS, 1 mM NaPyruvate, Penicillin $1 \times 10^5$ U/litre, Streptomycin 100 mg/litre and 1% G-418. $D_{10}$sPHEX expression was increased by incubating the cells in 1.75 litre of DMEM+10 mM sodium butyrate for four days at 37° C. and 5% $CO_2$ prior to harvest of the spent medium.

Purification and Characterization

Figure 4:
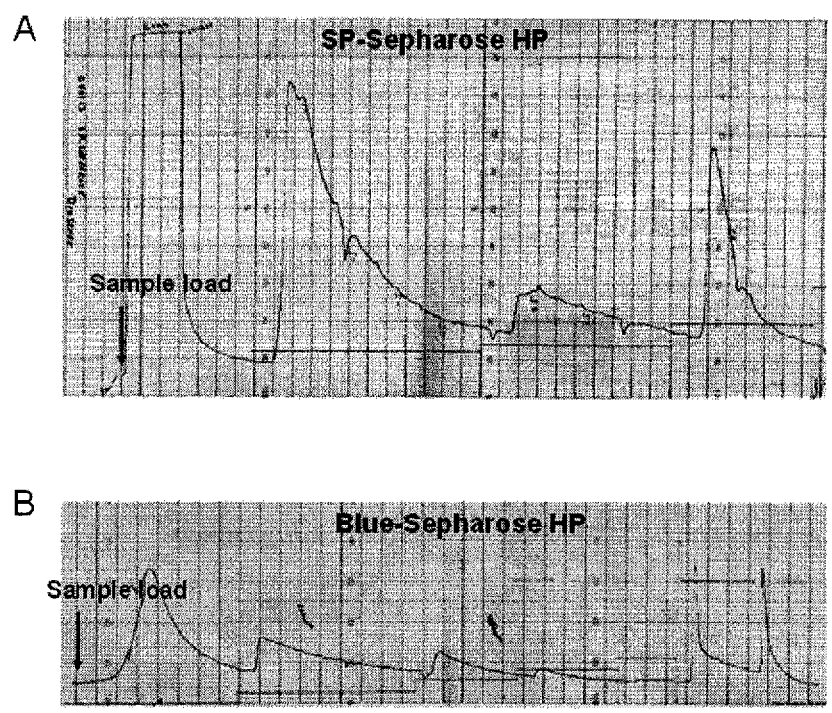
FIG. 4 presents a chromatographic profile of 280 nm detection of PHEX flow for the SP-Sepharose™ HP (A) and the blue-Sepharose HP (B). Straight line represents buffer ratio.
Figure 5:
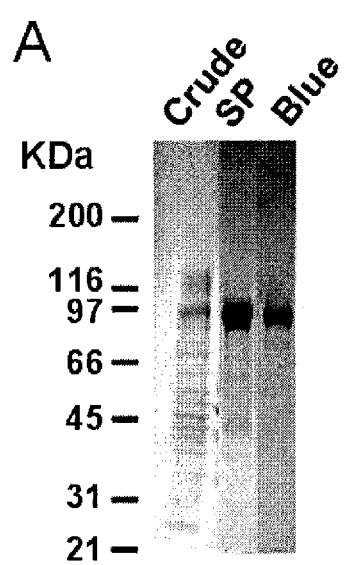
FIG. 5 presents a Sypro-Ruby™ stained SDS-PAGE analysis of the different fractions collected throughout $D_{10}$sPHEX purification procedure.

Cell supernatant was centrifuged at 500×g for 5 minutes at 4° C. and filtered on fiberglass (Fisher, APFC09050) and concentrated 10 to 40 times using an Ultrasette™ 30 tangential flow filtration device (Pall Canada). The pH of the solution was brought to 5.6 with 1 M acetic acid before an overnight dialysis at 4° C. against 50 mM sodium acetate, 100 mM NaCl pH 5.6 (SP-buffer). The dialyzed supernatant was loaded, at a flow rate of 4 ml/min, on a 20 ml SulfoPropyl-Sepharose cation-exchange column (Amersham Pharmacia Biotech) previously equilibrated with SP-buffer. The column was washed with the same buffer at the same flow rate until 280 nm absorbance baseline was reached. Most of the contaminant proteins were then eluted with a 226 mM NaCl step in the SP buffer. $D_{10}$sPHEX was then eluted with a 280 mM NaCl step (FIG. 4A). Fractions were analyzed by SDS-PAGE and with the PHEX enzymatic activity assay. Fractions containing sPHEX were pooled and extensively dialyzed against 20 mM MOPS pH 7, 250 mM NaCl prior to loading on a 5 ml Blue-Sepharose™ HP (Amersham Pharmacia) column at 5 ml/min. The column was rinsed, at the same flow rate with the same buffer and most of the $D_{10}$sPHEX protein was recovered by increasing the NaCl concentration stepwise to 350 mM (FIG. 4B). Purity of the final fraction was greater than 95%. Alternatively, the Blue-Sepharose™ could be replaced by Heparin-Sepharose™ (Amersham Pharmacia) on which $D_{10}$sPHEX binds tightly over a range of pH (5 to 8). D10sPHEX was eluted by using NaCl gradient. Purity was determined to be above 90%. $D_{10}$sPHEX was concentrated and dialyzed against 1 mM sodium PO4 pH 7.4, 150 mM NaCl using Centriprep-50™ cartridges. Dialyzed sample was filtered in a sterile environment on 0.22 µm membrane. Purified $D_{10}$sPHEX was shown to remain stable over months at 4° C. Protein concentrations were determined using the Bradford method (DC protein assay kit; Biorad) with bovine serum albumin (BSA) as a standard. Protein purity was assessed by Sypro-Ruby™ (Molecular Probes) staining of proteins resolved on SDS-PAGE 4-12% (FIG. 3). $D_{10}$sPHEX enzymatic activity was determined using the fluorigenic substrate.

Effect of sPHEX and $D_{10}$-sPHEX Injections on Circulating Levels of Alkaline Phosphatase in Hyp Mice The X-linked Hyp mice harbors a large deletion in 3' region of the PHEX gene and is the murine homologue of human X-linked hypophosphatemia (XLH). These mice therefore represent a useful model to study the pathophysiology of XLH as well as a to test the efficacy of therapeutic agents in preclinical studies.

The potential therapeutic effect of $D_{10}$sPHEX and sPHEX was thus investigated with bolus intravenous injection to Hyp/Y mice over a 2 week period.

$D_{10}$sPHEX and sPHEX were dialyzed against vehicle and the solutions were filtered through 0.22 µm low binding protein filter. The solutions were aliquoted and re-assayed for enzymatic activity and concentration by fluorogenic enzymatic assay and Bradford method, respectively.

Each mouse was anesthetized with vaporized Isoflurane (2%) and $D_{10}$sPHEX, or sPHEX were injected as an intravenous bolus through the subclavian vein. The dose was 5 mg/kg of body weight for each group. The animals were treated once daily for 14 consecutive days. Blood samples (0.1-0.2 ml) were collected via the subclavian vein under anesthesia on study days −3 and +15 (before necropsy, 24 hours after last injection). Total Alkaline phosphatase (ALP) levels were assayed in diluted serum (30 µl of serum sample with 90 µl of 0.9% saline USP). Although, appropriate dosages for human patients are not proportional to those used in mice, these dosages are predictive of the dosages ranges that could be suitable in humans using published tables.

Figure 6:
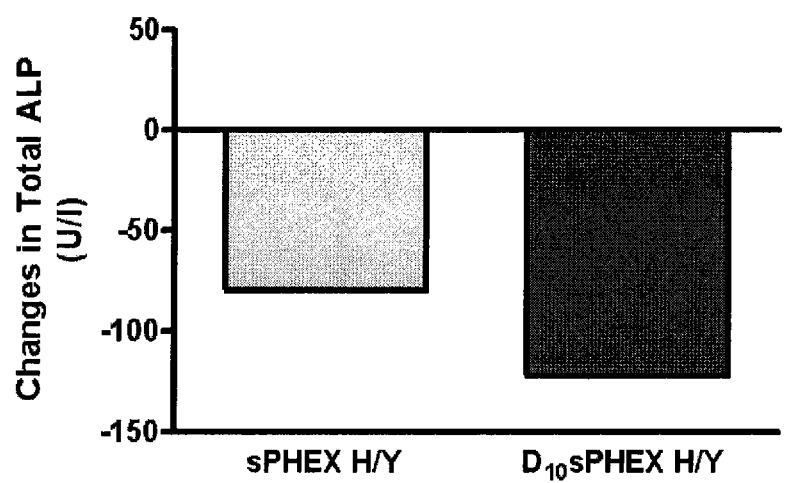
FIG. 6 shows the variation in serum alkaline phosphatase levels (ALP) observed in Hyp mice injected daily with i.v. doses of sPHEX and $D_{10}$-sPHEX for 14 days. U/I values represent the decrease observed between day −3 (corresponding in the graphic to 0 U/I) and day 15. of the injection regimen and are the mean of measures made on 6 animals.

As seen in FIG. 6 the $D_{10}$-extended form of sPHEX induced a larger decrease in alkaline phosphatase levels than the normal sPHEX form.

Example 4

$D_{10}$ Fusion to Recombinant GST Increases its Binding to the Mineral Phase of Bone In Vitro Fluorescein Labelling of Purified Proteins Recombinant purified proteins were labelled with fluorescein-isothiocyanate (FITC, Molecular Probes F143). Reaction was carried out by adding proteins to 10 mM sodium phosphate, 50 mM NaCl buffer pH 7 at a final protein concentration of 1 mg/ml. Labelling reaction was started by adding FITC dissolved in DMSO at a concentration of 20 mg/ml to reach 20:1 molar ratio with respect to the protein concentration. The mixture was left to react at room temperature for an hour. Labelled protein was separated from the free fluorescein on a PD-10™ column (Pharmacia) prior to dialysis in the binding buffer (1 mM sodium phosphate 150 mM NaCl, pH 7.4).

Preparation of the Mineral Phase of Bones

Long bones were dissected from a rat and crushed to powder in a liquid nitrogen cooled mortar. The powder was either kept at −80° C. or directly used. An aliquot of the powder (300 mg) was washed 3 times with 8 ml of PBS and 8 ml of 1 M HCl were added. The mixture was kept in suspension on a rotating mixer for 1 hour at room temperature. The insoluble fraction was spun down and the clear acidic supernatant collected. This acidic solution was stable at room temperature for at least two weeks.

Binding Reaction

Aliquots of 20 µl of the acidic bone extract were mixed with 2 µl of 10 M NaOH and the precipitate was pelleted 10,000×g for 3 minutes at room temperature. The pellet was rinsed twice by resuspending in 100 µl of binding buffer. The bone extract was then mixed with 100 µl of a solution containing 5 to 45 µg of fluorescein-labelled protein in the binding buffer to which phosphate was added to reach a final concentration of 80 mM. The samples were incubated for 30 minutes at room temperature on the rotating wheel to keep the mineral phase in suspension. The samples were then centrifuged for 3 minutes at room temperature. The pellet containing the bound protein was dissolved in 200 µl of 0.5 M EDTA pH 8. To estimate the amount of free protein present, 100 µl of 0.5 M EDTA pH 8 was added to the supernatant. Fluorescence of the different samples was measured on a 96 wells plate reader set at 494 nm for excitation and 516 nm for emission.

Results

Figure 9:
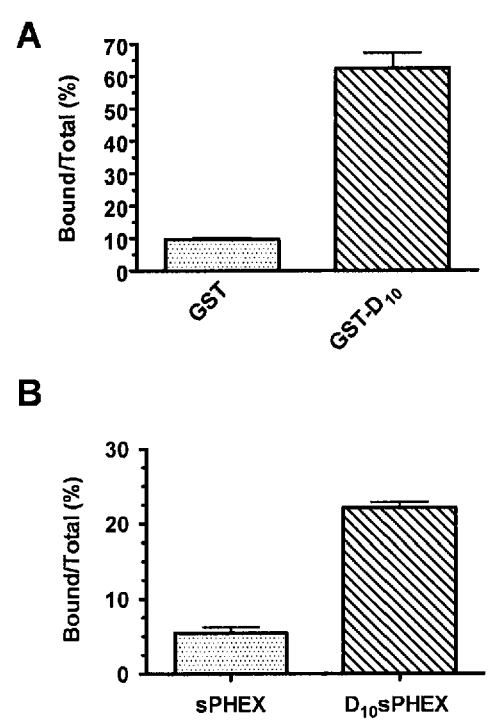
FIG. 9 compares the binding to the mineral phase of bone of proteins (A. GST B. sPHEX) with that of their decaaspartate fused counterparts.

Samples containing 50 µg of fluorescein-labelled GST and GST-$D_{10}$ were used in the binding assay described above. FIG. 9A shows that fusion of the $D_{10}$ sequence to GST caused a 6-fold increase in binding to the mineral phase of bone.

Example 5

$D_{10}$ Fusion to sPHEX Increases its Binding to Bone

Using a procedure analogous to that described in Example 4 above, samples containing 50 µg of fluorescein-labelled sPHEX and $D_{10}$sPHEX were used in a binding assay. FIG. 9B shows that fusion of the $D_{10}$ sequence to sPHEX caused a 4.3 increase in binding to the mineral phase of bone.

In contrast, $D_6$-sPHEX was constructed and tested after in vivo injection in animals (as described in Example 1 above) and did not promote binding of recombinant proteins to bone (Data not shown).

Example 6

$D_{10}$ Fusion to a Soluble Form of Alkaline Phosphatase Increases its Targeting to the Mineral Phase of Bone Construction of Expression Vectors Encoding Human Recombinant Soluble Phosphatase Alkaline, sALP and sALP-$D_{10}$ The human full length cDNA encoding tissue non-specific alkaline phosphatase (ALP) was obtained from bone marrow polyA RNA (Clonetech) by RT-PCR. Briefly, 20 ng of polyA was reverse transcribed with SuperscriptII™ and an oligo dT$_{12-18}$ using the First Strand Synthesis System (Invitrogen). An aliquot representing $\frac{1}{20}^{th}$ of the RT step was used directly in a PCR reaction with ALP specific oligos (forward 5'-gataaagcaggtcttggggtgcacc-3' (SEQ ID NO: *); reverse 5'-gttggcatctgtcacgggcttgtgg-3' (SEQ ID NO: *)) and the Expand High Fidelity Enzyme Kit™ (Roche). The resulting ALP specific product (1644 bp) was separated on and purified from an agarose gel (1%) using the Qiaquick Gel Extraction Kit™ (QIAGEN). The ALP cDNA was then ligated into the pCR4-blunt-TOPO™ vector (Invitrogen), transformed into Top10™ bacteria (Invitrogen), and a positive clone identified by colony PCR. The identity of the cDNA was verified by automated DNA sequencing.

Secreted forms of ALP (sALP) having the GPI anchor signal removed were constructed by PCR using Expand High Fidelity Enzyme Kit™. They comprised residues 1-502 followed by either a stop codon (sALP) or a deca aspartate targeting motif and a stop codon (sALP-D10). In both cases the forward primer (5'-tggatccacc atgatttcaccattcttagtac-3' (SEQ ID NO: 40)) covered the initiator methionine (underlined) and included a BamHI site (italicized). The reverse primers (sALP: 5'-ttctaga ctacgagctggcaggagcacagtggccg-3' (SEQ ID NO: 41); sALP-$D_{10}$ 5'-ttctaga ctagtcgtcatcatcgtcatcatcgtcgtcatccgagctggcaggagcacagtgg ccg-3' (SEQ ID NO: 42)) contained a stop codon (underlined) and an XbaI site (italicized). The PCR products were digested with BamHI and XbaI and cloned into the pCDNA3.1-RSV that had been pre-digested with the same enzymes. Plasmid DNA were sequenced.

ALP Fluorescent Enzymatic Assay

Enzymatic activity of sALP and sALP-$D_{10}$ was assayed using 4-methylumbelliferyl phosphate (MUP, Molecular Probes, M8425) as a fluorigenic substrate according to Gee K R et al. (Anal. Biochem. 273, 41-48 (1999)) Typically, the assay was carried out at 37° C. in 96-well plates in a final volume of 200 µl with 10 µM of MUP. Readings were recorded using a Spectramax Gemini™ (Molecular Devices) plate reader every minute for 30 minutes at 450 nm upon excitation at 360 nm. Emission wavelength cut-off was set at 435 nm. ALP initial speed rate was estimated by linear regression fitting (with $r^2$ equal or greater than 0.98).

Expression of Recombinant sALP and sALP-$D_{10}$ Proteins

In order to determine whether the recombinant sALP and sALP-$D_{10}$ proteins were secreted, each construct (pCDNA3-RSV-sALP-NEO and pCDNA3-RSV-sALP-$D_{10}$-NEO) was transiently transfected in HEK-293S cells (Human Embryonic Kidney cells; ATCC No. CRL-1392) using the Lipofectamine-Plus Liposome Transfection Kit™ (Invitrogen). HEK-293S cells were also mock-transfected as a negative control. The day after transfection, cells were incubated for 24 h in serum-free DMEM. The conditioned media were collected and centrifuged at 14000 RPM for 5 min at 4° C. to remove dead cells and debris. The supernatants were assayed for sALP or sALP-$D_{10}$ enzymatic activity and expression using the ALP fluorescent enzymatic assay and Western blotting respectively. For Western blotting, the spent media were precipitated for 1 h on ice with trichloroacetic acid (final concentration 10% (v/v)). The precipitated proteins were spun down at 14000 RPM for 20 min at 4° C., washed once with chilled acetone, dried, and resuspended in 60 µl 1× Laemmli sample buffer with DTT and boiled for 5 min.

To evaluate the intracellular content of sALP and sALP-$D_{10}$ the cells were washed 3 times with PBS and lysed with 200 µl Tris-HCl 50 mM (pH 8) containing 150 mM NaCl and 1% NP-40 on ice for 20 min. The lysates were spun down and the supernatant was assayed for sALP or sALP-$D_{10}$ enzymatic activity and expression using the ALP fluorescent enzymatic assay and Western blotting, respectively. For Western blotting, 50 µl aliquots were mixed with 10 µl 6× Laemmli sample buffer with DTT and boiled for 5 min.

Samples were loaded on a Novex Precast™ 4-12% Tris-Glycine polyacrylamide gel (Invitrogen) and transferred onto 0.45 µm nitrocellulose (Protran, Schleicher&Schuell, Keene, N.H.) with Tris-glycine containing 10% methanol. The membrane was stained with Ponceau red and blocked for 1 h at room temperature with PBS containing 0.05%

Tween 20™ (PBST) and 5% dried milk. The membrane was then sequentially incubated at room temperature with the anti-hBAP antibody (mAb 4B-78, Developmental Studies Hybridoma Bank) (1:1000 in PBST with 5% dried milk) and a rabbit anti-mouse IgG coupled to horseradish peroxidase (Sigma) (1:12000 in PBST with 5% dried milk). The signal was developed with the Western Lightning Chemiluminescence Reagent Plus™ (PerkinElmer).

Figure 13:
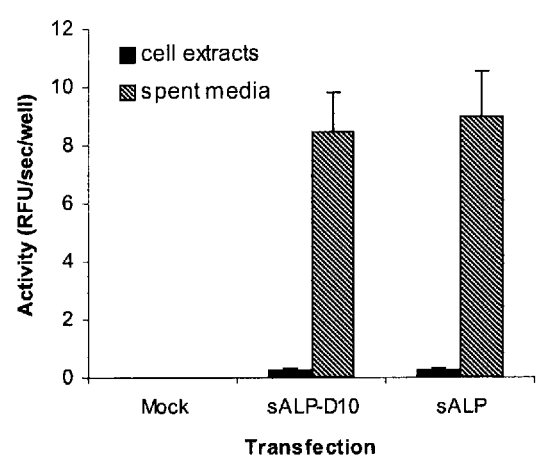
FIG. 13 graphically illustrates through fluorimetric measurement of the alkaline phosphatase activity in the soluble cell extract and spent medium of HEK293 transiently transfected with expression vectors encoding sALP-$D_{10}$ and sALP.
Figure 14:
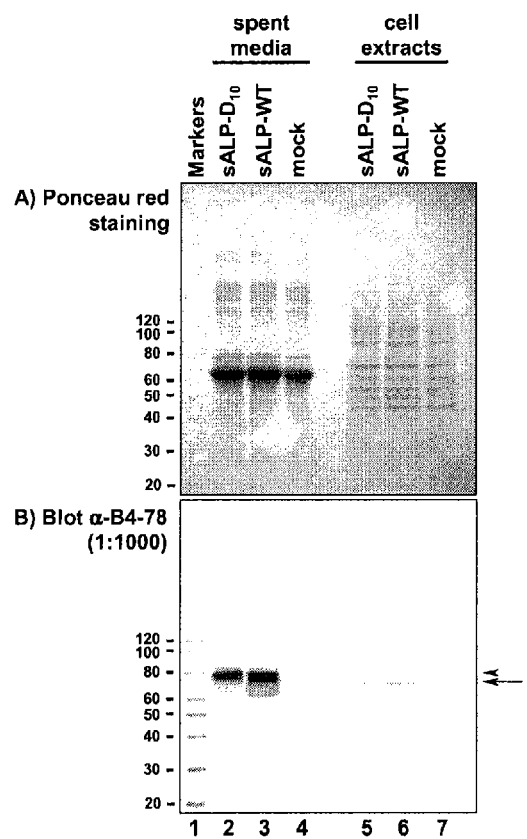
FIG. 14 graphically illustrates the detection of sALP and sALP-$D_{10}$ by Western blotting with the specific B4-78 antibody in the spent media and cell extract of HEK-293 after transient transfection. (Panel A: Ponceau red staining; Panel B: Blot a-B4-78). Shown on the left are the sizes of the molecular weight markers.

The ALP enzymatic activity measured in the conditioned media of HEK293 after transient transfection was very high and of similar magnitude for pCDNA3-RSV-sALP-NEO (sALP) and pCDNA3-RSV-sALP-$D_{10}$-NEO (sALP-$D_{10}$) (FIG. 13). This activity was specific to the plasmid DNA transfected as it was undetectable in mock-transfected cells (mock). The relative activity measured in the media was 35-times greater than that measured in the cell extracts thus attesting to the secretory nature of sALP and sALP-$D_{10}$. Accordingly, for both sALP and sALP-$D_{10}$, immunoblotting using a monoclonal antibody raised against recombinant tissue non-specific human alkaline phosphatase (mAb 4B-78, Developmental Studies Hybridoma Bank) revealed a much stronger signal in the conditioned media than in the cell extracts (FIG. 14B, compare lanes 2, 3 vs. 5, 6). No signal was visualized in the mock-transfected samples (FIG. 14B, lanes 4 and 7). The signal appearing in the mock-transfected cells consists of BSA trace. The apparent molecular weight of the protein detected was estimated to be 70 kDa in the cell extracts (arrow) and slightly higher in the conditioned media (arrowhead). Ponceau red staining of the membrane was performed to monitor the uniform loading of samples (FIG. 14A).

Generation of HEK293 Cells Constitutively Secreting sALP and sALP-$D_{10}$

To induce the stable expression of the sALP and sALP-$D_{10}$ proteins, the pCDNA3-RSV-sALP-NEO and pCDNA3-RSV-sALP-$D_{10}$-NEO vectors was transfected separately in HEK-293S cells using the Lipofectamine-Plus Liposome Transfection Kit™ (Invitrogen). Transfected cells were selected by adding 800 μg/ml G418 (Life Technologies) to the medium. For each transfection a pool of G-418 resistant cells were analyzed for sALP or sALP-$D_{10}$ expression in the spent culture media using the ALP fluorescent enzymatic assay. The conditioned media collected from the stable cell lines were used for the binding assay study on the bone mineral.

Binding to Reconstituted Mineral Phase of Bone

Aliquots of 20 μl of the acidic bone extract were mixed with 2 μl of 10 M NaOH and the precipitate was pelleted at 10,000×g for 3 minutes at room temperature. The pellet was rinsed twice in 100 μl of buffer (1 mM sodium phosphate pH 7.4+150 mM NaCl). The resultant mineral phase of bone (equivalent to 0.37 mg of dried powder) was then mixed with 100 μl of a solution containing sALP or sALP-$D_{10}$ proteins in the binding buffer (80 mM sodium phosphate pH 7.4+150 mM NaCl). The samples were incubated for 30 minutes at room temperature on the rotating wheel to keep the mineral phase in suspension. The samples were then centrifuged for 3 minutes at room temperature. The pellet containing the bound protein was mixed with 180 μl of the ALP enzymatic assay buffer containing 0.1% BSA and the reaction initiated by adding 20 μl of 100 μM MUP. To allow for more homogeneous assay, conditions the 96 wells plate was shaken for 10 seconds every minute for the duration of the assay.

Enzymatic activity retained on reconstituted mineral bone phase was compared to the equivalent enzymatic activity added in the binding assay. Values of 0.98% and 13.3% of total protein activity bound to the bone mineral phase were calculated for sALP and sALP-$D_{10}$ respectively. A binding difference of more than 13 times in favour of sALP-$D_{10}$ suggests that the C-terminal fused deca-aspartate sequence directly targets sALP to the mineral phase of bone. Furthermore, the fact that it was possible to measure directly ALP activity bound to the mineral phase of bone indicates that the enzyme is bound in a catalytically competent form to hydroxyapatite crystals.

Such fusion protein can be targeted directly to bones where the accumulation of PPi inhibits skeletal mineralization.

Example 7

$D_{10}$-ALP Decreases Inhibitory Effect of Pyrophosphate on Bone Mineralization UMR106 cells were grown to confluence. They were then cultured for a further 7 days in media containing 10 mM β-glycerophosphate to induce mineralization. Throughout this 7-day culture period, cells were treated with or without 75 μM pyrophosphate (PPi), a mineralization inhibitor and a alkaline phosphatase substrate. To assess the ability of alkaline phosphatase to rescue the PPi-induced mineralization inhibition, cells treated with or without PPi were cultured with varying concentrations of semi-purified $D_{10}$-sALP produced from HEK293, human embryonic kidney cells. Mineralization was assessed by $^{45}$Ca uptake. Parameters used for this experiment are presented in table 2 below.

TABLE 2

PARAMETERS USED IN $D_{10}$-ALP ON PPi-INDUCED MINERALIZATION INHIBITION

| ALP | [ALP] (Units/well) | μl ALP/well | β-GP (mM) | PPi (μM) |
|---|---|---|---|---|
| — | 0 | 0 | 10 | 0 |
| — | 0 | 0 | 10 | 75 |
| $D_{10}$-sALP | 1.5 | 0.5 | 10 | 0 |
| $D_{10}$-sALP | 1.5 | 0.5 | 10 | 75 |
| $D_{10}$-sALP | 3 | 1.0 | 10 | 0 |
| $D_{10}$-sALP | 3 | 1.0 | 10 | 75 |
| $D_{10}$-sALP | 4.5 | 1.5 | 10 | 0 |
| $D_{10}$-sALP | 4.5 | 1.5 | 10 | 75 |
| $D_{10}$-sALP | 6 | 2 | 10 | 0 |
| $D_{10}$-sALP | 6 | 2 | 10 | 75 |

7-days of treatment with PPi resulted in a 43% decrease in mineralization. Co-treatment of cultures with $D_{10}$sALP resulted in a dose-responsive rescue of this mineralization inhibition. Treatment with 1.5 units of $D_{10}$-sALP resulted in a 30% decrease, 3 and 4.5 units a 24% decrease and 6 units resulted in a 15% decrease in mineralization, corresponding to a 65% rescue of PPi-induced mineralization inhibition.

These results show that the treatment of mineralizing osteoblast with $D_{10}$-sALP dose-responsively rescues mineralization inhibition induced by PPi.

The above Examples shows that a poly-aspartate fusion to recombinant proteins increases their binding to the mineral phase of bone or to bone tissue and increases the ability of the protein to perform its biological activity as compared to when it is administered alone.

Although the present invention has been described hereinabove by way of preferred embodiments thereof, it can be modified, without departing from the spirit and nature of the subject invention as defined in the appended claims.

REFERENCES

1—Weinberg, J M (2003) An overview of infliximab, etanercept, efalizumab, and alefacept as biologic therapy for psoriasis. Clin Ther 25: 2487-2505.
2—Whyte M P, Valdes R Jr, Ryan L M, McAlister W H (1982) Infantile hypophosphatasia: enzyme replacement therapy by intravenous infusion of alkaline phosphatase-rich plasma from patients with Paget bone disease. J Pediatr 101: 379-386.
3—Whyte M P, Kurtzberg J, McAlister W H, Mumm S, Podgornik M N, Coburn S, Ryan L M, Miller C R, Gottesman G S, Smith A K, Douville J, Waters-Pick B, Armstrong R D, Martin P L (2003) Marrow cell transplantation for infantile hypophosphatasia. J Bone Miner Res 18: 624-636.
4—Fujisaki J, Tokunaga Y, Takahashi T, Shimojo F, Kimura S, Hata T (1997) Osteotropic drug delivery system (ODDS) based on biphosphonic prodrugs. IV: Effects of osteotropic estradiol on bone mineral density and uterine weight in ovariectomized rats. J Drug Targeting 5: 129-138.
5—Uludag H, Gao T, Wohl G R, Kantoci D, Zemicke R F (2000) Bone affinity of a biphosphonate-conjugated protein in vivo. Biotechnol Prog 16: 1115-1118.
6—Sekido T, Sakura N, Higashi Y, Miya K, Nitta Y, Nomura M, Sawanishi H, Morito K, Masamune Y, Kasugai S, Yokogawa K, Miyamoto K-I (2001) Novel drug delivery system to bone using acidic oligopeptides: pharmacokinetic characteristics and pharmacological potential. J Drug Targeting 9: 111-121.
7—Hunter G K, Kyle C L, Goldberg H A (1994) Modulation of crystal formation by bone phosphoproteins: structural specificity of the osteopontin-mediated inhibition of hydroxyapatite formation. Biochem J 300: 723-728.
8—Rowe P S N, de Zoysa P A, Dong R, Wang H R, White K E, Econs M J, Oudet C L (2000) MEPE, a new gene expressed in bone marrow and tumors causing osteomalacia. Genomics 67: 54-68.
9—Gilbert M, Shaw W J, Long J R, Nelson K, Drobny G P, Giachelli C M, Stayton P S (2000) Chimeric peptides of statherin and osteopontin that bind hydroxyapatite and mediate cell adhesion. J Biol Chem 275: 16213-16218.
10—Young M F, Kerr J M, Ibaraki K, Heegaard A M, Robey P G (1992) Structure, expression, and regulation of the major noncollagenous matrix proteins of bones. Clin Orthop 281: 275-294.
11—Salih E, Ashkar S, Gerstenfeld F C, Glimcher M J (1997) Identification of the phosphorylated sites of metabolically 32P-labeled osteopontin from cultured chicken osteoblasts. J Biol Chem 272: 13966-13973.
12—Campbell P G, Andress D L (1997) Insulin-like growth factor (IGF)-binding protein-5-(201-218) region regulates hydroxyapatite and IGF-I binding. Am J Physiol 273: E1005-E1013.
13—Patti J M, House-Pompeo K, Boles J O, Garza N, Gurusiddappa S, Hook M (1995) Critical residues in the ligand-binding site of the *Staphylococcus aureus* collagen-binding adhesin (MSCRAMM). J Biol Chem 270: 12005-12011.
14—Symersky J, Patti J M, Carson M, House-Pompeo K, Teale M, Moore D, Jin L, Schneider A, DeLucas L J, Hook M, Narayana S V (1997) Structure of the collagen-binding domain from a *Staphylococcus aureus* adhesin. Nat Struct Biol 4: 833-838.

What is claimed is:

1. A bone delivery conjugate having a structure selected from the group consisting of:

A) $X\text{-}D_n\text{-}Y\text{-}protein\text{-}Z$; and

B) $Z\text{-}protein\text{-}Y\text{-}D_n\text{-}X$, wherein the protein is a soluble alkaline phosphatase (sALP) that is not a soluble form of a tissue non-specific alkaline phosphatase;

wherein X is absent or is an amino acid sequence of at least one amino acid;

Y is absent or is an amino acid sequence of at least one amino acid;

Z is absent or is an amino acid sequence of at least one amino acid; and $D_n$ is a poly aspartate wherein n=10 to 16.

2. The bone delivery conjugate of claim 1, wherein said structure is: $Z\text{-}sALP\text{-}Y\text{-}D_n\text{-}X$.

3. The bone delivery conjugate of claim 2, wherein n=10.

4. A bone delivery composition comprising the bone delivery conjugate of claim 1 and a pharmaceutically acceptable carrier.

5. A method of delivering a protein to bone tissue of a mammal comprising administering to said mammal an effective amount of the bone delivery conjugate of claim 1.

6. A method of delivering ALP to bone tissue of a mammal in need thereof comprising administering to said mammal an effective amount of the bone delivery conjugate of claim 1.

7. A method of treating a condition or disease related to a bone defect characterized by a lack of or an insufficient amount of functional alkaline phosphatase comprising administering to a mammal in need thereof the conjugate of claim 1, said conjugate being in a pharmaceutically acceptable carrier.

8. The method of claim 7, wherein the condition or disease is hypophosphatasia.

* * * * *